(12) United States Patent  
Sparks et al.

(10) Patent No.: US 7,004,173 B2  
(45) Date of Patent: Feb. 28, 2006

(54) CATHETER SYSTEM FOR VASCULAR RE-ENTRY FROM A SUB-INTIMAL SPACE

(75) Inventors: Kurt D. Sparks, Palo Alto, CA (US); Jeffrey L. Emery, San Mateo, CA (US); Brent D. Seybold, Santa Clara, CA (US); David J. Kupiecki, San Francisco, CA (US); C. Danielle Pinson, Mountain View, CA (US); Allen W. Madsen, San Jose, CA (US); Michael D. Keleher, Fremont, CA (US); Sergio Salinas, Redwood City, CA (US); Benjamin J. Clark, Redwood City, CA (US); Matthew R. Selmon, Atherton, CA (US)

(73) Assignee: LuMend, Inc., Redwood City, CA (US)

( * ) Notice: Subject to any disclaimer, the term of this patent is extended or adjusted under 35 U.S.C. 154(b) by 334 days.

(21) Appl. No.: 10/010,410

(22) Filed: Dec. 5, 2001

(65) Prior Publication Data

US 2002/0103459 A1    Aug. 1, 2002

Related U.S. Application Data

(60) Provisional application No. 60/329,936, filed on Oct. 17, 2001, provisional application No. 60/301,537, filed on Jun. 27, 2001, provisional application No. 60/268,263, filed on Feb. 12, 2001, provisional application No. 60/263,589, filed on Jan. 22, 2001, provisional application No. 60/263,580, filed on Jan. 22, 2001, provisional application No. 60/263,579, filed on Jan. 22, 2001, provisional application No. 60/263,397, filed on Jan. 22, 2001, provisional application No. 60/263,350, filed on Jan. 22, 2001, provisional application No. 60/255,729, filed on Dec. 14, 2000, provisional application No. 60/251,756, filed on Dec. 5, 2000.

(51) Int. Cl.  
*A61B 19/00* (2006.01)

(52) U.S. Cl. .................... 128/898; 604/500; 606/190

(58) Field of Classification Search ............. 606/159, 606/108; 600/585, 435; 604/523, 500; 128/898  
See application file for complete search history.

(56) References Cited

U.S. PATENT DOCUMENTS

| | | |
|---|---|---|
| 832,201 A | 10/1906 | Kistler |
| 1,127,948 A | 2/1915 | Wappler |
| 1,267,066 A | 4/1918 | Flack |
| 1,747,407 A | 2/1930 | Wappler |
| 2,621,651 A | 12/1952 | Wallace |

(Continued)

*Primary Examiner*—(Jackie) Tan-Uyen T. Ho  
(74) *Attorney, Agent, or Firm*—Courtney Staniford & Gregory LLP

(57) ABSTRACT

A catheter system and corresponding methods are provided for accessing a blood vessel true lumen from a sub-intimal plane of the vessel. The catheter system includes visualization elements for determining the orientation of the true lumen with respect to the sub-intimal plane at an identified entry site from a position in the sub-intimal plane. The entry site is distal to a chronic total occlusion (CTO). The catheter system also includes a system for physically securing tissue of the sub-intimal plane at the entry site to the catheter system. The attaching system reduces or eliminates catheter float within the sub-intimal space. The catheter system further includes re-entry devices to establish and maintain a path from the sub-intimal plane back into the vessel true lumen.

19 Claims, 65 Drawing Sheets

U.S. PATENT DOCUMENTS

| | | | |
|---|---|---|---|
| 3,640,270 A | 2/1972 | Hoffman |
| 3,667,474 A | 6/1972 | Lapkin |
| 4,043,323 A | 8/1977 | Komiya |
| 4,355,643 A | 10/1982 | Laughlin et al. |
| 4,405,314 A | 9/1983 | Cope |
| 4,541,433 A | 9/1985 | Baudino |
| 4,552,554 A | 11/1985 | Gould et al. |
| 4,572,286 A | 2/1986 | Fujii et al. |
| 4,585,000 A | 4/1986 | Hershenson |
| RE32,158 E | 5/1986 | Vukovic |
| 4,594,074 A | 6/1986 | Andersen et al. |
| 4,630,609 A | 12/1986 | Chin |
| 4,648,402 A | 3/1987 | Santos |
| 4,669,467 A | 6/1987 | Willett et al. |
| 4,681,110 A | 7/1987 | Wiktor |
| 4,688,234 A | 8/1987 | Robinton |
| 4,698,057 A | 10/1987 | Joishy |
| 4,723,549 A | 2/1988 | Wholey et al. |
| 4,737,142 A | 4/1988 | Heckele |
| 4,774,949 A | 10/1988 | Fogarty |
| 4,787,388 A | 11/1988 | Hofmann |
| 4,794,928 A | 1/1989 | Kletschka |
| 4,842,585 A | 6/1989 | Witt |
| 4,848,336 A | 7/1989 | Fox et al. |
| 4,862,874 A | 9/1989 | Kellner |
| 4,919,112 A | 4/1990 | Siegmund |
| 4,947,864 A | 8/1990 | Shockey et al. |
| 4,966,596 A * | 10/1990 | Kuntz et al. .................. 606/7 |
| 5,001,556 A | 3/1991 | Nakamura et al. |
| 5,011,488 A | 4/1991 | Ginsburg |
| 5,019,040 A | 5/1991 | Itaoka et al. |
| 5,029,588 A * | 7/1991 | Yock et al. ................ 600/471 |
| 5,030,201 A | 7/1991 | Palestrant |
| 5,034,001 A | 7/1991 | Garrison et al. |
| 5,061,245 A | 10/1991 | Waldvogel |
| 5,089,001 A | 2/1992 | Hwang |
| 5,092,839 A | 3/1992 | Kipperman |
| 5,095,911 A | 3/1992 | Pomeranz |
| 5,098,381 A | 3/1992 | Schneider |
| 5,099,850 A | 3/1992 | Matsui et al. |
| 5,100,425 A | 3/1992 | Fischell et al. |
| 5,102,390 A | 4/1992 | Crittenden et al. |
| 5,109,830 A | 5/1992 | Cho |
| 5,114,414 A | 5/1992 | Buchbinder |
| 5,127,917 A | 7/1992 | Niederhauser et al. |
| 5,179,961 A | 1/1993 | Littleford, deceased et al. |
| 5,180,368 A | 1/1993 | Garrison |
| 5,183,470 A | 2/1993 | Wettermann |
| 5,190,528 A | 3/1993 | Fonger et al. |
| 5,192,290 A | 3/1993 | Hilal |
| 5,193,546 A | 3/1993 | Shaknovich |
| 5,197,971 A | 3/1993 | Bonutti |
| 5,209,729 A | 5/1993 | Hofmann et al. |
| 5,211,645 A | 5/1993 | Baumgart et al. |
| 5,217,484 A | 6/1993 | Marks |
| 5,263,959 A | 11/1993 | Fischell |
| 5,263,963 A | 11/1993 | Garrison et al. |
| 5,279,565 A | 1/1994 | Klein et al. |
| 5,282,817 A | 2/1994 | Hoogeboom et al. |
| 5,287,861 A | 2/1994 | Wilk |
| 5,304,199 A | 4/1994 | Myers |
| 5,321,501 A | 6/1994 | Swanson et al. |
| 5,334,210 A | 8/1994 | Gianturco |
| 5,336,252 A | 8/1994 | Cohen |
| 5,350,377 A | 9/1994 | Winston et al. |
| 5,351,678 A | 10/1994 | Clayton et al. |
| 5,383,467 A | 1/1995 | Auer et al. |
| 5,389,096 A | 2/1995 | Aita et al. |
| 5,409,019 A | 4/1995 | Wilk |
| 5,409,453 A | 4/1995 | Lundquist et al. |
| 5,413,581 A | 5/1995 | Goy |
| 5,415,636 A | 5/1995 | Forman |
| 5,423,846 A | 6/1995 | Fischell |
| 5,429,144 A | 7/1995 | Wilk |
| 5,443,497 A | 8/1995 | Venbrux |
| 5,452,733 A | 9/1995 | Sterman et al. |
| 5,456,667 A | 10/1995 | Ham et al. |
| 5,456,694 A | 10/1995 | Marin et al. |
| 5,456,714 A | 10/1995 | Owen |
| 5,459,570 A | 10/1995 | Swanson et al. |
| 5,464,395 A | 11/1995 | Faxon et al. |
| 5,484,412 A | 1/1996 | Pierpont |
| 5,486,170 A | 1/1996 | Winston et al. |
| 5,486,193 A | 1/1996 | Bourne et al. |
| 5,490,859 A | 2/1996 | Mische et al. |
| 5,493,000 A | 2/1996 | Aharoni |
| 5,499,995 A | 3/1996 | Teirstein |
| 5,501,694 A | 3/1996 | Ressemann et al. |
| 5,507,295 A | 4/1996 | Skidmore |
| 5,507,296 A | 4/1996 | Bales et al. |
| 5,511,559 A | 4/1996 | Vance |
| 5,531,700 A | 7/1996 | Moore et al. |
| 5,540,707 A | 7/1996 | Ressemann et al. |
| 5,556,408 A | 9/1996 | Farhat |
| 5,573,531 A | 11/1996 | Gregory |
| 5,599,306 A | 2/1997 | Klein et al. |
| 5,607,435 A | 3/1997 | Sachdeva et al. |
| 5,626,599 A | 5/1997 | Bourne et al. |
| 5,626,607 A | 5/1997 | Malecki et al. |
| 5,628,761 A | 5/1997 | Rizik |
| 5,649,941 A | 7/1997 | Lary |
| 5,653,684 A | 8/1997 | Laptewicz et al. |
| 5,662,671 A | 9/1997 | Barbut et al. |
| 5,695,457 A | 12/1997 | St. Goar et al. |
| 5,707,389 A | 1/1998 | Louw et al. |
| 5,707,390 A | 1/1998 | Bonutti |
| 5,713,907 A | 2/1998 | Hogendijk et al. |
| 5,741,270 A | 4/1998 | Hansen et al. |
| 5,800,389 A | 9/1998 | Burney et al. |
| 5,800,450 A | 9/1998 | Lary et al. |
| 5,816,923 A | 10/1998 | Milo et al. |
| 5,830,222 A | 11/1998 | Makower |
| 5,910,133 A | 6/1999 | Gould |
| 5,928,138 A | 7/1999 | Knight et al. |
| 5,935,108 A | 8/1999 | Katoh et al. |
| 5,938,671 A | 8/1999 | Katoh et al. |
| 5,951,482 A * | 9/1999 | Winston et al. ............. 600/476 |
| 5,951,541 A | 9/1999 | Simpson et al. |
| 6,015,423 A | 1/2000 | Andrese |
| 6,036,713 A | 3/2000 | Kieturakis |
| 6,048,349 A * | 4/2000 | Winston et al. ............. 606/108 |
| 6,068,638 A | 5/2000 | Makower |
| 6,071,292 A | 6/2000 | Makower et al. |
| 6,081,738 A | 6/2000 | Hinohara et al. |
| 6,126,649 A | 10/2000 | VanTassel et al. |
| 6,159,225 A | 12/2000 | Makower |
| 6,168,610 B1 | 1/2001 | Marin et al. |
| 6,190,353 B1 | 2/2001 | Makower et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,231,587 B1 | 5/2001 | Makower |
| 6,235,000 B1 | 5/2001 | Milo et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,299,622 B1 * | 10/2001 | Snow et al. ................ 606/159 |
| 6,302,875 B1 | 10/2001 | Makower et al. |
| 6,330,884 B1 | 12/2001 | Kim |
| 6,375,615 B1 | 4/2002 | Flaherty et al. |
| 6,398,798 B1 | 6/2002 | Selmon et al. |
| 6,447,539 B1 | 9/2002 | Nelson et al. |
| 6,491,707 B1 | 12/2002 | Makower et al. |
| 6,511,458 B1 | 1/2003 | Milo et al. |

| | | | | | |
|---|---|---|---|---|---|
| 6,514,217 B1 | 2/2003 | Selmon et al. | 2002/0002349 A1 | 1/2002 | Flaherty |
| 6,544,230 B1 | 4/2003 | Flaherty et al. | 2002/0123698 A1 | 9/2002 | Garibotto |
| 6,561,998 B1 | 5/2003 | Roth et al. | 2003/0078562 A1 | 4/2003 | Makower |
| 6,579,311 B1 | 6/2003 | Makower | | | |
| 2001/0047165 A1 | 11/2001 | Makower | | | |

* cited by examiner

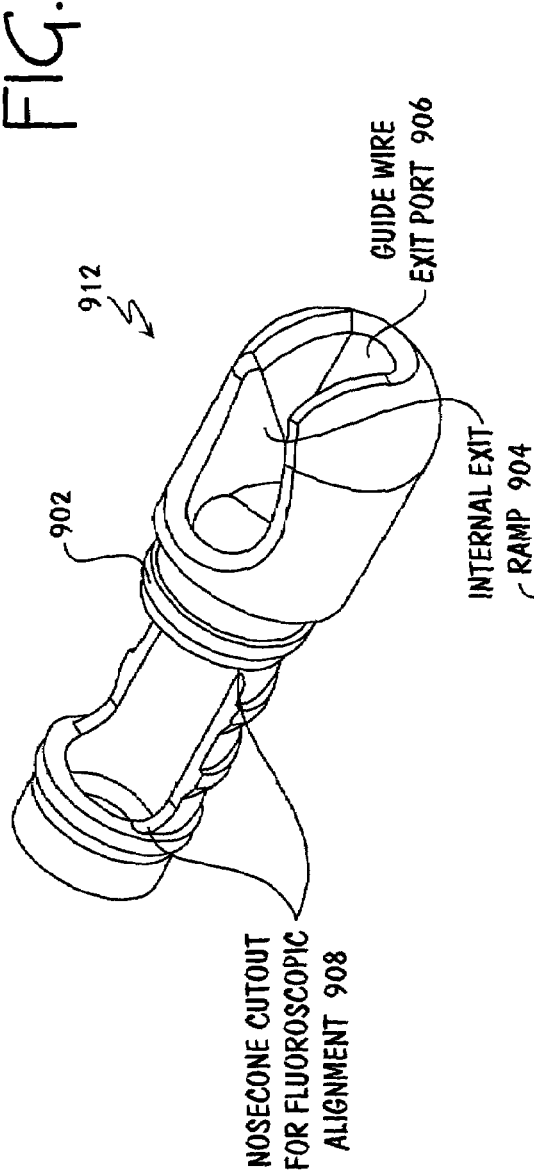
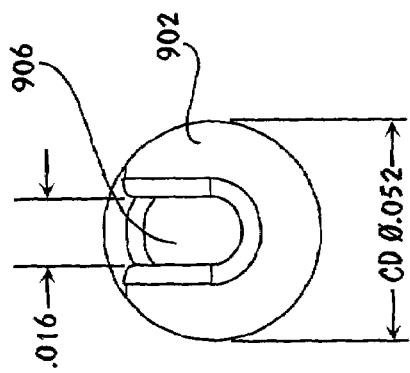
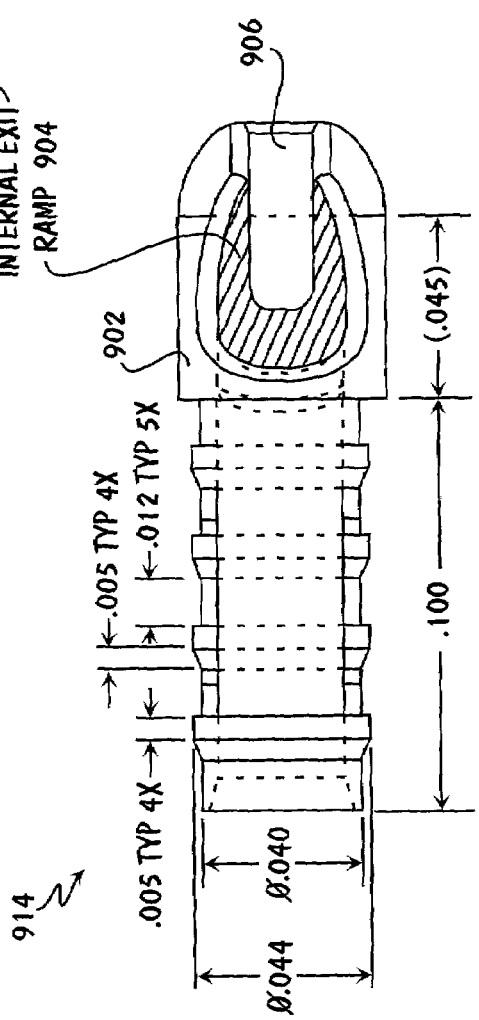
FIG. 9AA
FIG. 9AB
FIG. 9AC

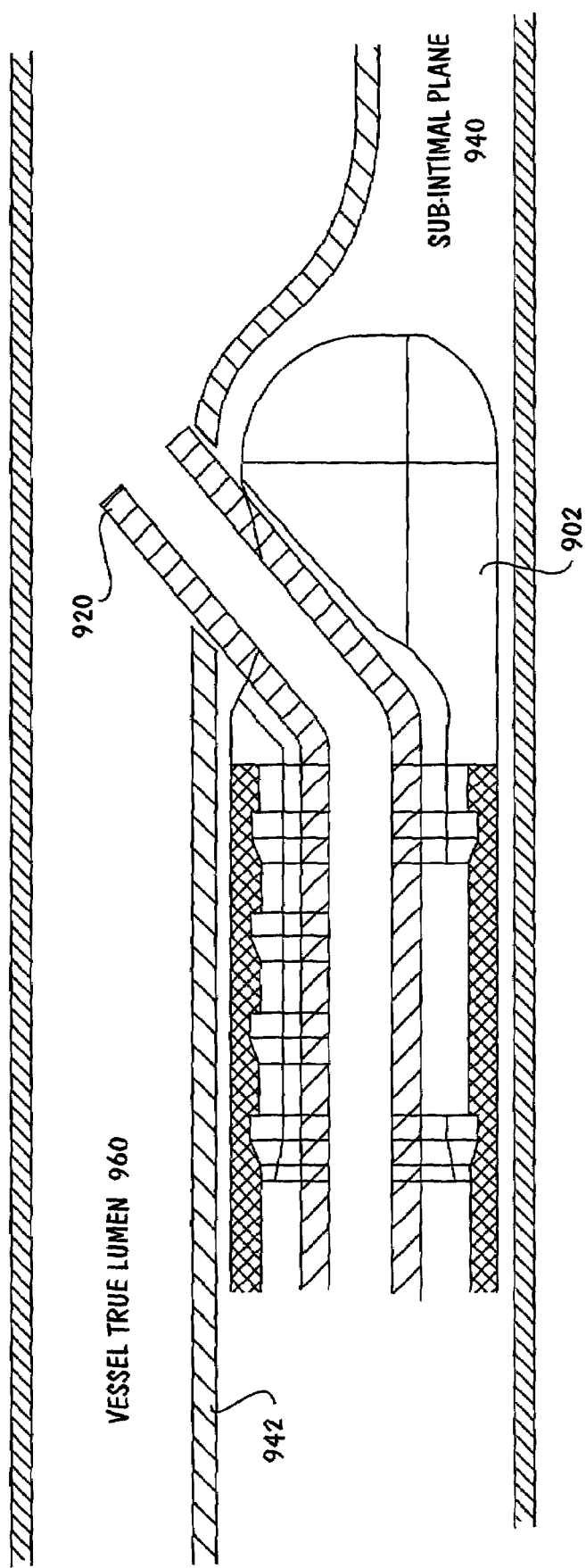

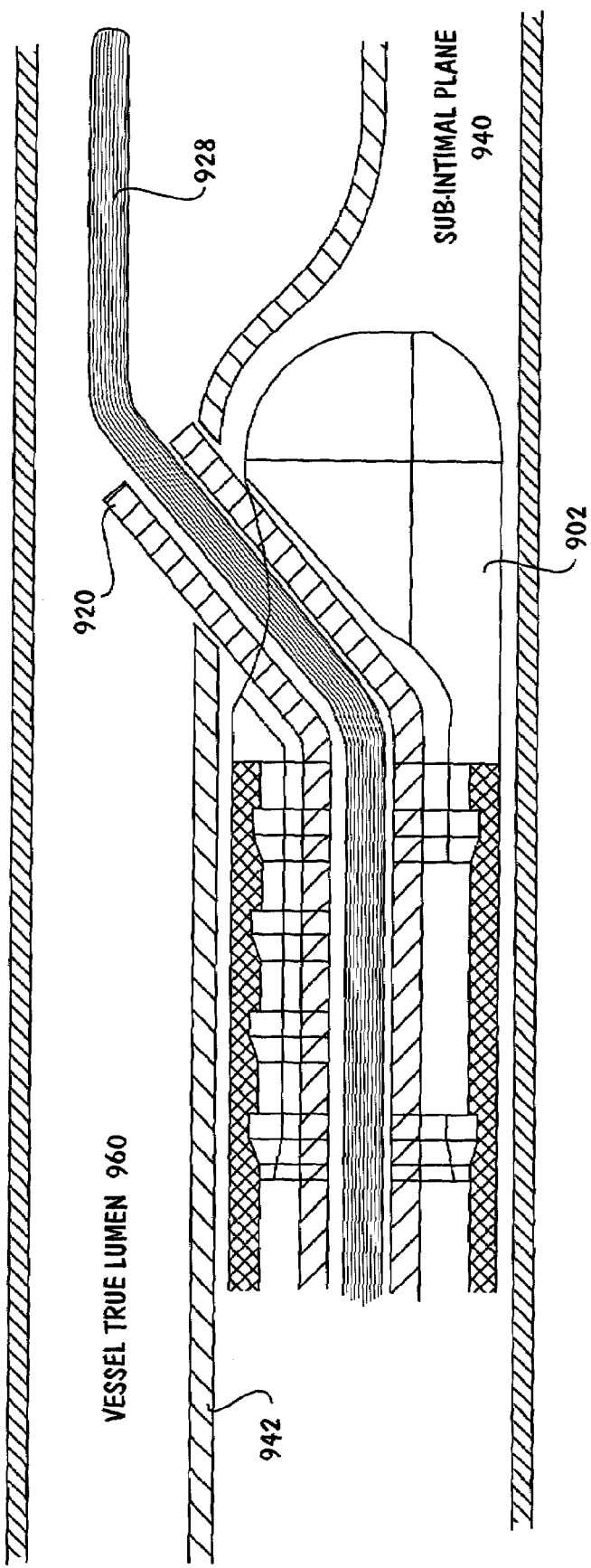

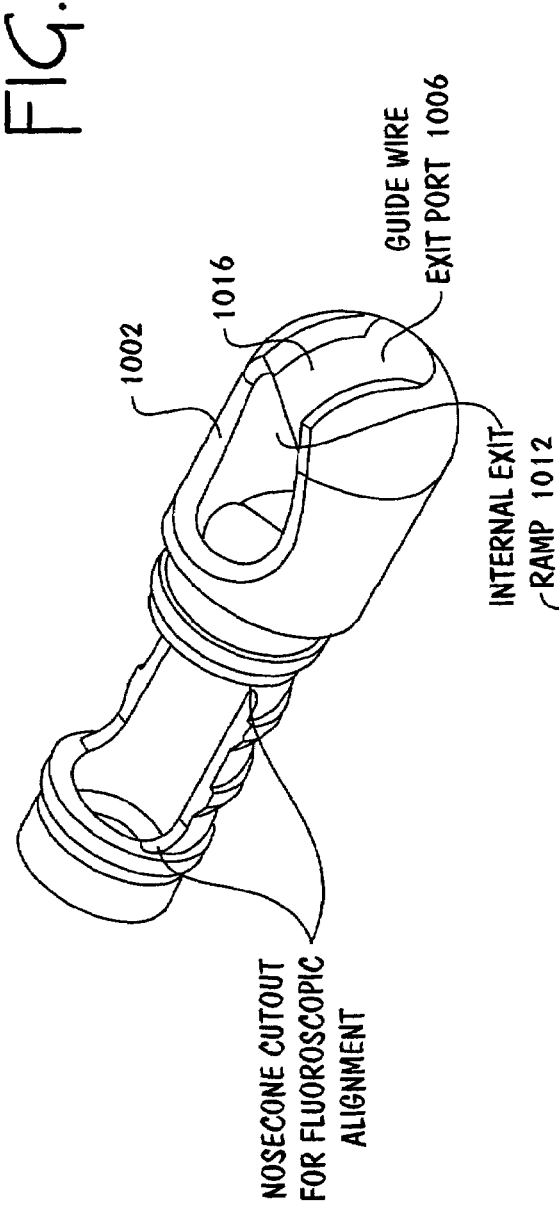
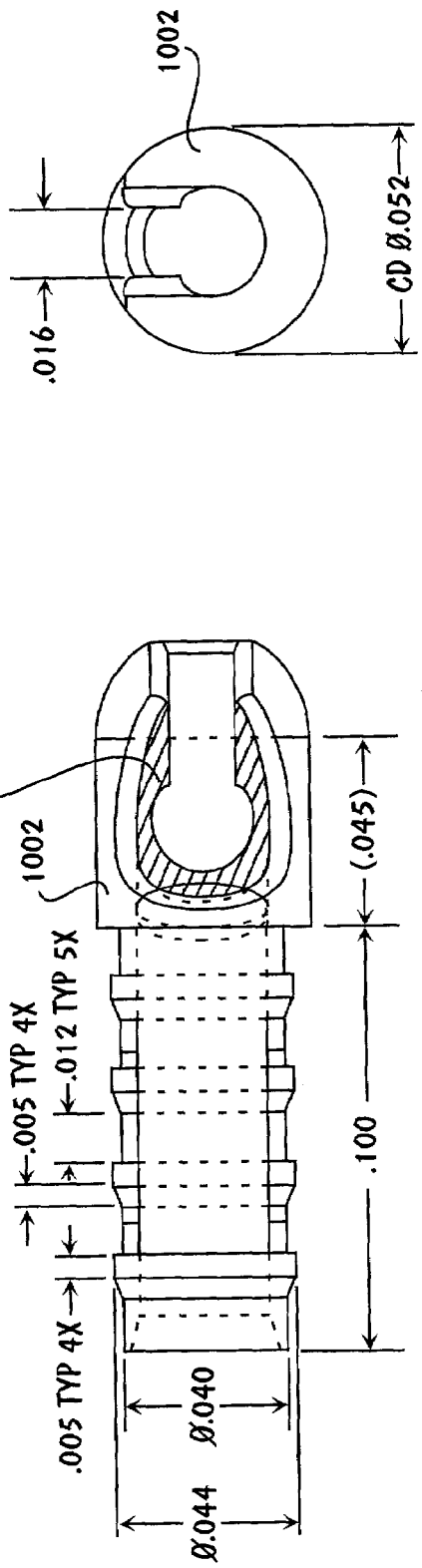
FIG. 10AA
FIG. 10AC
FIG. 10AB

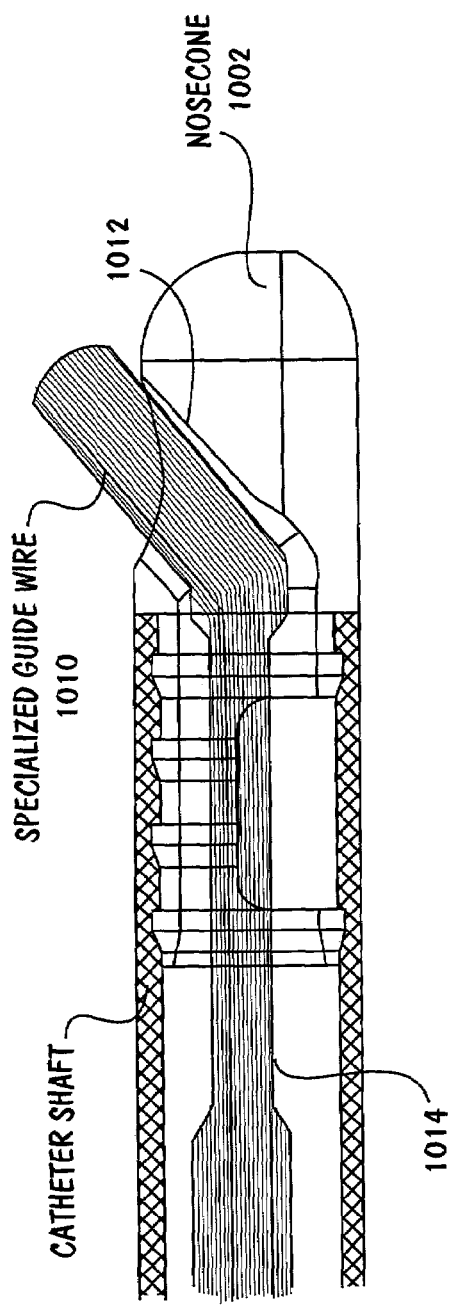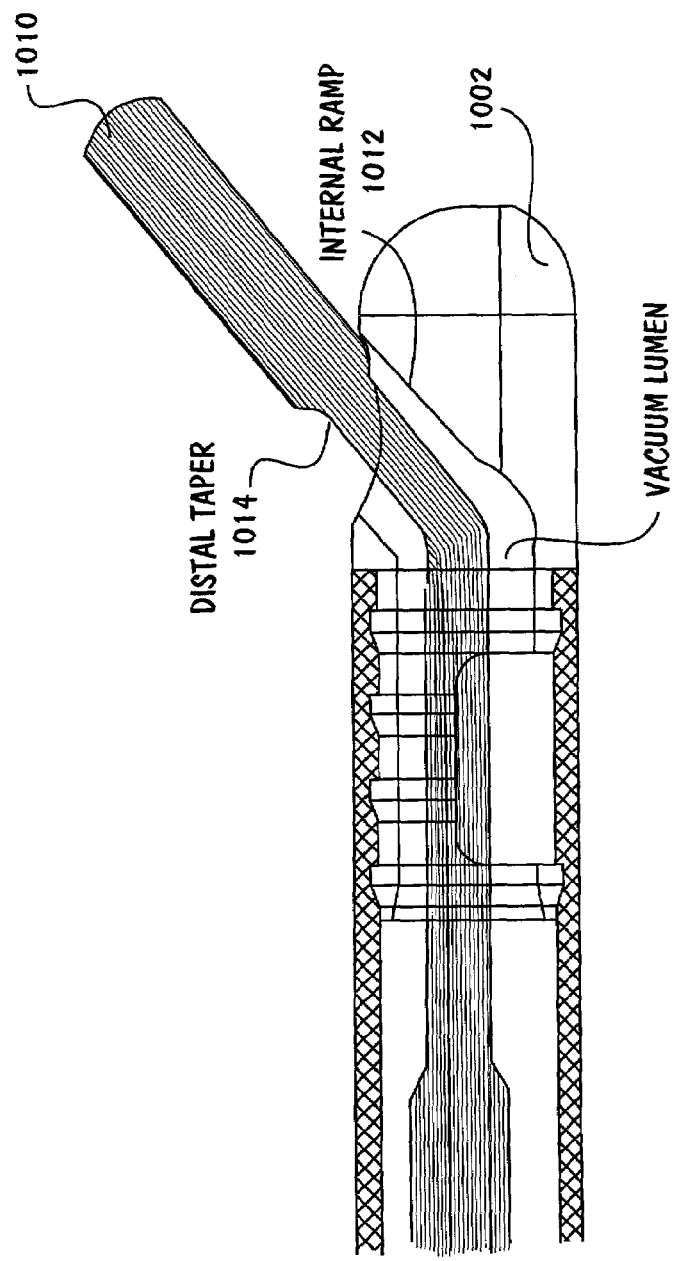

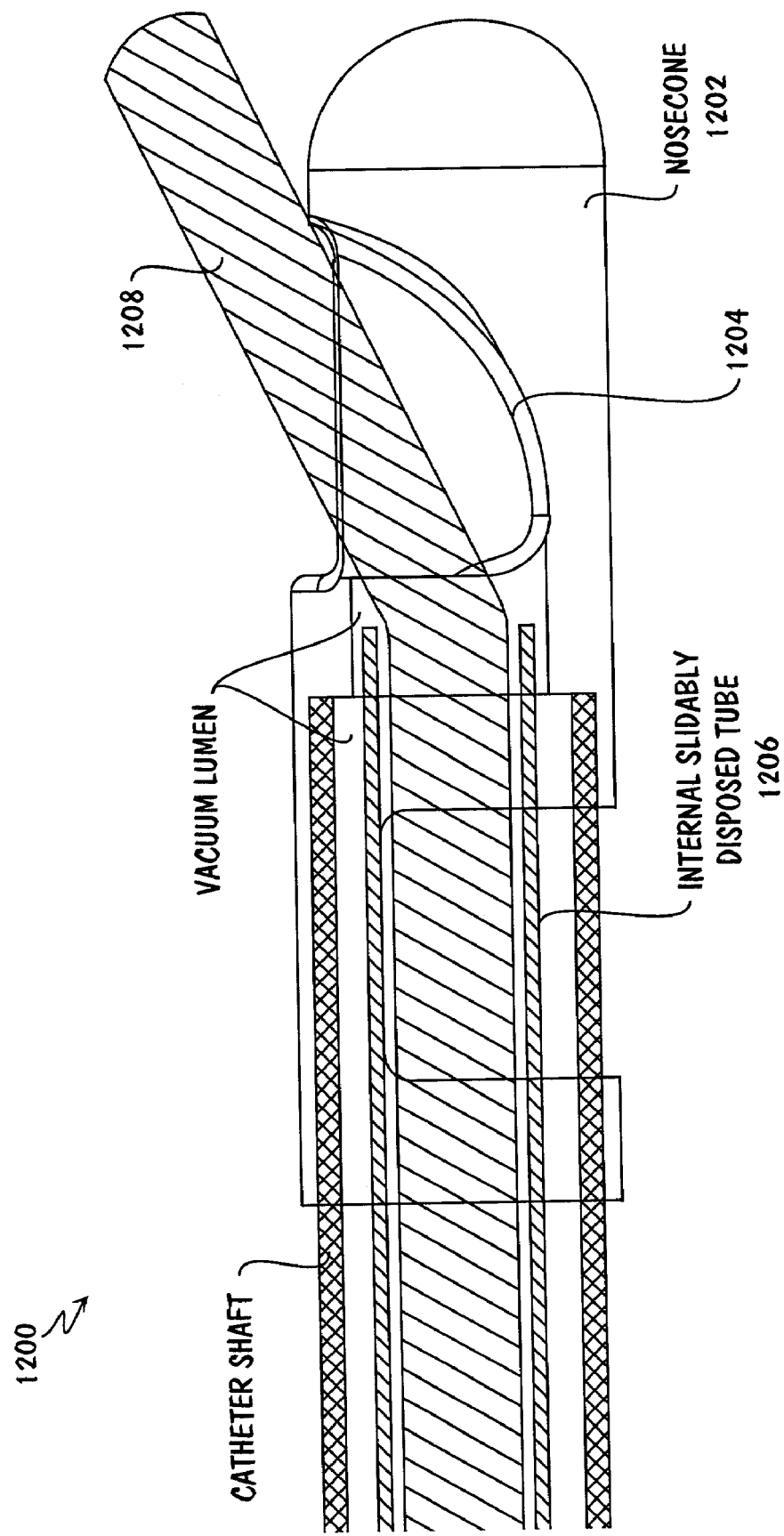

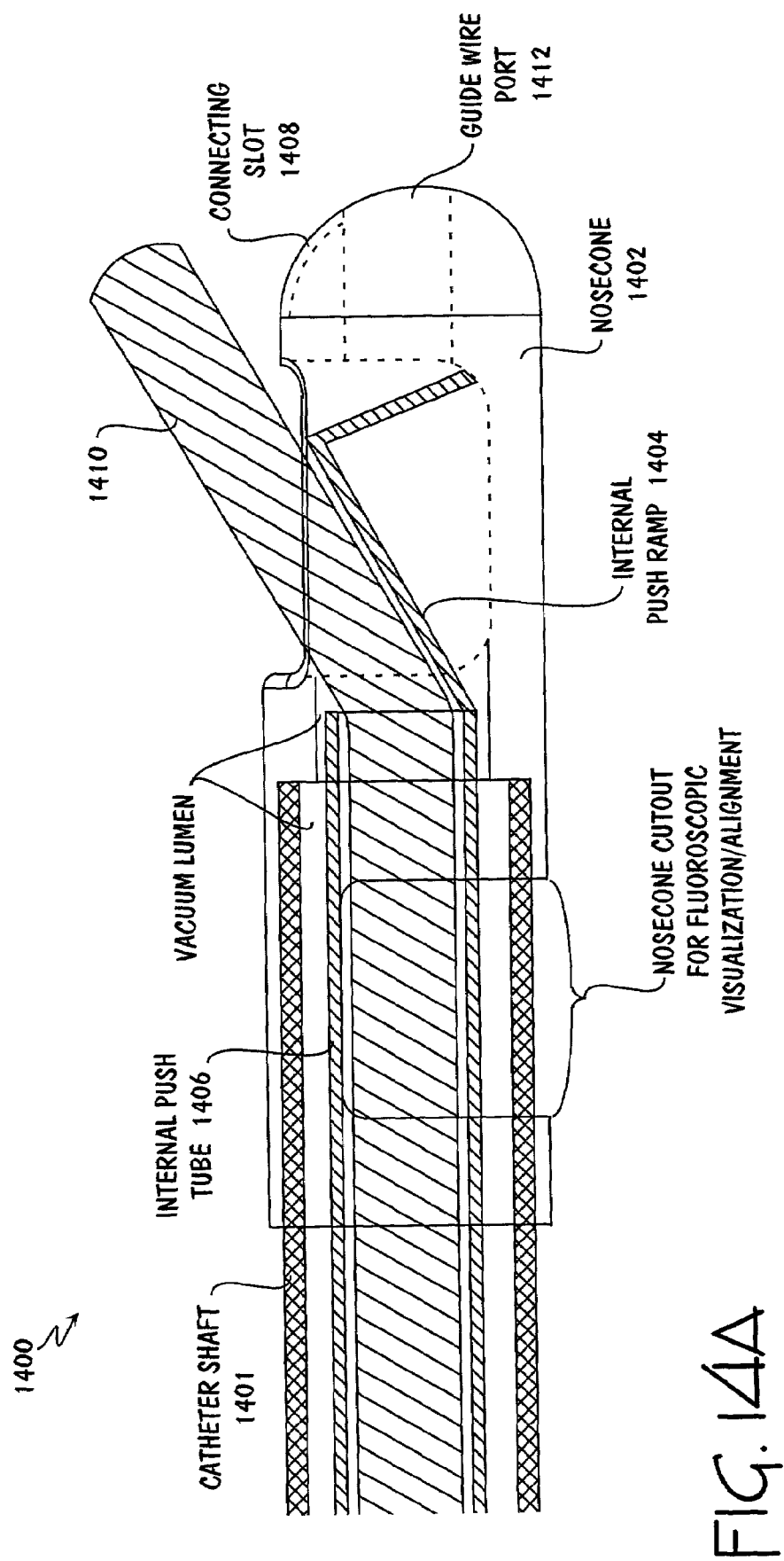

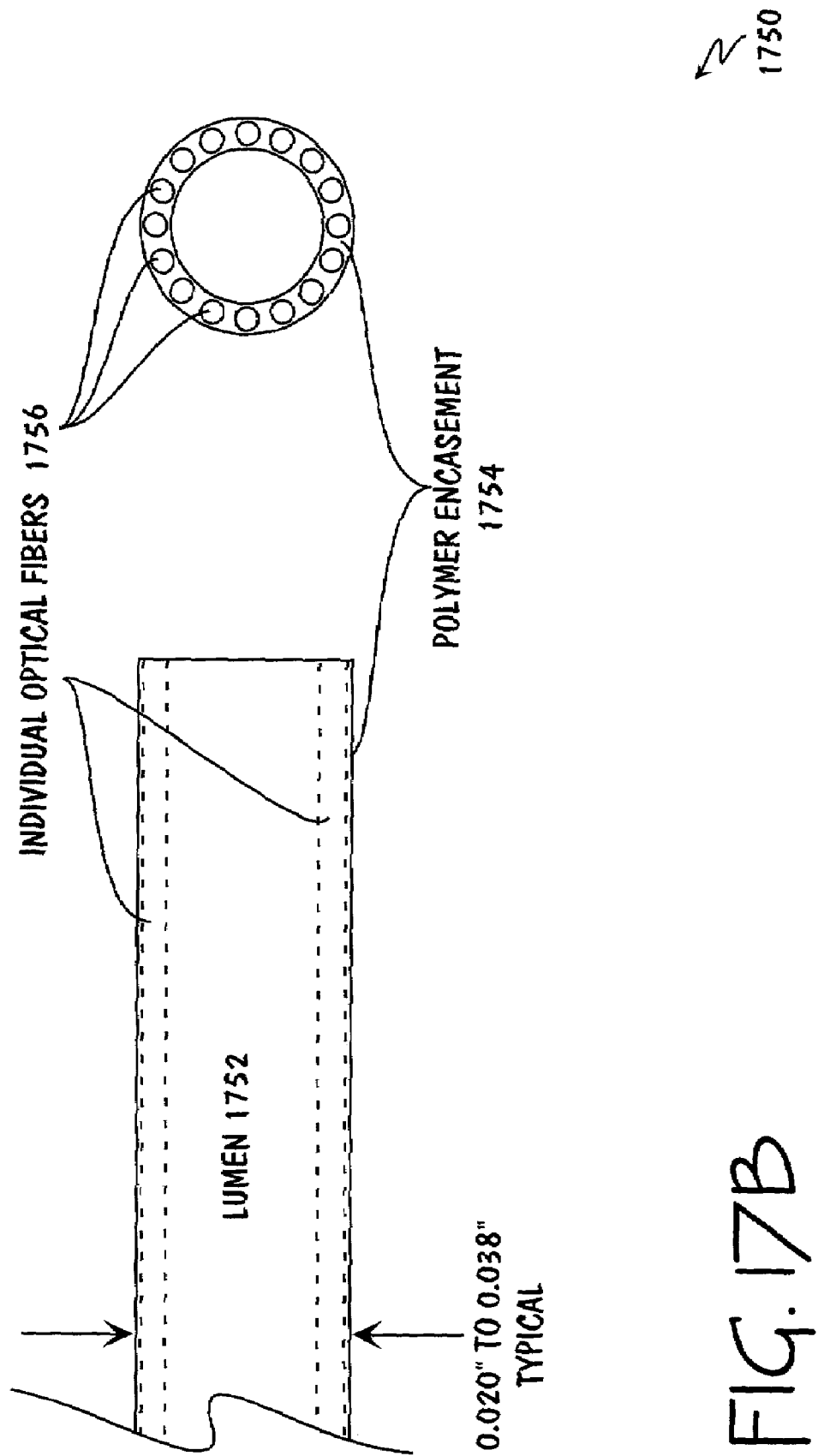

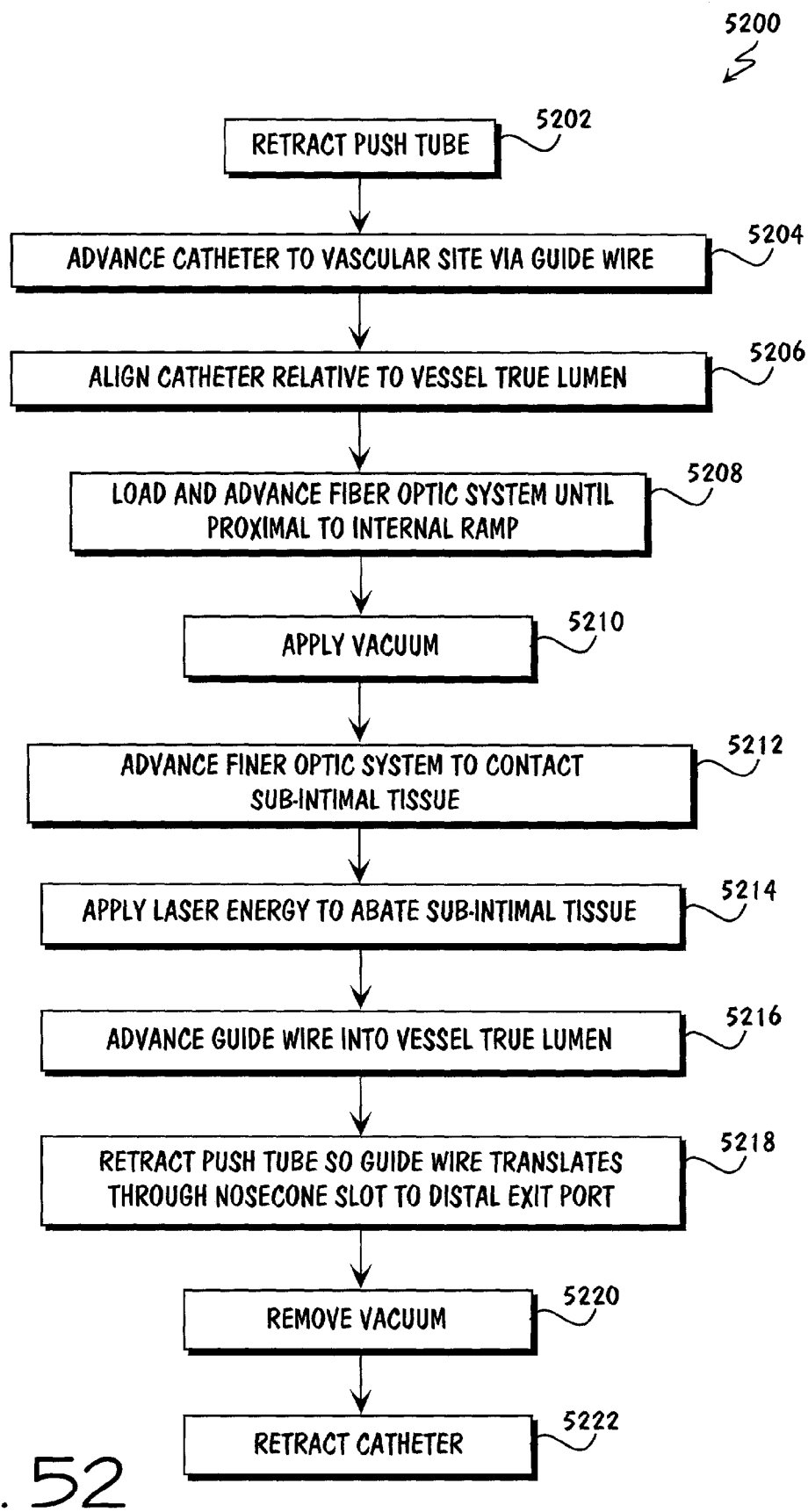

CATHETER SYSTEM FOR VASCULAR RE-ENTRY FROM A SUB-INTIMAL SPACE

RELATED APPLICATIONS

This application relates to and claims the benefit of the following U.S. Patent Application Nos. 60/251,756 filed Dec. 5, 2000; 60/255,729 filed Dec. 14, 2000; 60/263,350, 60/263,397, 60/263,579, 60/263,580, and 60/263,589, all filed Jan. 22, 2001; 60/268,263 filed Feb. 12, 2001; No. 60/301,537 filed Jun. 27, 2001; and 60/329,936 filed Oct. 17, 2001; all of which are incorporated herein by reference in their entirety.

TECHNICAL FIELD

The disclosed embodiments relate to catheter systems for crossing vascular occlusions.

BACKGROUND

An interventional guide wire or other interventional device is often used in medical procedures that attempt to establish a pathway through a heavily stenosed or chronically occluded vessel. A chronically occluded vessel is referred to as containing a chronic total occlusion (CTO). During these procedures, the guide wire or device can only be of clinical benefit to establish vessel patency if it is advanced distally into the vessel true lumen.

At times during the process of advancing the guide wire or device through the stenosed vessel or CTO, and beyond the control of the operator, the guide wire or device may inadvertently enter into the wall of the vessel itself, i.e. the sub-intimal plane or space, or dissection plane. Once in this sub-intimal plane, it becomes difficult to navigate the guide wire or device through the sub-intimal tissue to re-gain access into the vessel true lumen at points distal to the occlusion. The layer of tissue that separates the vessel true lumen from the sub-intimal plane is typically in the range from 100 to 500 micrometers for vessels in the diameter range from 2 mm to 4 mm, and from 100 to 3000 microns, in the largest vessels of the body. The composition of the tissue may be such that no guide wire or interventional device currently on the market can re-access the true lumen.

BRIEF DESCRIPTION OF THE FIGURES

FIG. 9AA is a catheter system including a nosecone with an internal ramp to guide an internal cannula element or laser for re-entry, under an embodiment.

FIG. 9AB is a top view of the catheter system of FIG. 9AA.

FIG. 9AC is a front view of the catheter system of FIG. 9AA.

FIG. 9E is a catheter system following retraction of a re-entry element with the cannula maintained in the vessel true lumen, under the embodiment of FIGS. 9AA–9AC.

FIG. 9F is a catheter system with a guide wire advanced into a vessel true lumen, under the embodiment of FIGS. 9AA–9AC.

FIG. 10AA is a catheter system including a nosecone with an internal ramp to guide a specialized guide wire for re-entry, under an alternative embodiment of FIGS. 9AA–9AC and 9B.

FIG. 10AB is a top view of the catheter system of FIG. 10AA.

FIG. 10AC is a front view of the catheter system of FIG. 10AA.

FIG. 10B is a catheter system including a nosecone, under the embodiment of FIGS. 10AA–10AC, showing a specialized guide wire deploying from the internal ramp.

FIG. 10C is a catheter system including a nosecone, under the embodiment of FIGS. 10AA–10AC, showing a distal taper of the specialized guide wire deploying from the internal ramp.

FIG. 12A is a catheter system including a nosecone with an internal ramp and an internal slidably disposed tube in a retracted position, under an embodiment, for use with a typical guide wire, specialized guide wires, RF systems, and optical fiber systems.

FIG. 14A is a catheter system of an embodiment including a nosecone with an internal slidably disposed push ramp for guiding typical guide wires, specialized guide wires, optical fiber systems, and RF systems.

FIG. 17B is an optical fiber system including a lumen, under an alternative embodiment of FIG. 17A.

FIG. 52 is a flow diagram for establishing a path into a vessel true lumen using laser energy, under a sixth alternative embodiment.

Figure 1:
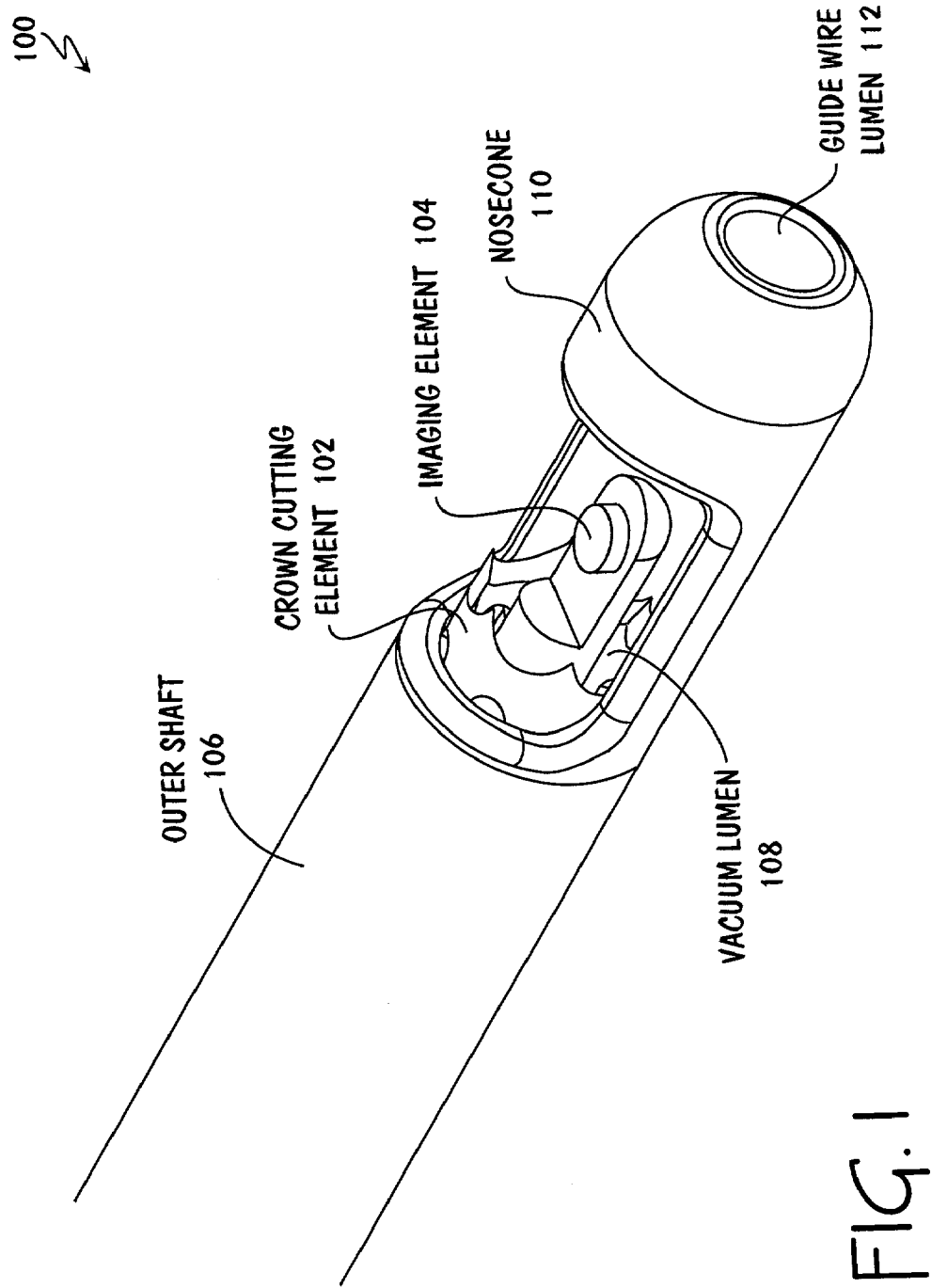
FIG. 1 is a catheter system of an embodiment including a rotational cutting element for re-entry and an imaging element for visualization.

In the drawings, the same reference numbers identify identical or substantially similar elements or acts. To easily identify the discussion of any particular element or act, the most significant digit or digits in a reference number refer to the Figure number in which that element is first introduced (e.g., element 902 is first introduced and discussed with respect to FIG. 9).

Figure numbers followed by the letters "A," "B," "C," etc. indicate either (1) that two or more Figures together form a complete Figure (e.g., FIGS. 50A and 50B together form a single, complete FIG. 50), but are split between two or more Figures because of paper size restrictions, amount of viewable area within a computer screen window, etc., or (2) that two or more Figures represent alternative embodiments or methods under aspects of the invention.

Unless described otherwise below, the construction and operation of the various blocks and components shown in the figures are of conventional design. As a result, such blocks need not be described in further detail herein, because they will be understood by those skilled in the relevant art. Such further detail is omitted for brevity and so as not to obscure the detailed description of the invention. Any modifications necessary to the blocks or components in the figures can be readily made by one skilled in the relevant art based on the detailed description provided herein.

The headings provided herein are for convenience only and do not necessarily affect the scope or meaning of the claimed invention.

DETAILED DESCRIPTION OF THE ILLUSTRATED EMBODIMENTS

A catheter-based system, or catheter system, is described for the purpose of gaining access to the true lumen of a blood vessel (coronary or peripheral artery or vein) from a space within the vessel wall itself, referred to herein as a sub-intimal plane, or dissection plane. Throughout this document, the various catheter embodiments are referred to as the re-entry catheter or catheter system.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of the embodiments of the invention.

Unless described otherwise herein, the embodiments described herein are well known or described in detail in the above-noted and cross-referenced provisional patent applications. Indeed, much of the detailed description provided herein is explicitly disclosed in the provisional patent applications; most or all of the additional material of aspects of the invention will be recognized by those skilled in the relevant art as being inherent in the detailed description provided in such provisional patent applications, or well known to those skilled in the relevant art. Those skilled in the relevant art can implement aspects of the invention based on the detailed description provided in the provisional patent applications.

FIGS. 1 through 19 show numerous different embodiments of catheter systems or platforms and associated components. For each system, the different methods and steps described may be combined to construct unique embodiments. Note that the various combinations of methods and steps yield additional embodiments of the catheter system. It is understood by those skilled in the art that these additional combinations/embodiments are intuitive in view of the platforms presented herein. A description of the numerous embodiments now follows.

FIG. 1 is a catheter system 100 of an embodiment including a rotational cutting element 102 for re-entry and an imaging element 104 for visualization. In addition to the rotational or crown cutting element 102 and the imaging element 104, the catheter system 100 includes an outer shaft 106 that houses at least one vacuum lumen 108 or port. The outer shaft 106 couples to a nosecone 110 that includes a guide wire lumen 112. A typical outside diameter of the outer shaft/nosecone is approximately 0.060 inches, while that of the cutting element is approximately 0.045 inches and that of the imaging element is approximately 0.030 inches, but the embodiment is not so limited.

Figure 2:
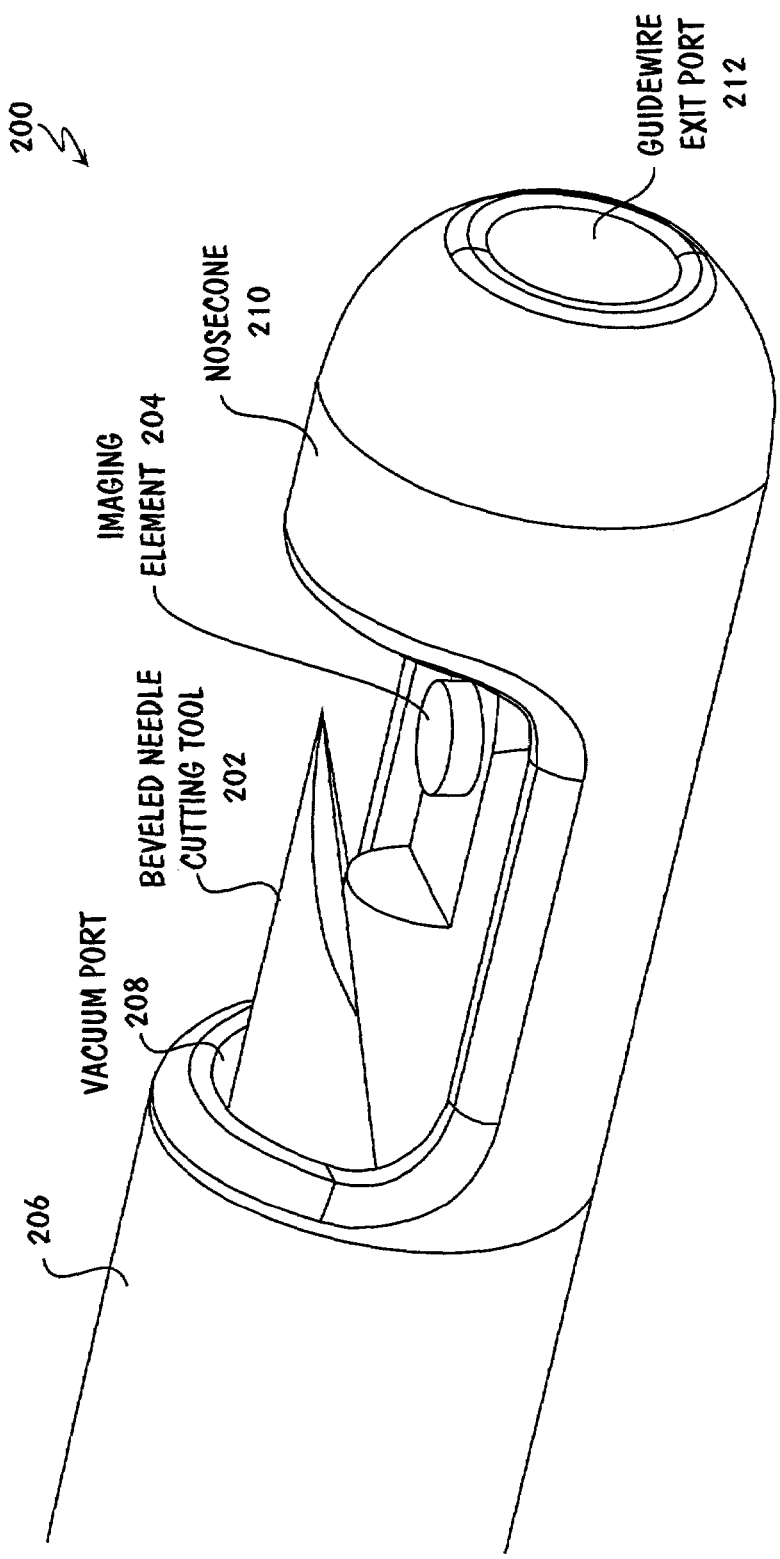
FIG. 2 is a catheter system including a forward cutting element for re-entry, under an alternative embodiment, and an imaging element for visualization.

FIG. 2 is a catheter system 200 including a forward cutting element 202 for re-entry, under an alternative embodiment, and an imaging element 204 for visualization. In addition to the forward or beveled needle cutting element 202 and the imaging element 204, the catheter system 200 includes an outer shaft 206 that houses at least one vacuum lumen 208 or port. The outer shaft 206 couples to a nosecone 210 that includes a guide wire lumen 212.

Figure 3:
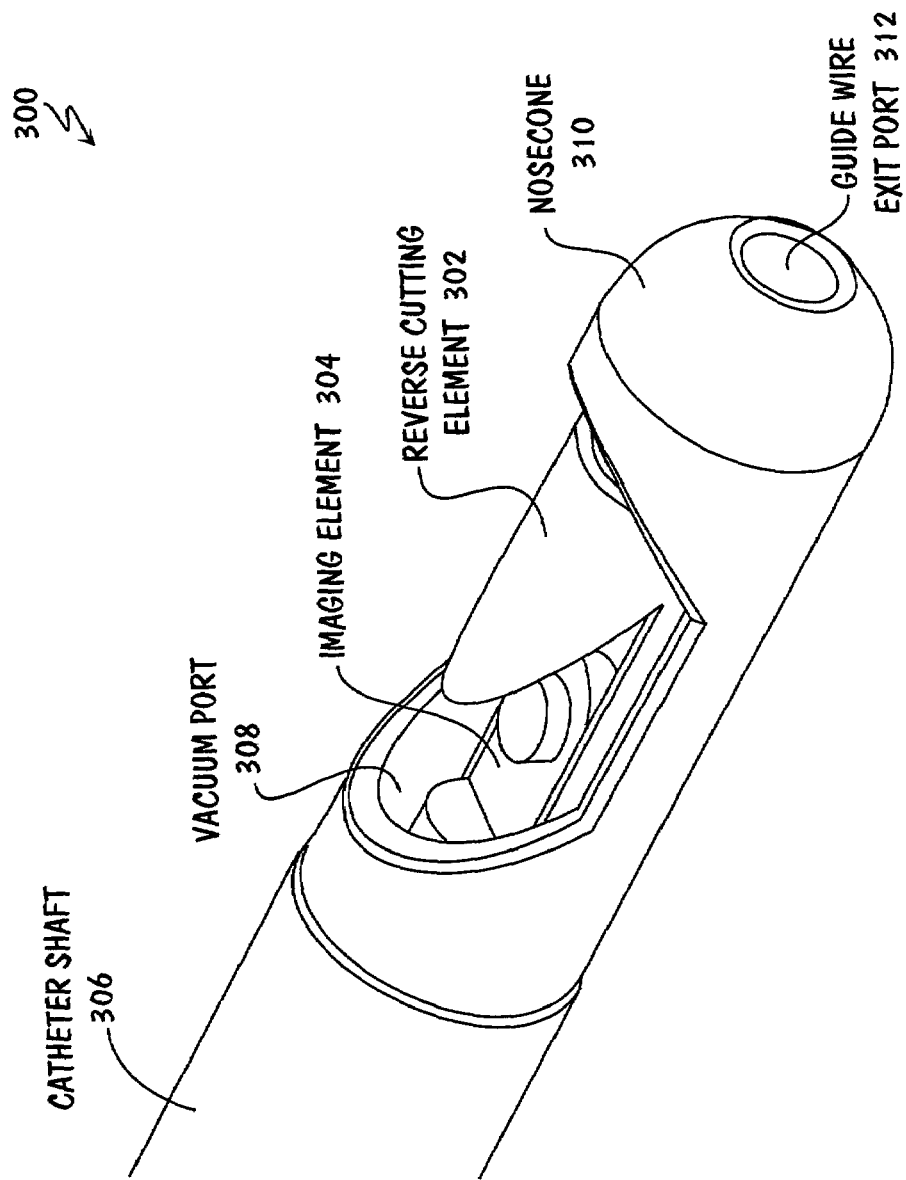
FIG. 3 is a catheter system including a reverse cutting element for re-entry, under yet another alternative embodiment, and an imaging element for visualization.

FIG. 3 is a catheter system 300 including a reverse cutting element 302 for re-entry, under yet another alternative embodiment, and an imaging element 304 for visualization. In addition to the reverse cutting element 302 and the imaging element 304, the catheter system 300 includes an outer shaft 306 that houses at least one vacuum lumen 308 or port. The outer shaft 306 couples to a nosecone 310 that includes a guide wire exit lumen 312.

Figure 4:
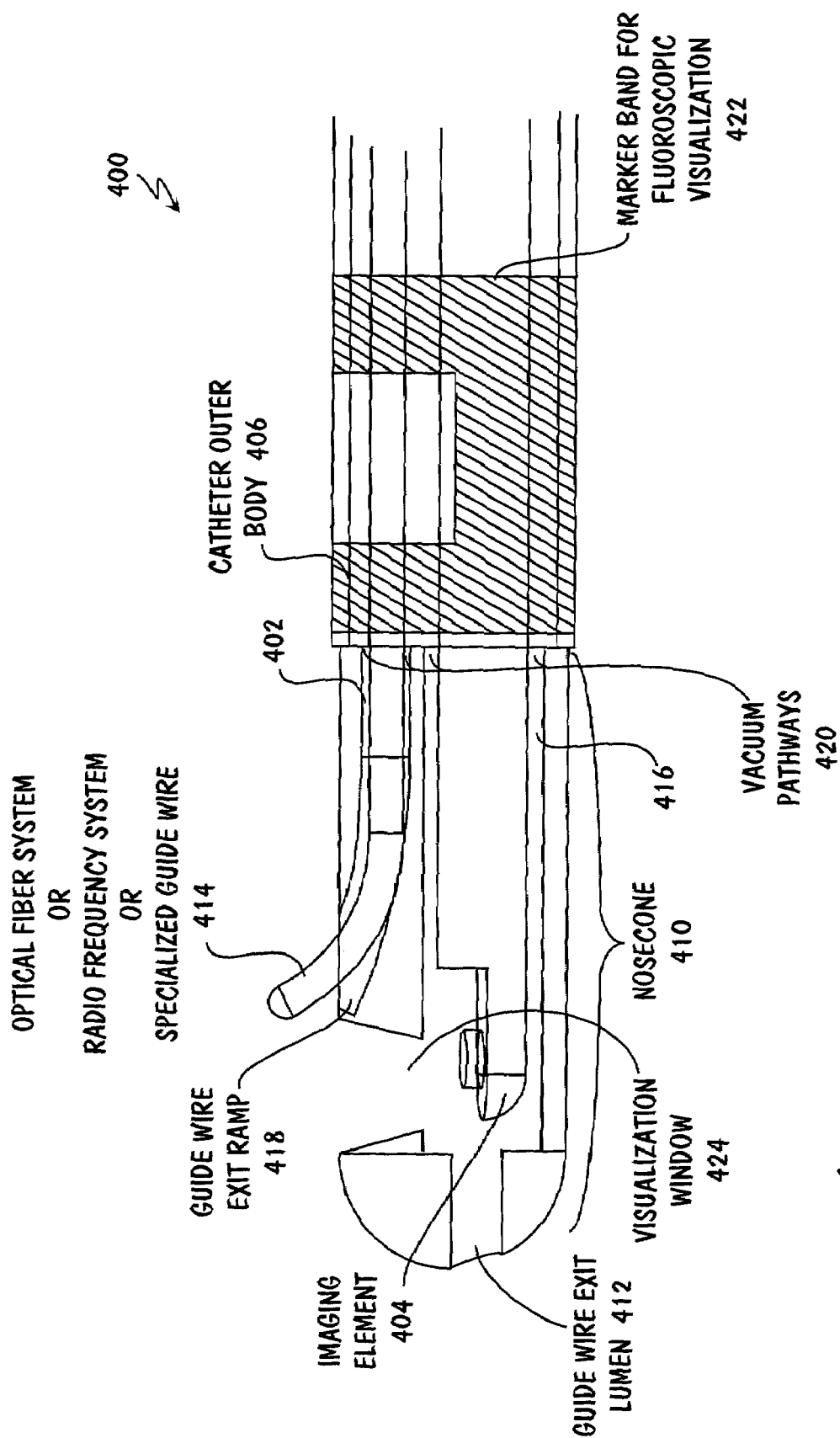
FIG. 4 is a catheter system including a lumen for receiving at least one of an optical fiber system, a radio frequency (RF) system, and a specialized guide wire, as another embodiment for re-entry, and an imaging element for visualization.

FIG. 4 is a catheter system 400 including at least one lumen 402 for receiving re-entry working elements 414 including optical fiber systems, rotational Intra-Vascular Ultrasound (IVUS) systems including those having a specialized distal tip, radio frequency (RF) systems, and specialized guide wires. The catheter system 400 includes a nosecone 410 coupled to a catheter outer body 406. The catheter outer body 406 includes a marker band for fluoroscopic visualization 422.

The nosecone 410 includes the lumen 402 for receiving any of a variety of working elements 414. The lumen 402 for receiving working elements terminates with an exit ramp 418 and a lateral exit port.

The nosecone 410 also includes a lumen 416 for receiving working elements including an imaging element 404 and a guide wire (not shown), for example. A visualization window 424 is included for use with the imaging element 404. The lumens 402 and 416 may also serve as vacuum ports or pathways 420, but are not so limited. The nosecone 410 also includes a guide wire exit lumen 412 in a distal end.

Figure 5:
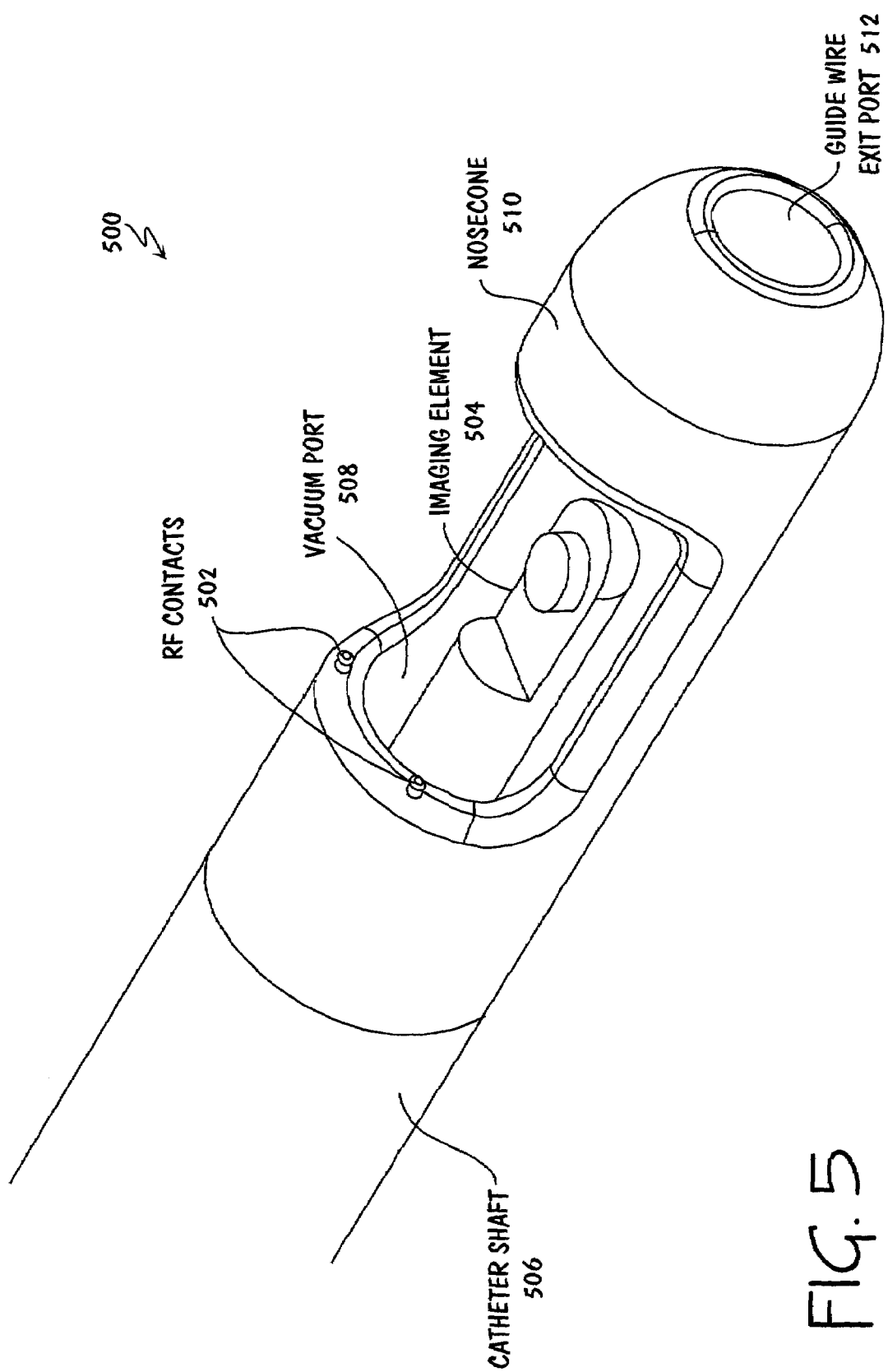
FIG. 5 is a catheter system embodiment including radio frequency (RF) electrodes or contacts for re-entry and an imaging element for visualization.

FIG. 5 is a catheter system embodiment 500 including radio frequency (RF) electrodes or contacts 502 for re-entry and an imaging element 504 for visualization. In addition to the RF electrodes 502 and the imaging element 504, the catheter system 500 includes an outer shaft 506 that houses at least one vacuum lumen 508 or port. The outer shaft 506 couples to a nosecone 510 that includes a distal guide wire exit lumen 512.

Figure 6:
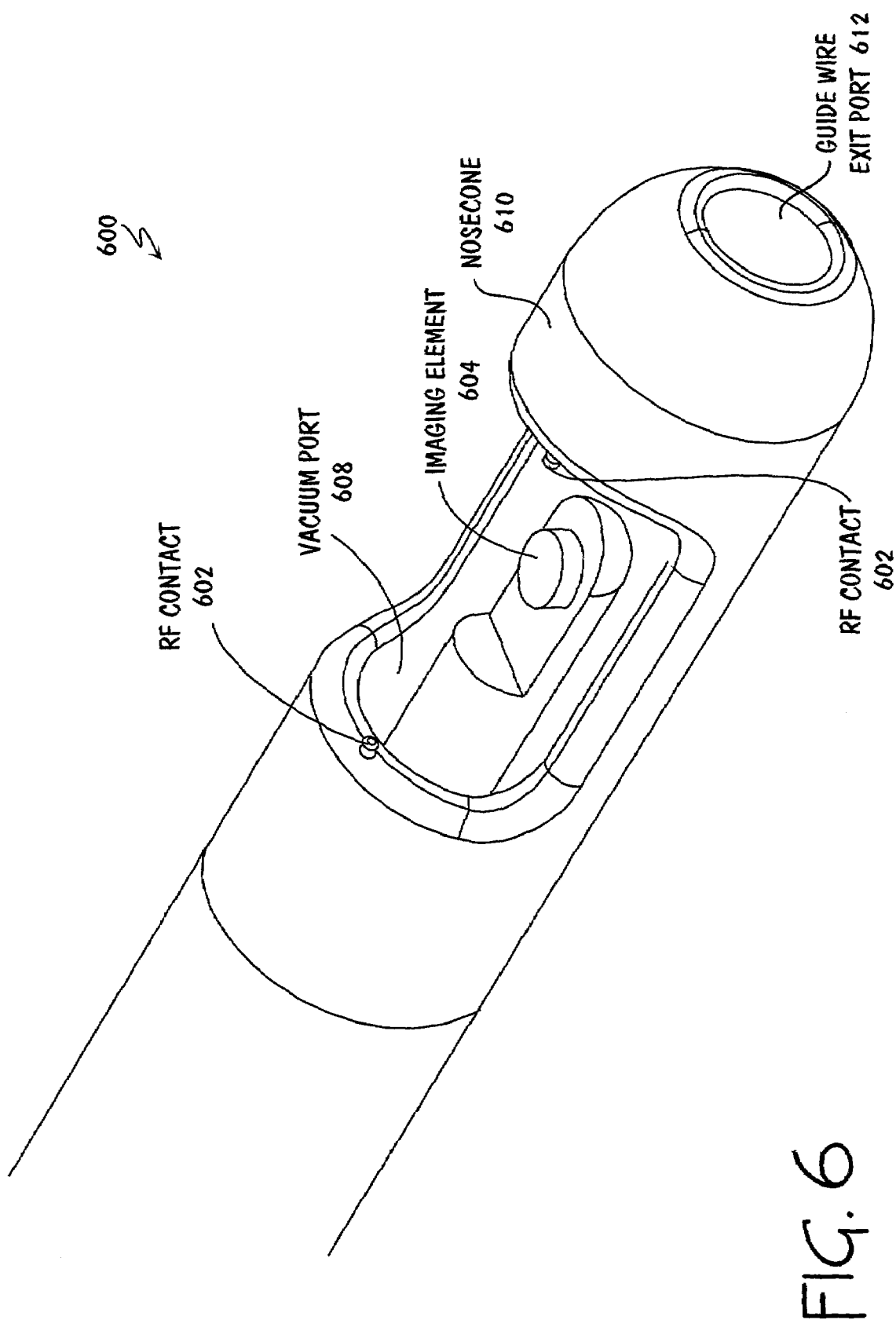
FIG. 6 is a catheter system embodiment including radio frequency (RF) electrodes or contacts of an alternative configuration for re-entry and an imaging element for visualization.

FIG. 6 is a catheter system embodiment 600 including radio frequency (RF) electrodes or contacts 602 of an alternative configuration. In addition to the opposing RF electrodes 602 the catheter system 600 includes an imaging element 604 and at least one vacuum lumen 608 or port. The nosecone 610 includes a distal guide wire exit lumen 612, but other embodiments may not include the exit lumen 612.

Figure 7A:
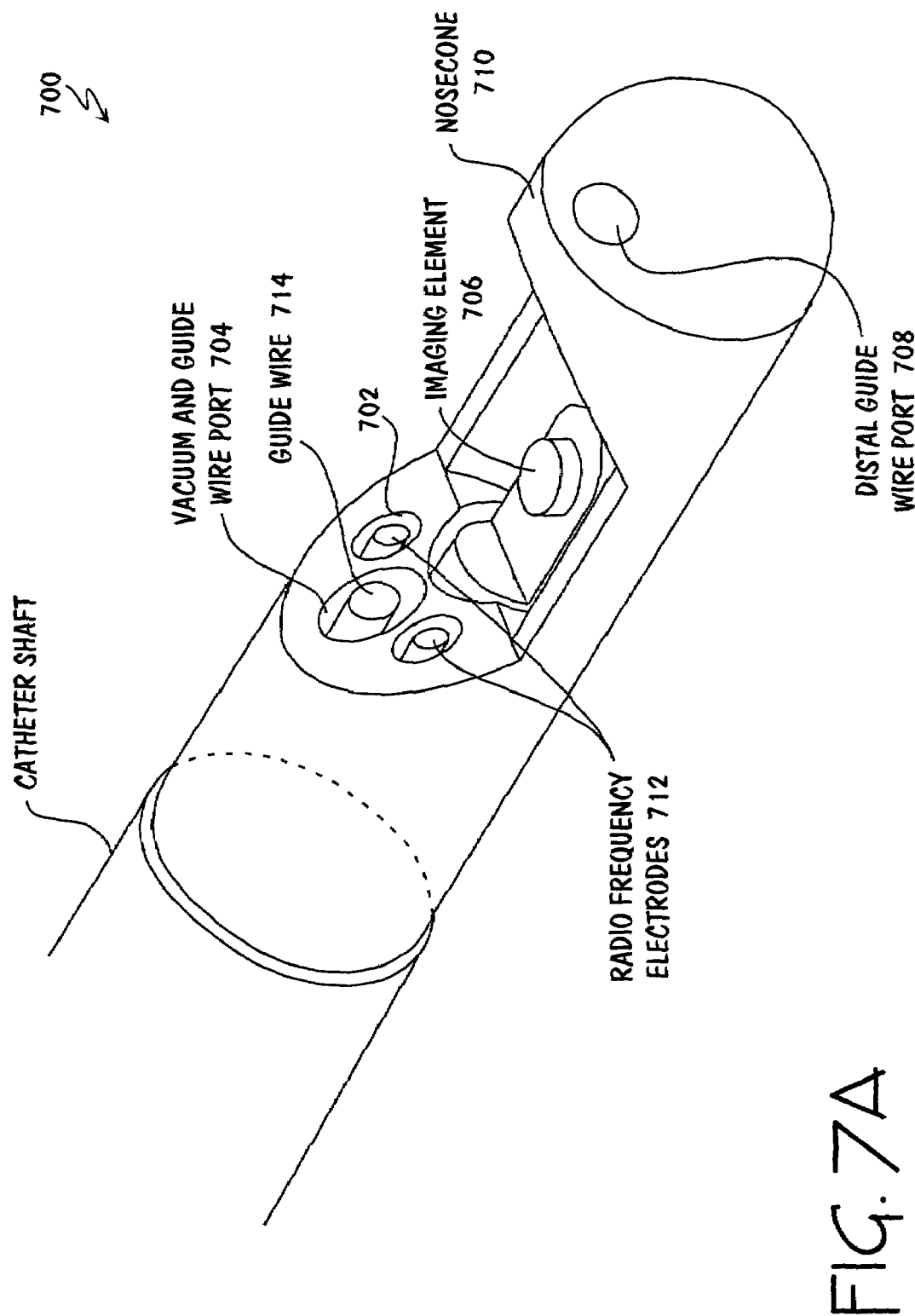
FIG. 7A is a catheter system embodiment including separate radio frequency (RF) electrode ports and vacuum/guide wire ports, along with an imaging element for visualization.

FIG. 7A is a catheter system embodiment 700 including a nosecone 710 having separate ports 702 that accept radio frequency (RF) electrodes 712 for vessel tissue ablation. Further, the nosecone 710 includes a vacuum and guide wire port 704, or vacuum port. The vacuum port 704, besides delivering vacuum to the nosecone, accepts working elements including, for example, a guide wire 714. The nosecone also includes an imaging element 706 and a distal guide wire port 708.

Figure 7B:
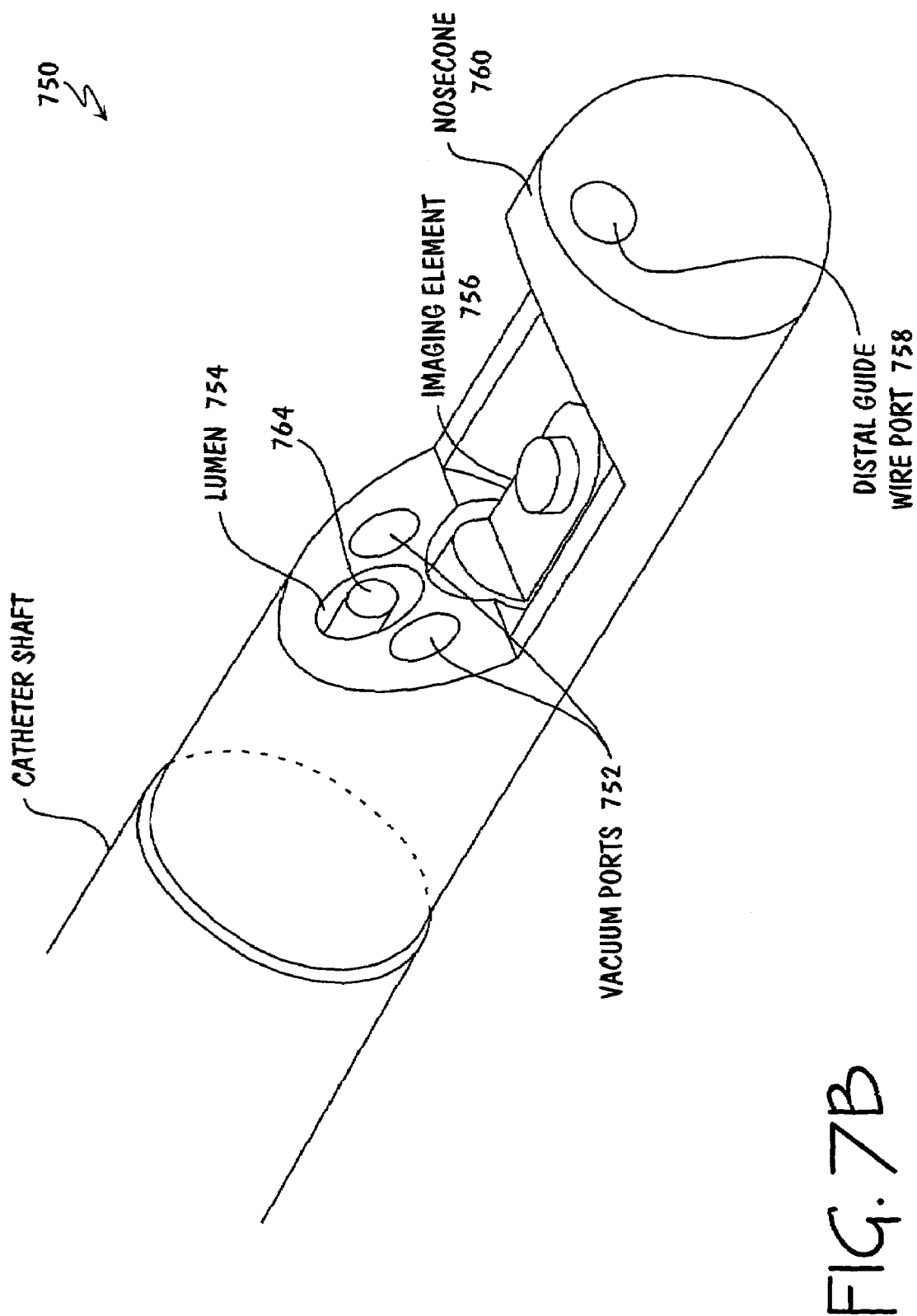
FIG. 7B is a catheter system embodiment including a lumen that accepts a fiber optic system or a guide wire, separate vacuum ports, and an imaging element for visualization.

FIG. 7B is a catheter system embodiment 750 including a nosecone 760 with a lumen 754 that accepts working elements 764 including guide wires and fiber optic tissue systems, for example fiber optic tissue ablation systems. Further, the nosecone 760 includes separate vacuum lumens or ports 752 that deliver vacuum to the nosecone. The nosecone also includes an imaging element 756 and a distal guide wire port 758.

Figure 8:
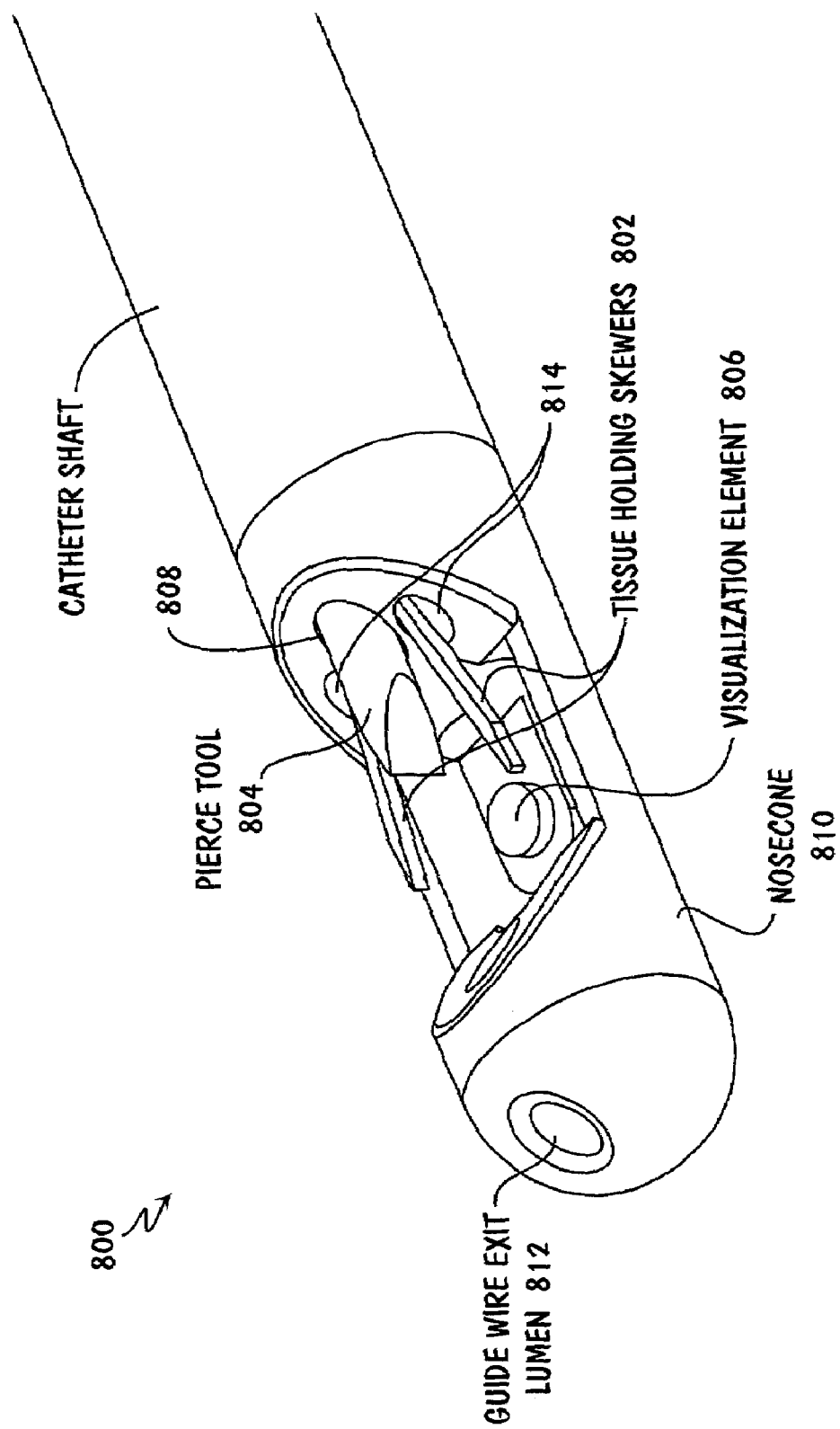
FIG. 8 is a catheter system of an embodiment including tissue-holding skewers, a re-entry element or pierce tool, and an imaging element for visualization.

FIG. 8 is a catheter system 800 of an embodiment having a nosecone 810 that accommodates tissue-holding skewers 802, a re-entry element or pierce tool 804, and an imaging element 806 for visualization. The lumen 808 carrying the pierce tool 804 can be used to support introduction of a guide wire (not shown). The nosecone 810 also includes a guide wire exit lumen 812. The lumens 814 that accept the tissue holding skewers 802 also provide vacuum to the nosecone 810.

FIGS. 9AA–9AC are a catheter system including a nosecone 902 with an internal ramp 904 to guide an internal cannula element and a re-entry laser system, under an embodiment. The nosecone 902 also includes a guide wire distal exit port 906, and a cutout 908 to guide fluoroscopic alignment. A side view 912, top view 914 and front view 916 of the nosecone 902 are shown.

Figure 9B:
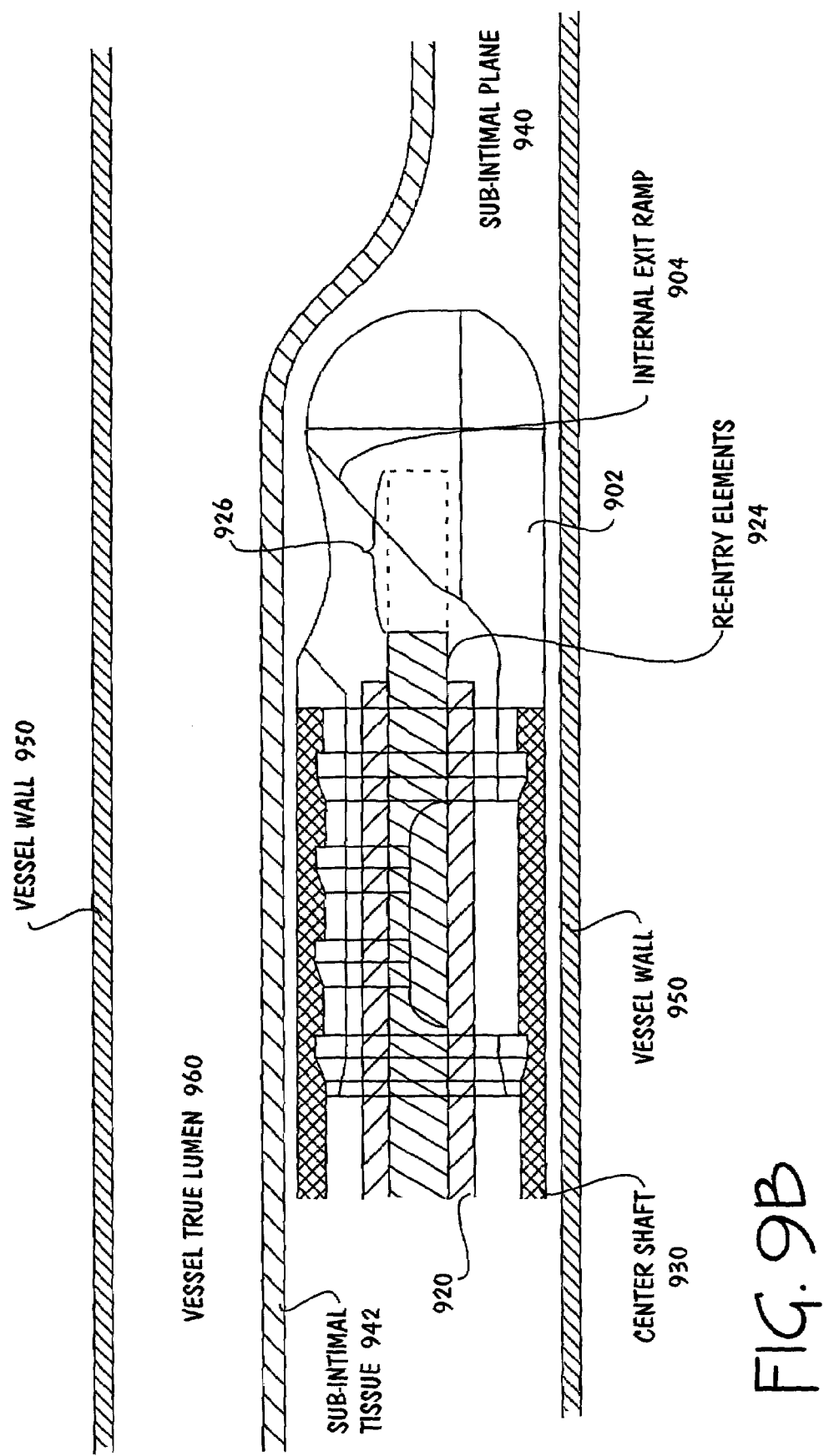
FIG. 9B is a catheter system in an initial position prior to cannula deployment, under the embodiment of FIGS. 9AA–9AC.

FIG. 9B is a catheter system in an initial position prior to cannula deployment, under the embodiment of FIG. 9A. The catheter shaft 930 and nosecone 902 is positioned within a sub-intimal plane 940 of the vessel wall 950. The cannula 920 is positioned in the catheter system at a position proximal to the exit ramp 904. The re-entry element 924 is advanced into the cannula 920. A variety of re-entry elements or devices 924 are deployable through the cannula 920, including typical guide wires, specialized guide wires (see FIG. 16 and the associated description herein), fiber optic systems (see FIGS. 17A and 17B and the associated description herein), RF electrode systems (see FIG. 18 and the associated description herein), and Intra-Vascular Ultrasound Systems (IVUS) (see FIG. 19 and the associated description herein). When the IVUS system is used for visualization, its visualization position 926 is shown. The catheter system of an embodiment also includes vacuum ports 922.

Figure 9C:
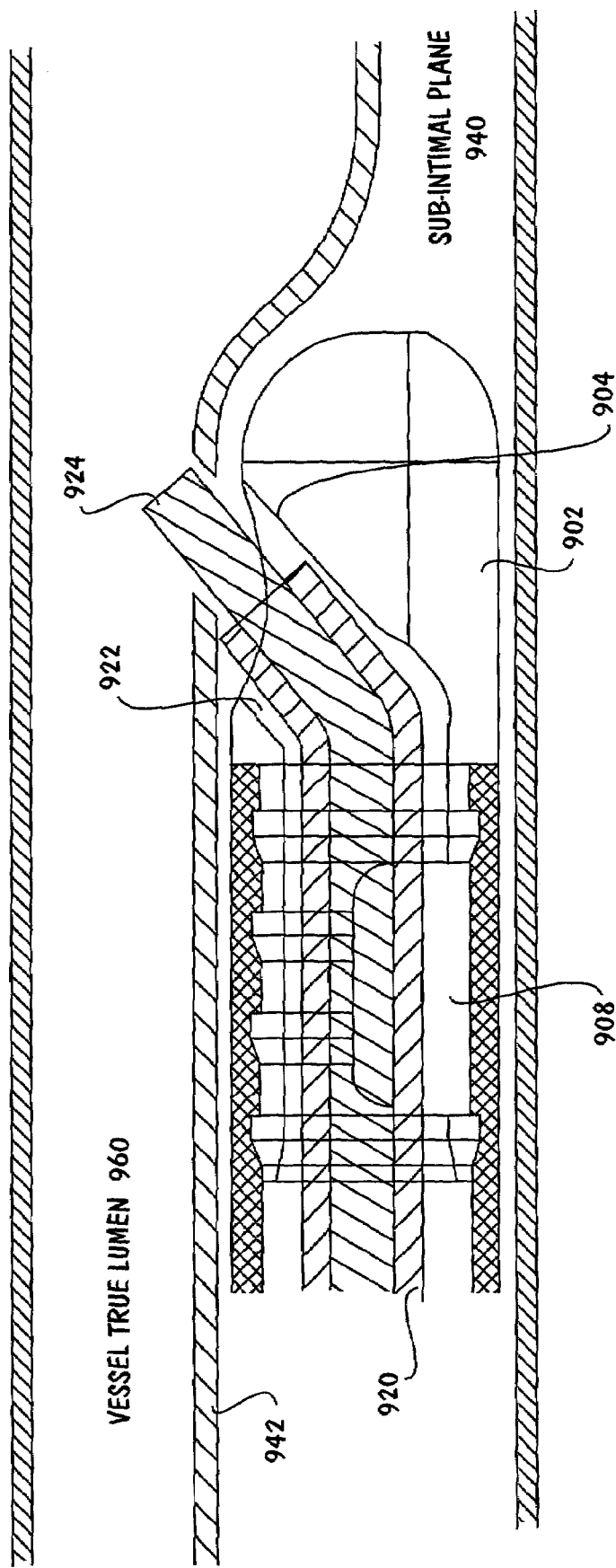
FIG. 9C is a catheter system with a cannula deployed and a re-entry element advanced across sub-intimal tissue, under the embodiment of FIGS. 9AA–9AC.
Figure 9D:
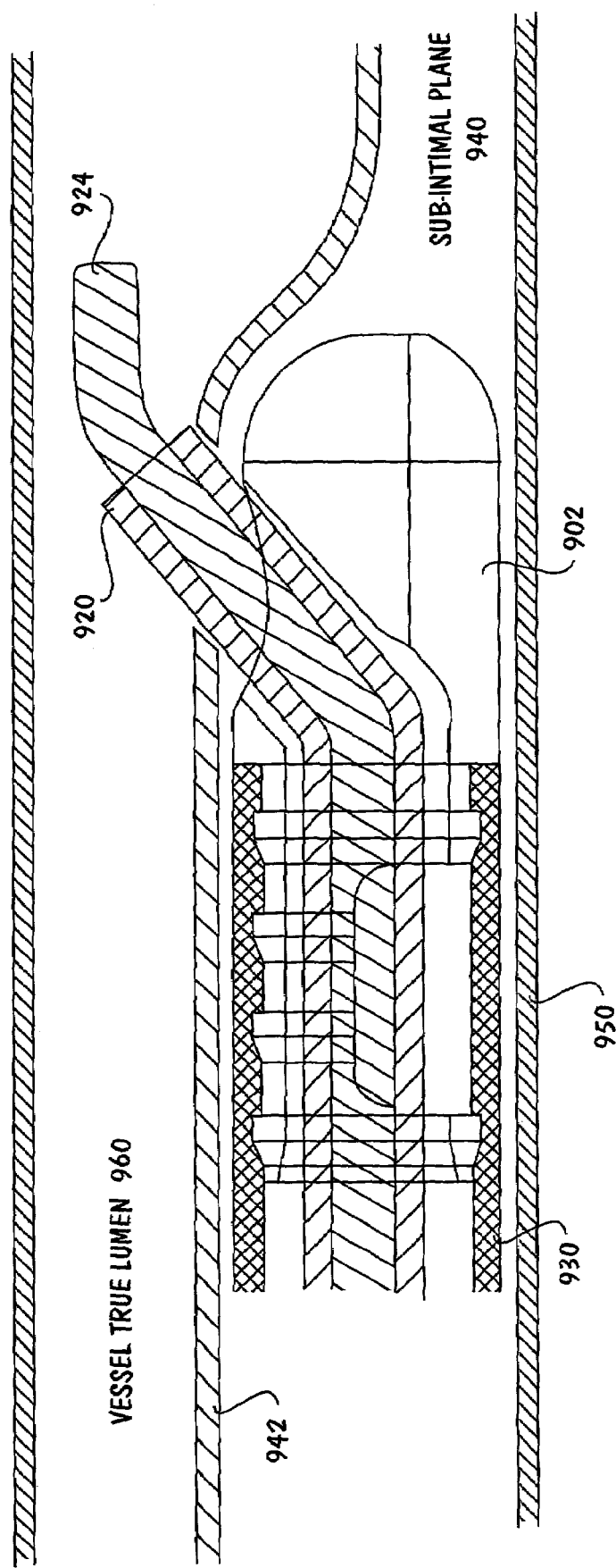
FIG. 9D is a catheter system with a cannula advanced into a vessel true lumen, under the embodiment of FIGS. 9AA–9AC.

FIG. 9C is a catheter system with the slidably disposed cannula 920 deployed from the nosecone 902 via the exit ramp 904. The re-entry element 924 advances across sub-intimal tissue 942, establishing a path into the vessel true lumen 960. FIG. 9D shows the cannula 920 advanced into the vessel true lumen 960. FIG. 9E is the catheter system following retraction of the re-entry element 924 with the cannula 920 maintained in the vessel true lumen 960, under the embodiment of FIG. 9A. FIG. 9F shows a guide wire 928 advanced into the vessel true lumen 960 through the cannula 920, following retraction of the re-entry element 924.

Figure 10D:
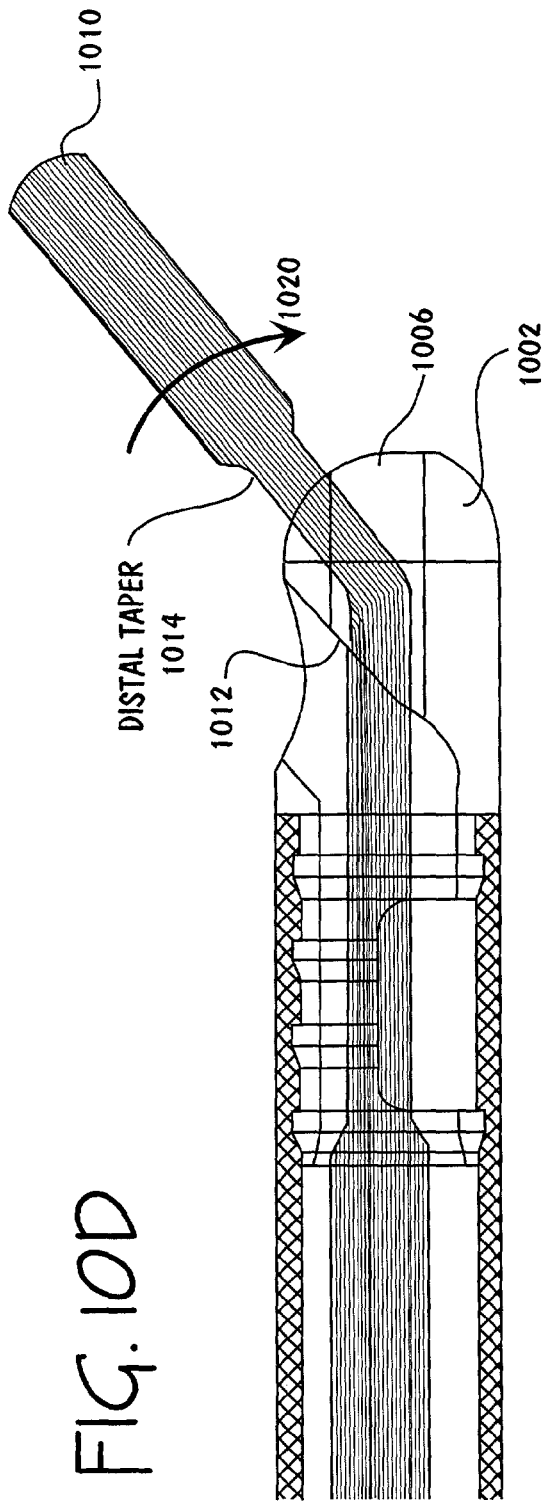
FIG. 10D is a catheter system including a nosecone, under the embodiment of FIGS. 10AA–10AC, showing the distal taper of the specialized guide wire repositioning from the internal ramp through the nosecone slot.

FIGS. 10AA–10AC are a catheter system including a nosecone 1002 with an internal ramp to guide a specialized guide wire for re-entry, under an alternative embodiment of FIGS. 9AA–9AC and 9B. The nosecone 1002 of this embodiment has a modified guide wire exit port 1006 to accommodate the specialized guide wire or a specialized cannula. FIGS. 10B–10E show deployment of the specialized guide wire.

Figure 10E:
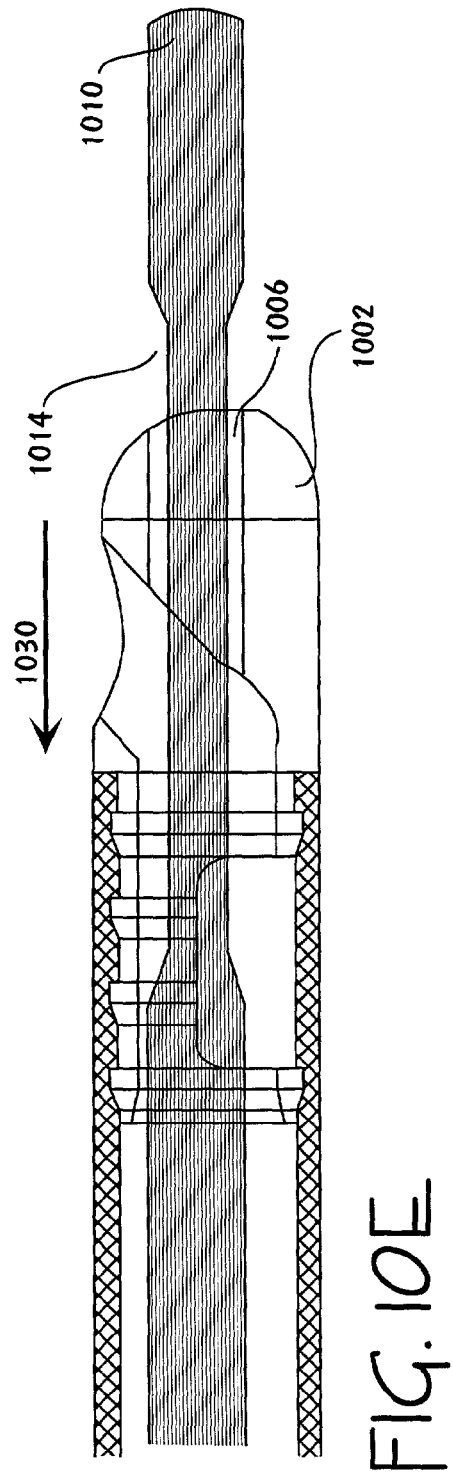
FIG. 10E is a catheter system including a nosecone, under the embodiment of FIGS. 10AA–10AC, showing catheter removal from a treatment site following deployment of the specialized guide wire using the nosecone.

FIG. 10B shows the specialized guide wire 1010 in an initial phase of deployment using the internal ramp 1012. The specialized guide wire 1010 of an embodiment includes at least one distal taper section 1014. FIG. 10C shows the specialized guide wire 1010 in a further state of deployment. FIG. 10D shows that the nosecone slot 1016 allows the specialized guide wire 1010 to translate or reposition 1020 into the guide wire exit port 1006 as the distal taper section 1014 of the specialized guide wire 1010 reaches the top of the exit ramp 1012. FIG. 10E shows that the nosecone 1002 and catheter system are retracted 1030 or removed from a treatment site following deployment of the specialized guide wire using the nosecone.

Figure 11:
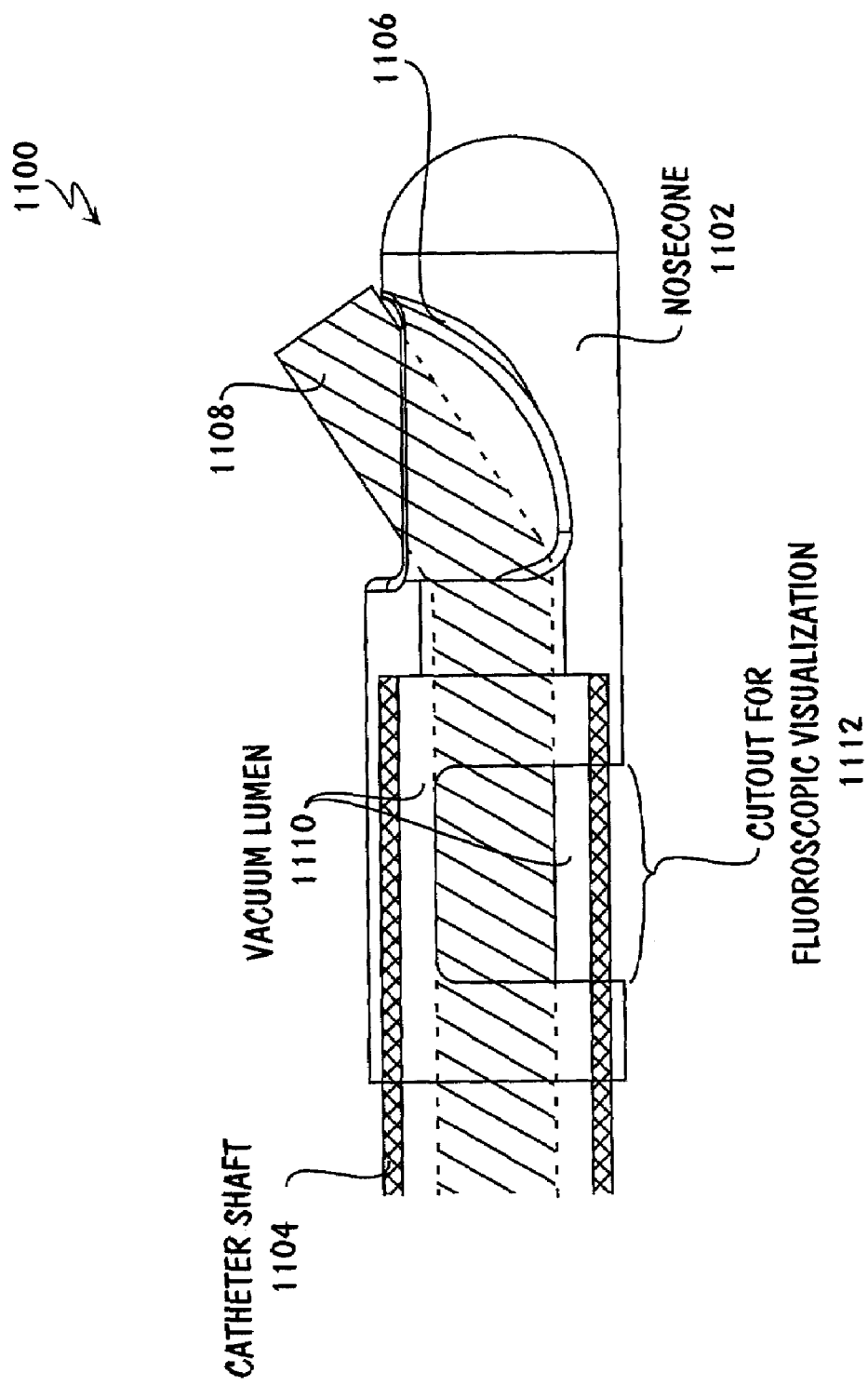
FIG. 11 is a catheter system including a nosecone with an internal ramp, under an embodiment, for use with a typical guide wire.

FIG. 11 is a catheter system 1100 including a nosecone 1102 coupled to a catheter shaft 1104. The nosecone 1102 includes an internal ramp 1106. A variety of working elements or devices 1108 are deployable using the internal ramp 1106, including typical guide wires, specialized guide wires (see FIG. 16 and the associated description herein), fiber optic systems (see FIGS. 17A and 17B and the associated description herein), RF system components (see FIG. 18 and the associated description herein), and IVUS (see FIG. 19). The catheter system 1100 further includes a vacuum lumen 1110 and at least one region 1112 housing fluoroscopic visualization elements.

Figure 12B:
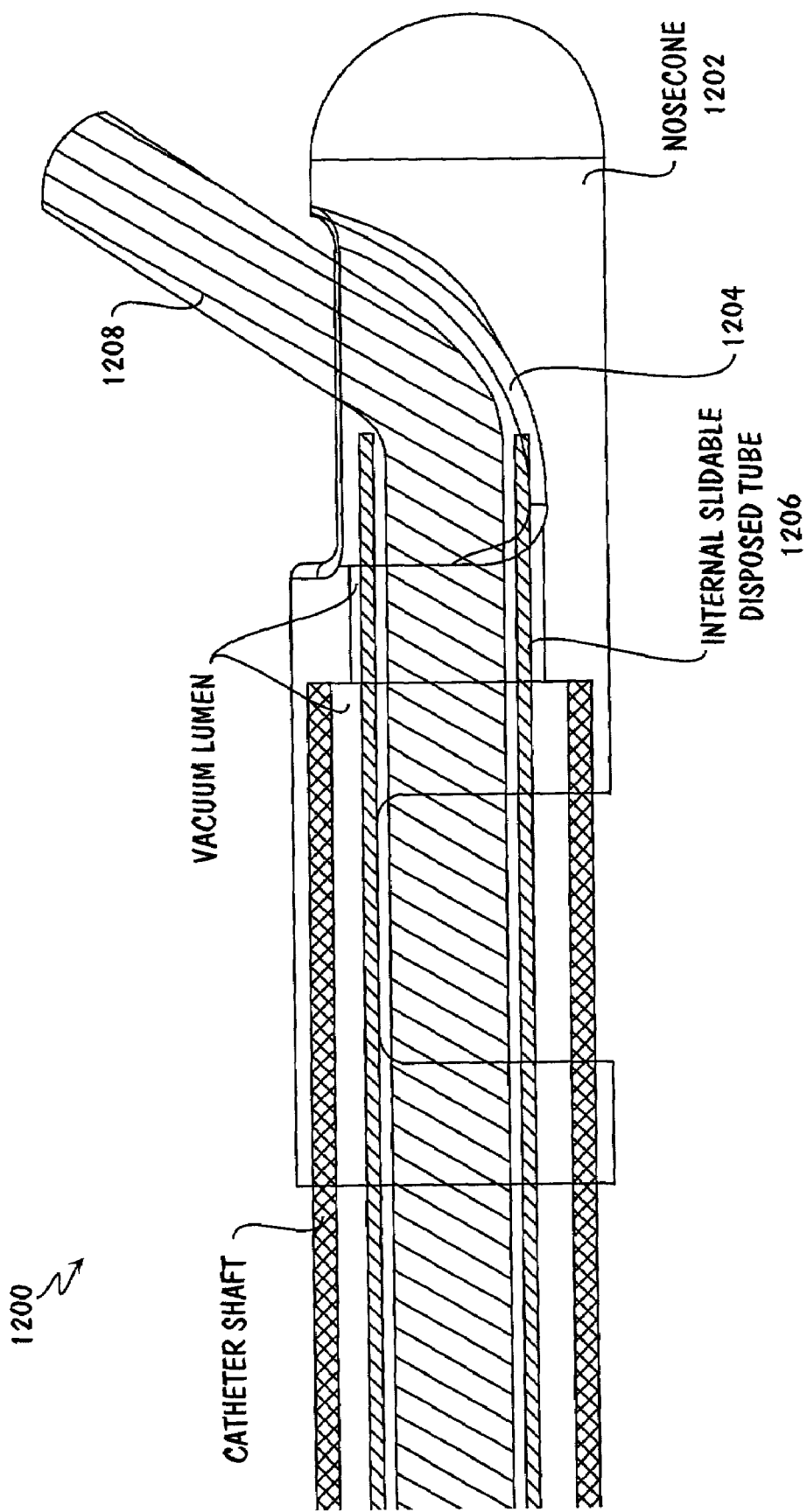
FIG. 12B is a catheter system including the nosecone with the internal ramp and internal slidably disposed tube, under the embodiment of FIG. 12A, where the internal slidably disposed tube is in an extended position.

FIG. 12A is a catheter system 1200 including a nosecone 1202 with an internal ramp 1204 and an internal slidably disposed tube 1206, under an alternative embodiment of FIGS. 9AA–9AC, 9B, and 10A–10E. The position of the internal tube 1206 is controllable to aid in steering a working element 1208 deployed via the catheter system 1200. When the internal tube 1206 is in this retracted position, the working element 1208 is deployed at a shallower deployment angle relative to a longitudinal axis of the catheter system 1200. FIG. 12B shows the catheter system 1200 when the internal tube 1206 is in an extended position. Extension of the internal tube 1206 results in deployment of the working element 1208 at deployment angles that are progressively more acute. A variety of working elements or devices 1208 are deployable using the internal ramp 1204, including typical guide wires, specialized guide wires (see FIG. 16 and the associated description herein), fiber optic systems (see FIGS. 17A and 17B and the associated description herein), RF system components (see FIG. 18 and the associated description herein), and IVUS (see FIG. 19 and the associated description herein).

Figure 13:
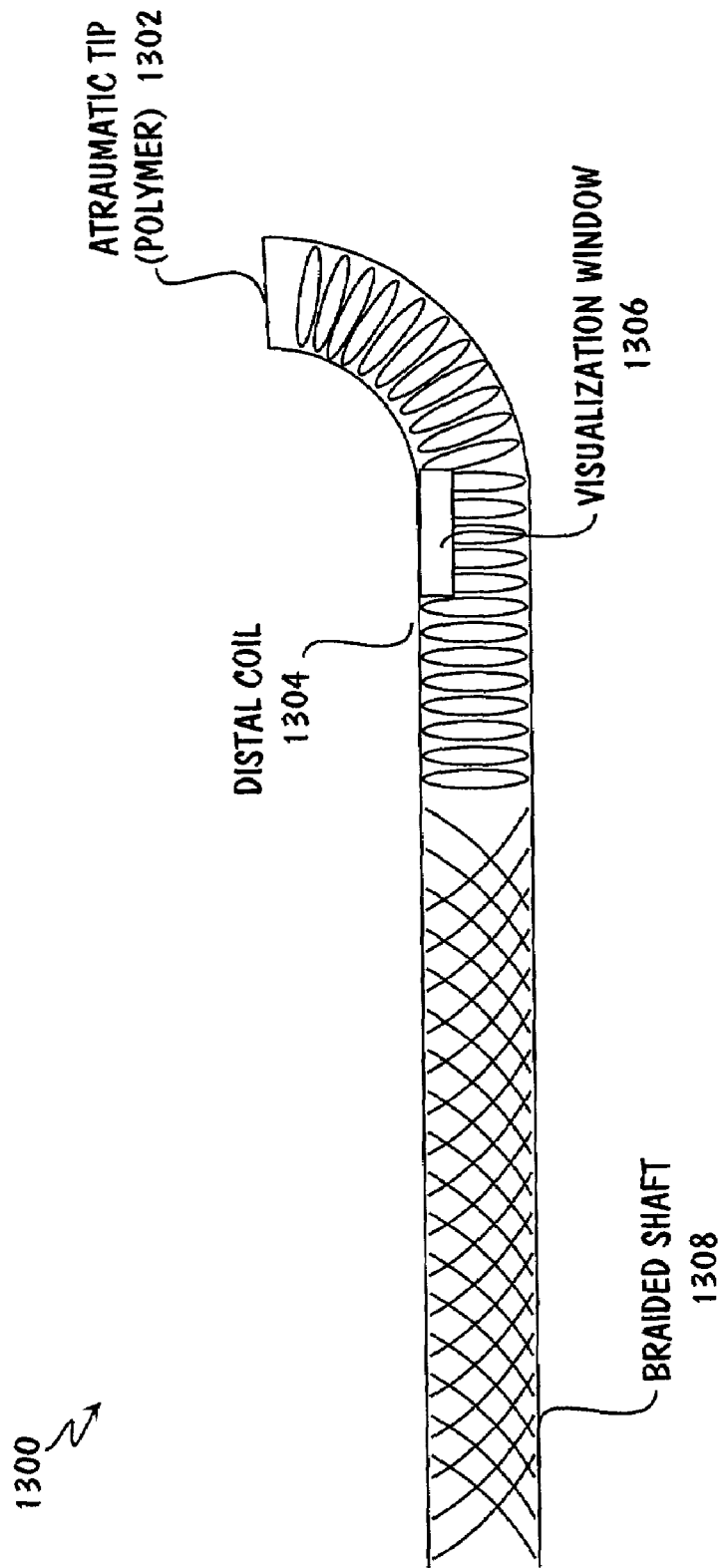
FIG. 13 is a catheter system including a curved distal catheter tip, under an embodiment, for guiding typical guide wires, specialized guide wires, optical fiber systems, and RF systems.

FIG. 13 is a catheter system 1300 including a curved distal catheter tip 1302, under an embodiment. The curved distal tip 1302 is coupled to a distal coil 1304 that, in one embodiment, is formed from platinum. The distal coil 1304 may include a visualization window 1306, but is not so limited. The distal coil 1304 couples to a braided catheter shaft 1308, but may be used with various types of catheter shafts known in the art. The catheter system 1300 can be used for guiding various working elements including typical guide wires, specialized guide wires, optical fiber systems (see FIGS. 17A and 17B and the associated description herein), and IVUS (see FIG. 19 and the associated description herein).

Figure 14B:
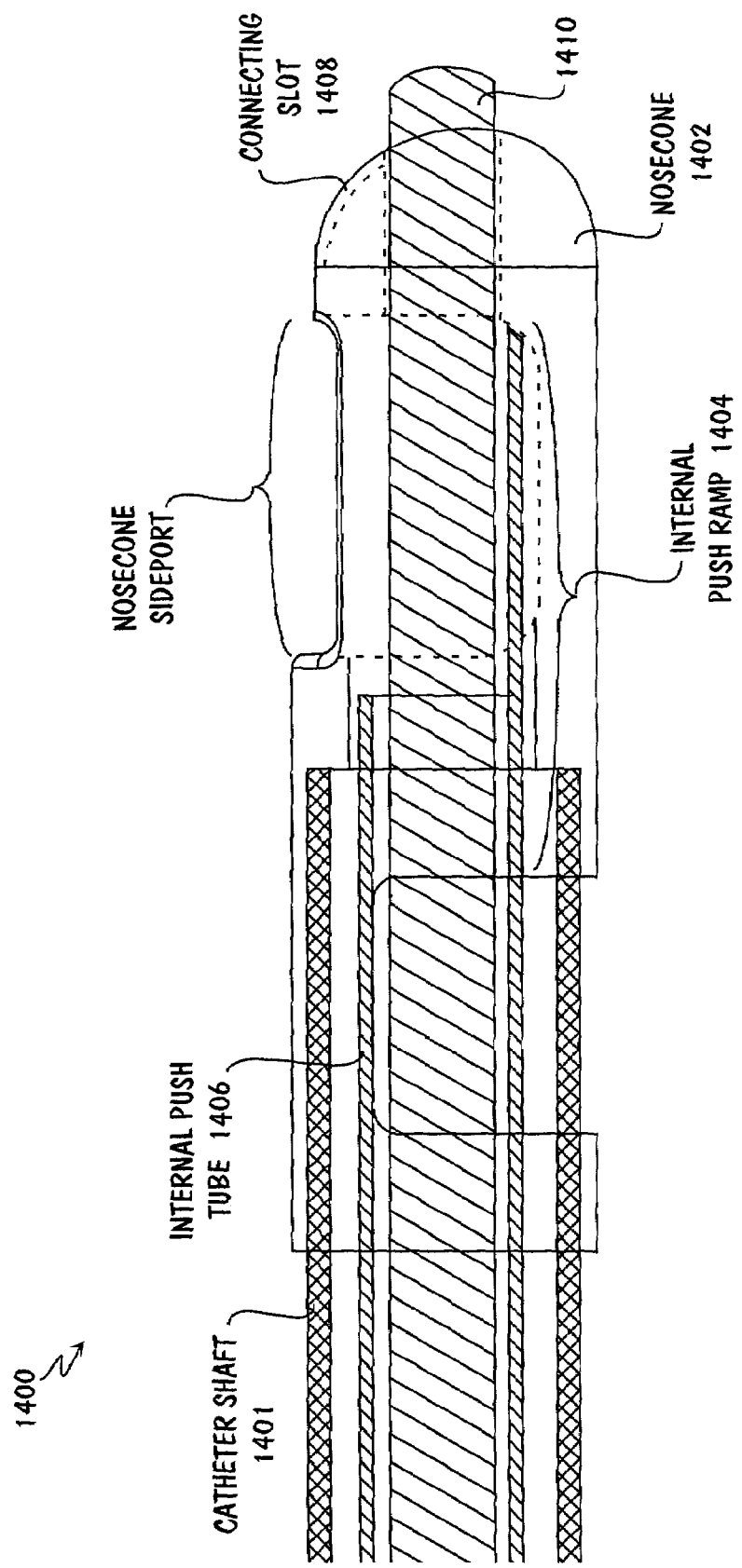
FIG. 14B is a catheter system under the embodiment of FIG. 14A showing the internal slidably disposed push ramp in a retracted position.

FIGS. 14A and 14B show a catheter system 1400 including a catheter shaft 1401 having a nosecone 1402 with an internal slidably disposed push ramp 1404 coupled to an internal push tube 1406. Extension of the internal push ramp 1404 (FIG. 14A) helps in directing a working element 1410 to a re-entry site. The nosecone 1402 further includes a nosecone slot 1408 that allows the working element 1410 to translate or reposition into the guide wire exit port 1412 as the internal ramp 1404 is retracted (FIG. 14B). A variety of working elements or devices 1410 are deployable using the internal push ramp 1404, including typical guide wires, specialized guide wires (see FIG. 16 and the associated description herein), fiber optic systems (see FIGS. 17A and 17B and the associated description herein), RF system components (see FIG. 18 and the associated description herein), and IVUS (see FIG. 19 and the associated description herein).

Figure 15:
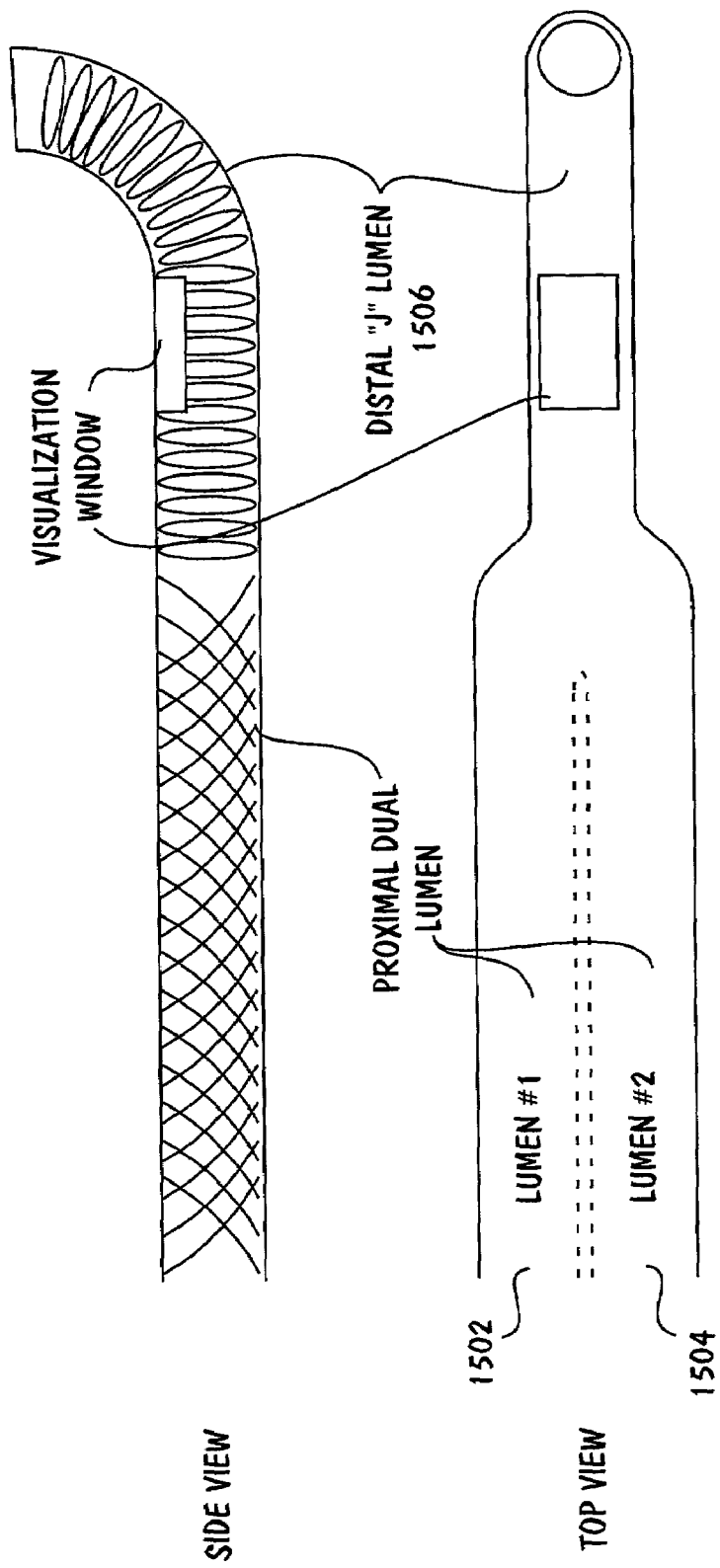
FIG. 15 is a catheter system including a dual lumen shaft that transitions distally to a single lumen shaft, under an embodiment.

FIG. 15 is a catheter system 1500 including a catheter shaft having dual lumens 1502 and 1504 in a proximal region, under an alternative embodiment of FIG. 13. In a distal region, the two lumens 1502 and 1504 merge to form a single lumen 1506. A variety of working elements or devices are deployable using this catheter system 1500, including typical guide wires, specialized guide wires (see FIG. 16 and the associated description herein), fiber optic systems (see FIGS. 17A and 17B and the associated description herein), RF system components (see FIG. 18 and the associated description herein), and IVUS (see FIG. 19 and the associated description herein).

Figure 16:
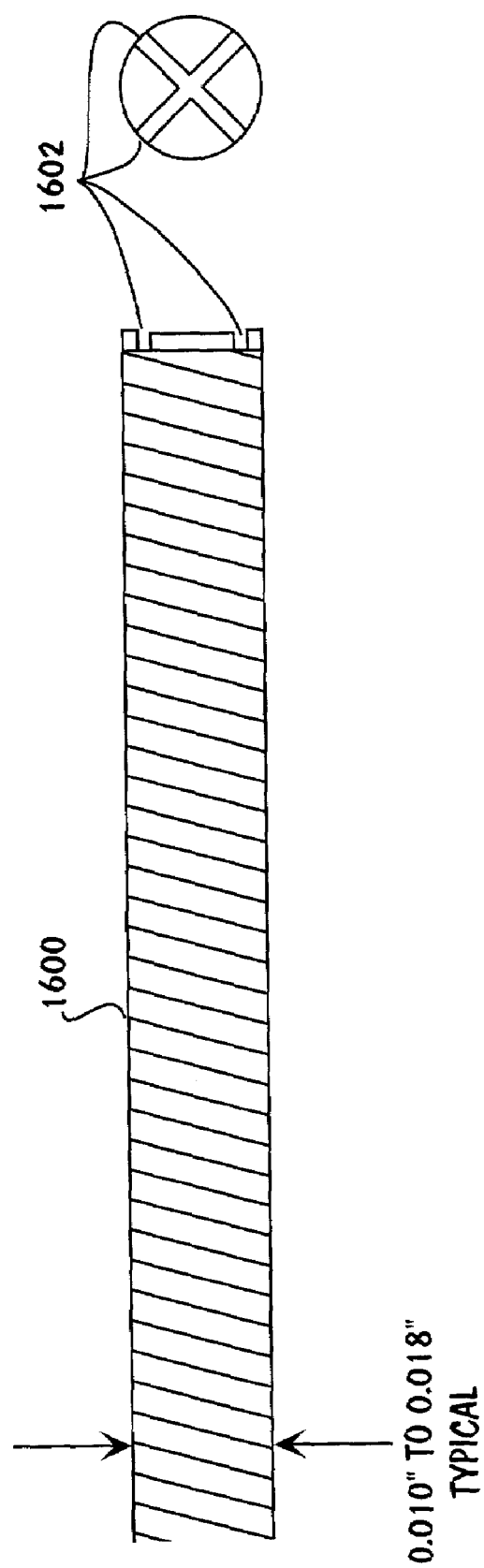
FIG. 16 is a specialized guide wire including a distal end that is machined to provide cutting flutes, under an embodiment.

FIG. 16 is a specialized guide wire 1600, under an embodiment. The guide wire 1600 includes a distal end that is machined to provide cutting flutes 1602, under an embodiment. In an alternative embodiment, the distal tip may be processed with a generally abrasive surface.

Figure 17A:
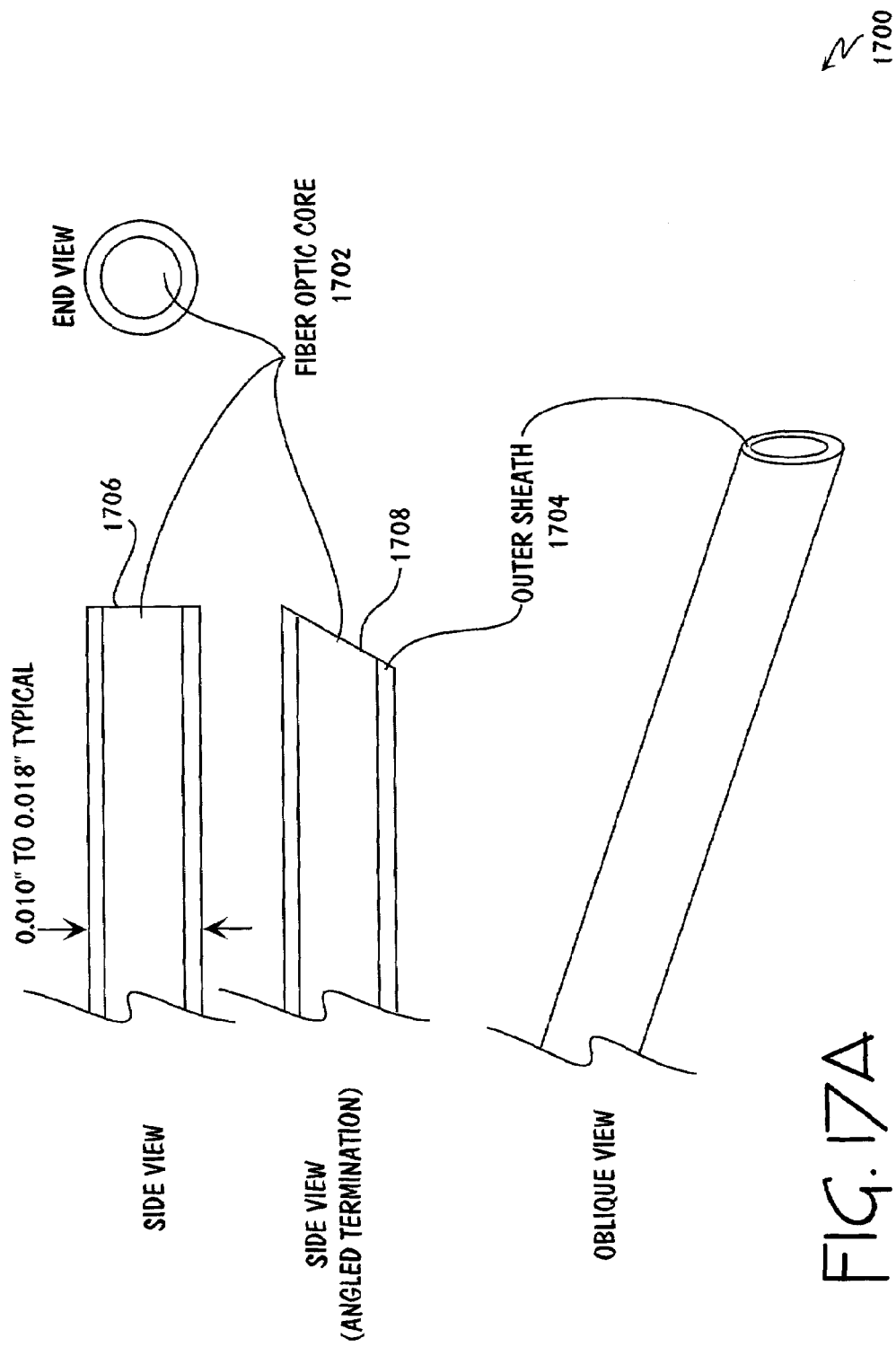
FIG. 17A is an optical fiber system of an embodiment, capable of deployment in a catheter system, for delivering laser energy to a distal termination.

FIG. 17A is an optical fiber system 1700 of an embodiment. This optical fiber system 1700 can be deployed, using any of the catheter systems described herein, to deliver laser energy to a distal termination. The optical fiber system 1700 includes a fiber optic core 1702 surrounded by an outer sheath 1704. The sheath 1704 can be formed, for example, from polyimide or polyethylene, but is not so limited. The fiber optic system 1700 terminates at the distal end in either a normal configuration 1706 or an angled configuration 1708, relative to the longitudinal axis, but any mode of termination known in the art may be used. The optical fiber system 1700 of one embodiment has an outside diameter of approximately 0.010 to 0.018 inches, but the diameter can vary depending on the planned application.

FIG. 17B is an optical fiber system 1750 including a lumen 1752, under an alternative embodiment of FIG. 17A. The lumen 1752 is surrounded by a polymer encasement 1754. The encasement 1754 of one embodiment is formed, for example, from nylon or polyethylene, but is not so limited. The encasement 1754 includes individual optical fibers 1756, where the number of optical fibers 1756 varies in accordance with planned applications. The individual fibers can terminate in any mode known in the art. The optical fiber system 1750 of one embodiment has an outside diameter of approximately 0.020 to 0.030 inches, but the diameter can vary with particular applications.

Figure 18:
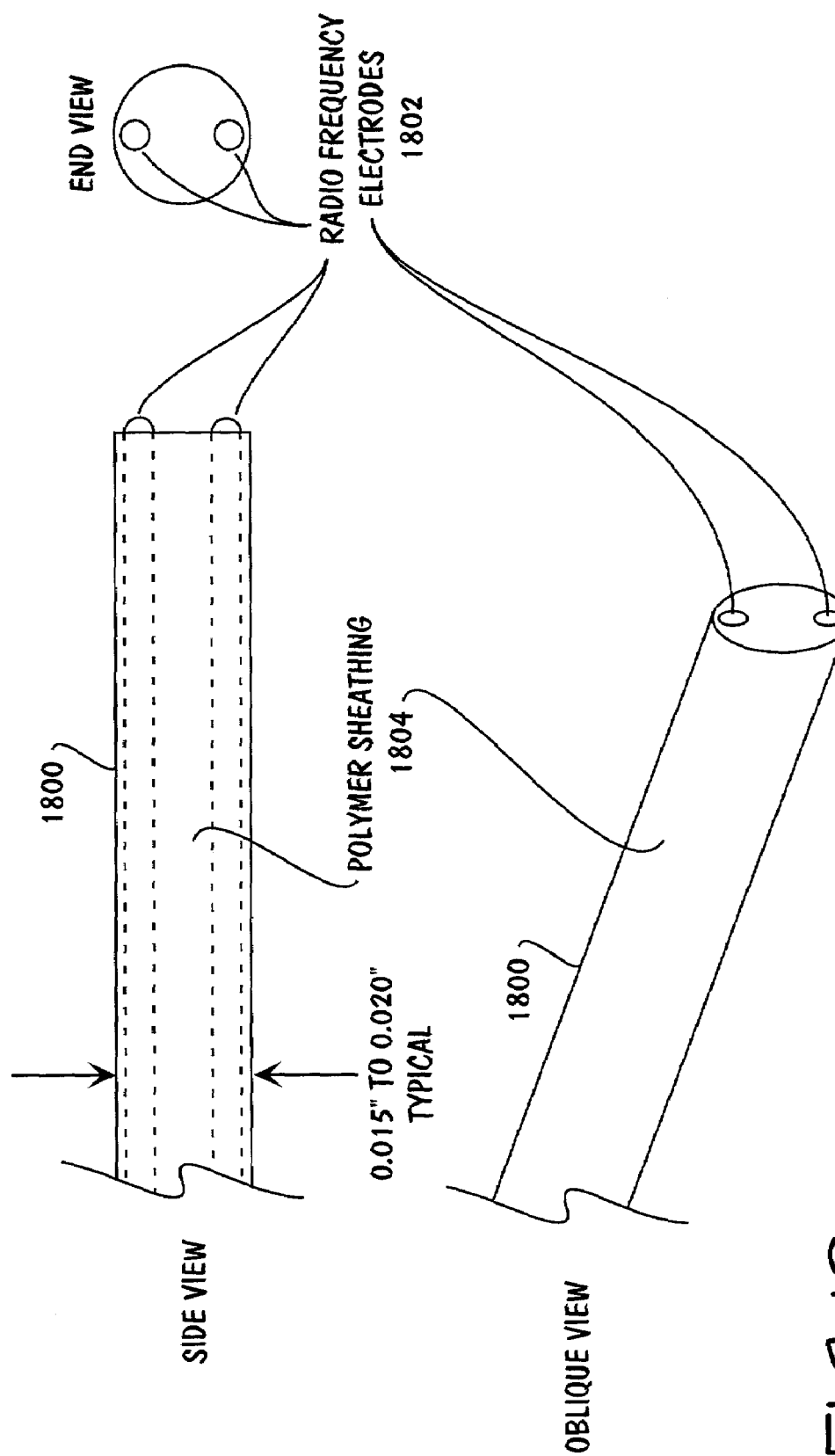
FIG. 18 is a slidably disposed element that translates within a catheter lumen and includes one or more electrodes capable of transmitting radio frequency energy, under an embodiment.

FIG. 18 is a radio frequency (RF) element 1800 including one or more electrodes 1802 capable of transmitting RF energy, under an embodiment. The RF electrodes 1802 are housed in a polymer sheathing 1804 that translates within a catheter lumen (not shown). The polymer sheathing 1804 is formed from polyethylene or nylon, but other materials may be used. The RF element 1800 can be used with the catheter system embodiments described herein.

Figure 19:
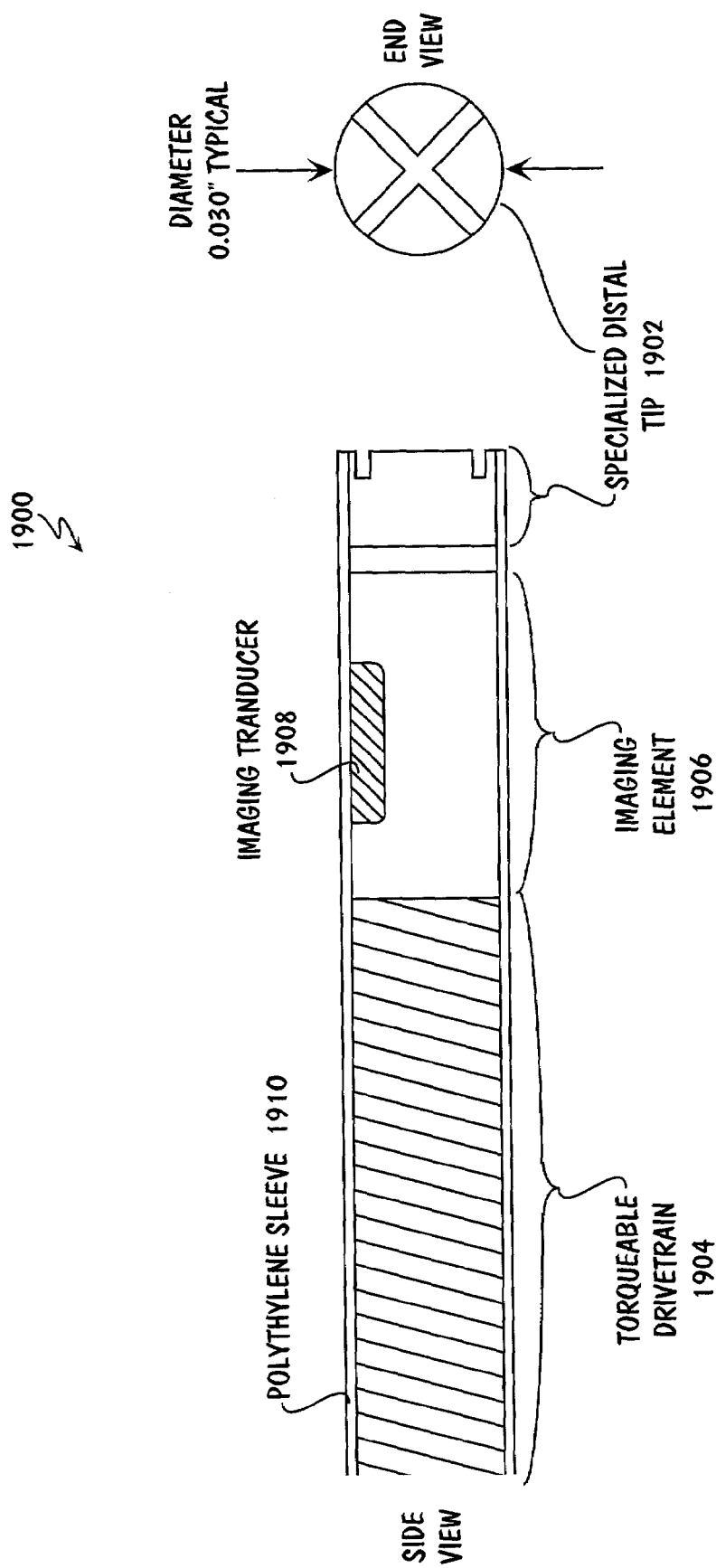
FIG. 19 is a rotational Intra-Vascular Ultrasound (IVUS) element including an integral distal tip for re-entry, under an embodiment.

FIG. 19 is a rotational IVUS element 1900 including an integral distal tip 1902 for re-entry, under an embodiment. The distal tip 1902 is coupled to a torqueable drive train 1904. The element 1900 further includes an imaging element 1906 and an imaging transducer 1908. The element 1900 is encased in a sleeve 1910 that, in one embodiment, is formed of polyethylene. The outside diameter of the element is approximately 0.030 inches, but is not so limited.

All catheter systems presented herein are delivered to the vascular site via tracking over a conventional guide wire. In some instances the guide wire is removed and other catheter elements are advanced during the course of a procedure involving the catheter system while, or in other instances, the guide wire remains in the catheter throughout the procedure.

Figure 20:
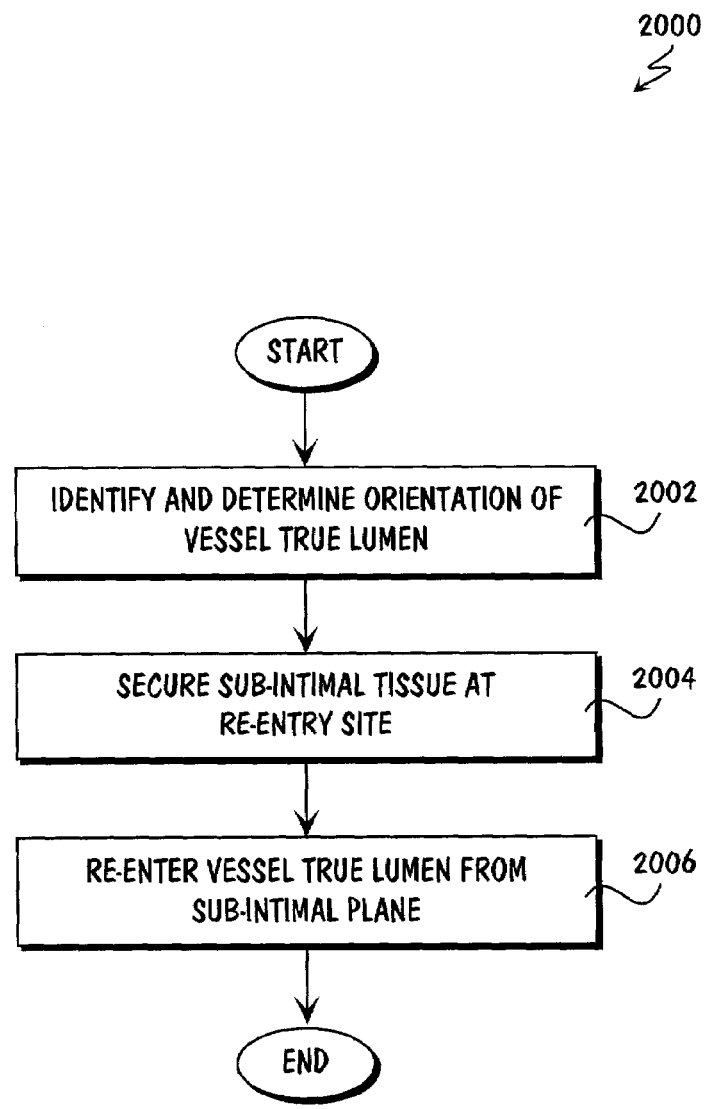
FIG. 20 is a flow diagram for vascular re-entry from a sub-intimal space.

FIG. 20 is a flow diagram for vascular re-entry from a sub-intimal space. In general, the process of re-entry from a sub-intimal plane into a vessel true lumen of an embodiment is described herein using three steps, with numerous methods and embodiments described under each step. Fundamentally, any methods from any steps can be combined to formulate a valid sequence and basis for a catheter embodiment to describe the overall procedures. The three steps include:

Step 1: Identify and determine the orientation of the vessel true lumen with respect to the sub-intimal plane. Approaches are presented under this step including the use of catheter system onboard guidance, and external guidance. Further, five methods of visualization are described.

Step 2: Physically secure the sub-intimal tissue at the re-entry site, to enable a method of re-entry into the true lumen, as described in Step 3. Three methods are described herein for securing the sub-intimal tissue.

Step 3: Establish a re-entry path from the sub-intimal plane into the vessel true lumen. Six methods of vessel re-entry are described below.

The steps are now described in detail, including the associated methods and embodiments.

Step 1: Identify and Determine the Orientation of the Vessel True Lumen with Respect to the Sub-Intimal Plane As the catheter is positioned within a sub-intimal plane, the re-entry mechanism is orientated towards the vessel true lumen. When the catheter is properly aligned, the re-entry mechnism directly faces the sub-intimal tissue that separates the dissection plane from the vessel true lumen.

Method 1 under Step 1: Intra-Vascular Ultrasound (IVUS) (FIGS. 1–15)

Figure 21:
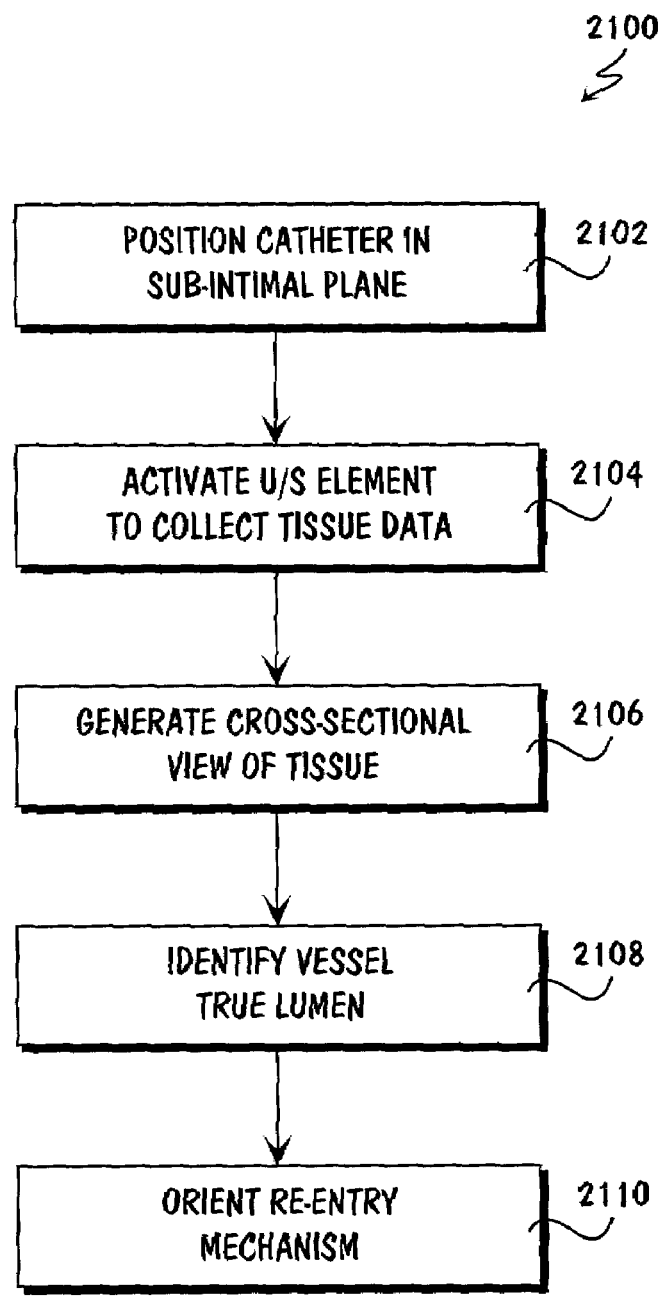
FIG. 21 is a flow diagram for identifying and determining orientation of a vessel true lumen using IVUS, under an embodiment.

FIG. 21 is a flow diagram for identifying and determining orientation of a vessel true lumen using IVUS, under an embodiment. Two IVUS systems are readily available as stand-alone devices that may serve as an element within the Re-Entry Catheter. One system, manufactured by Boston Scientific Corporation, utilizes an ultrasound element, or crystal, which is mounted at the distal end of a rotational shaft. This shaft is rotated at a specified speed while the crystal is excited by electrical signals. The crystal produces acoustic wavefronts, and the reflection of the acoustic wavefronts by tissue types of varying density are received by the crystal. Algorithms decipher the reflected acoustic signals, and the system provides a cross sectional view of the tissue surrounding the sub-intimal plane. This method easily resolves surrounding tissue and aids in identifying the vessel true lumen.

Another IVUS system, manufactured by Endosonics utilizes an array of individually mounted crystals or elements in a fixed circumferential orientation at the distal end of a small catheter shaft. This system does not rotate. Rather, each crystal is sequentially excited by an electrical signal and each crystal also receives the reflected acoustic signal. Algorithms decipher the reflected signals, and the system constructs a cross sectional image of the tissue surrounding the crystal network. This method resolves surrounding tissue and helps identify the vessel true lumen.

Typical outer diameter dimensions for IVUS systems are on the order of approximately 0.030 inches, but are not so limited.

Method 2 under Step 1: Optical Coherence Tomography (OCT) (FIGS. 1–15)

Figure 22:
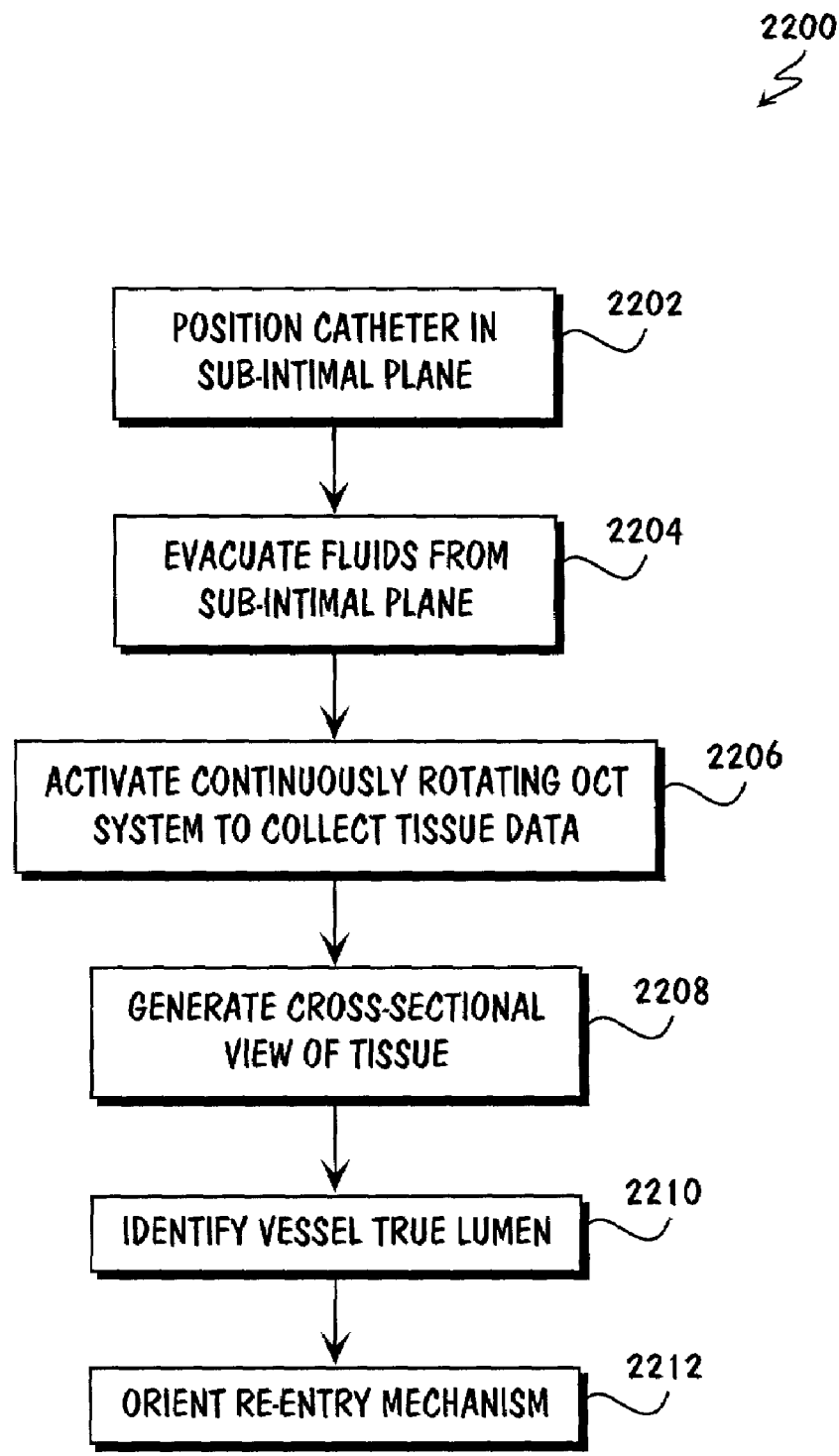
FIG. 22 is a flow diagram for identifying and determining orientation of a vessel true lumen using OCT, under an embodiment.

FIG. 22 is a flow diagram for identifying and determining orientation of a vessel true lumen using OCT, under an embodiment. In general, the OCT system delivers infrared (IR) light into tissue from the distal end of a rotating optical fiber. Delivery of the light into the tissue is accomplished by terminating the optical fiber at an angle to achieve internal reflection of the light at an approximate right angle to the central axis of the optical fiber. The fiber also receives reflected light from various tissue types. While the reflected OCT signals comprise light waves rather than acoustic waves, the reflected signals are deciphered and a cross sectional image is produced of the tissue surrounding the distal tip of the optical fiber, similar to the approach described in Method 1 under Step 1 above. While this technology has yet to be released to the market as a tool to be used within the vascular space, OCT is a proven technology that provides image resolution 5 to 25 times greater than current ultrasound embodiments.

Further, OCT technology is not able to produce an image through blood because it uses infrared light. However, the system of an embodiment evacuates fluids and/or blood from the sub-intimal plane in an embodiment, as described below. Thus, with the removal of fluids and/or blood from the sub-intimal plane, the utilization of infrared light wavelengths allows the OCT technology to create an image of the surrounding tissue and identify the true lumen. Further, the wavelength of light may be modified so as to be able to pass through blood and still produce an image of the surrounding tissue. Typical outer diameter dimensions for the OCT system are on the order of approximately 0.015 inches, but are not so limited.

Method 3 under Step 1: Optical Fiber Visualization System (FIGS. 1–15)

Figure 23:
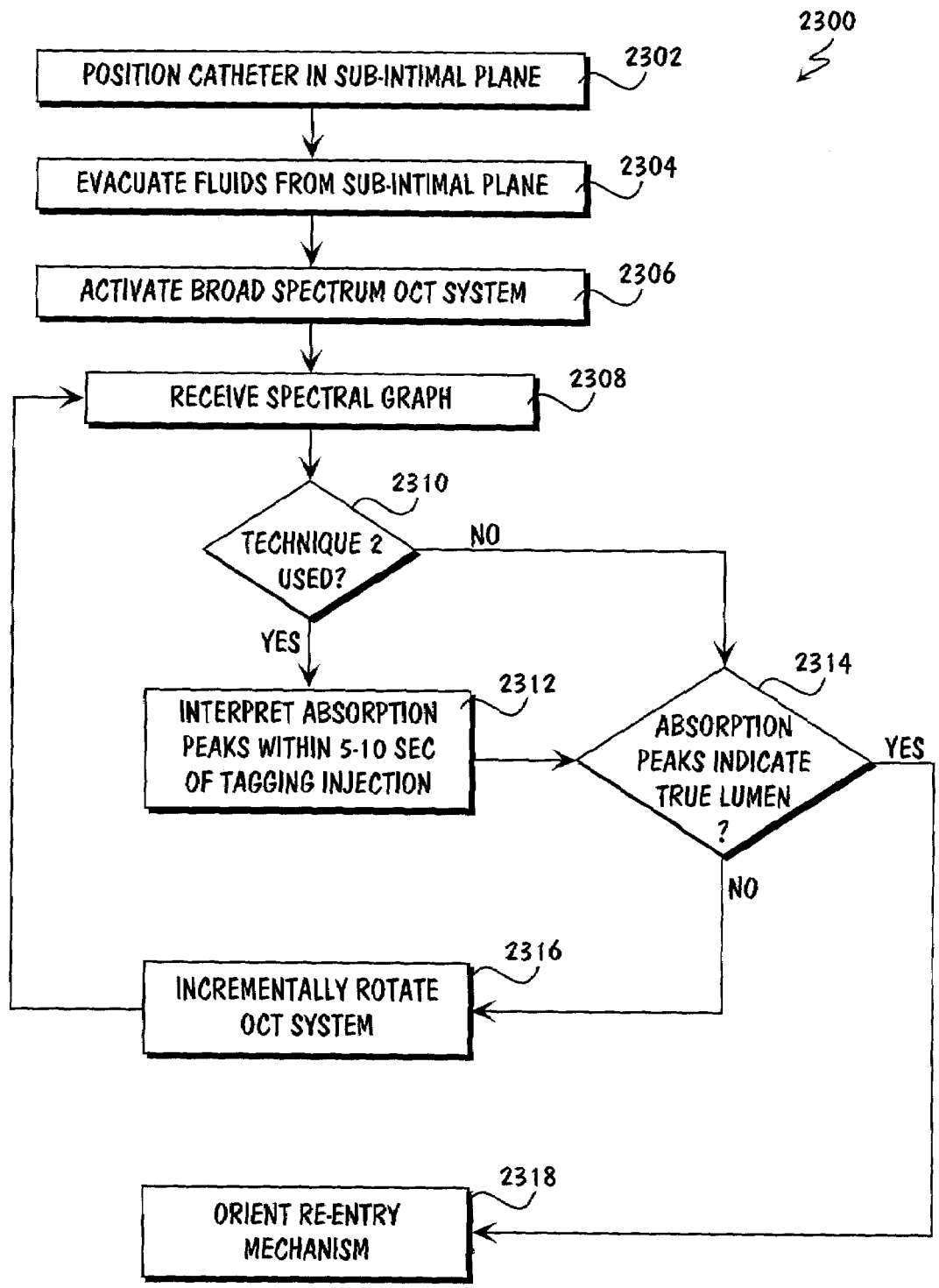
FIG. 23 is a flow diagram for identifying and determining orientation of a vessel true lumen using optical fiber visualization systems, under an embodiment.

FIG. 23 is a flow diagram for identifying and determining orientation of a vessel true lumen using optical fiber visualization systems, under an embodiment. This method uses an optical fiber system for visualization as in Method 2 under Step 1 above, except that the optical fiber system does not continuously rotate. A broad-spectrum light is applied to the proximal end of the optical fiber. The light is reflected at the distal terminal end of the fiber into surrounding body tissue by terminating the optical fiber at an approximate right angle. Specific wavelengths of light are absorbed and/or transmitted and/or reflected based upon the type of tissue exposed to the light. The reflected light signals are processed to produce a spectral graph. This method, therefore, incrementally rotates the fiber, sending and receiving broadband light signals, until the specific absorption peaks are received that signal the presence of the true lumen. Typical outer diameter dimensions of the fiber optic system may range from 0.010 to 0.020 inches, but are not so limited.

This method can be implemented using three techniques that are now described.

Technique 1 (Method 3 under Step 1):

The absorption peak of hemoglobin is sought, which indicates the presence of a blood pool, i.e. the true lumen. Note that in the case where re-entry of an artery is desired, the absorption peak sought is that of oxygenated hemoglobin, which is a double peak signal having peaks at known wavelengths in the spectrum. Since large veins also are in close proximity to arteries, it would be important to distinguish between the single absorption peak of de-oxygenated hemoglobin, and the desired double peak of oxygenated hemoglobin. Once the double absorption peaks of de-oxygenated are identified, the direction of the true lumen is determined.

Technique 2 (Method 3 under Step 1):

Local injection into the vessel true lumen with an agent having a characteristic absorption peak can selectively tag blood cells only in the vessel true lumen. Various tagging agents approved by the Food and Drug Administration (FDA) can be used to tag blood cells. Tagging the blood cells in the vessel true lumen is accomplished from a distal entry point to the vessel.

As an example, consider an occlusion in the right coronary artery of the coronary vasculature. The re-entry catheter described herein is advanced into the dissection plane. By definition, the vessel true lumen at this time in the procedure has not been accessed. However, many times collateral vessels from the left coronary vasculature will branch to the right coronary artery at various locations, and often at connection points which are distal to typical occlusion locations in the right coronary artery. Thus, by injecting this agent into the left coronary vasculature, some of the agent will travel through the collateral vessels and feed into the right coronary artery, distal to the occlusion, i.e. the true lumen of the vessel the re-entry catheter is attempting to access. This procedure uses efficient timing of the injection of the agent and interpretation of the absorption peaks, because the agent will clear from the distal portion of the right coronary artery typically within 5–10 seconds. Note that this example is easily applicable to a blockage in the left arterial system, with collateral connections from the right coronary artery.

Technique 3 (Method 3 under Step 1):

A systemic injection with an agent that tags red blood cells is used. In this case, the agent tags all viable red blood cells in the entire vascular system, both arterial and venous. The agent is chosen to provide an identifiable absorption peak. One advantage of this method is that a continuous generation of spectral data can be performed since the agent bond to the blood cells has a long half-life.

Method 4 under Step 1: Doppler Ultrasound (FIGS. 1–8, 15)

Figure 24:
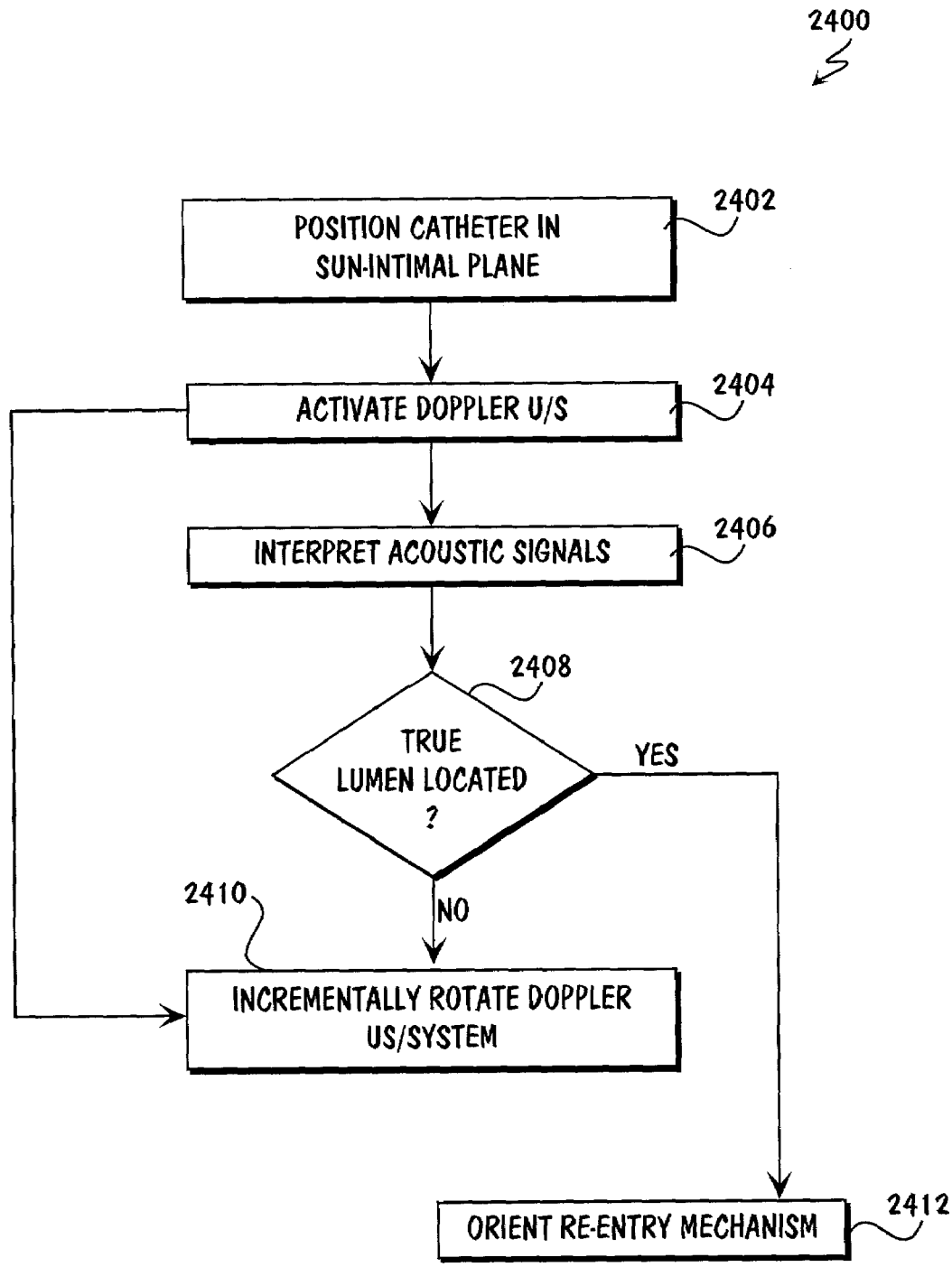
FIG. 24 is a flow diagram for identifying and determining orientation of a vessel true lumen using Doppler ultrasound systems, under an embodiment.

FIG. 24 is a flow diagram for identifying and determining orientation of a vessel true lumen using Doppler ultrasound systems, under an embodiment. Doppler ultrasound is also used to identify blood flow in the vessel true lumen, under an embodiment. The fundamental basis of this technique is not unlike that used to generate weather radar maps. The Doppler method emits acoustic energy from a transducer/receiver mounted in the catheter. The transducer/receiver subsequently recognizes and measures phase shifts in these acoustic signals that are reflected off of moving, formed blood components, e.g. red blood cells and/or white blood cells in the vessel true lumen, thereby establishing an orientation. Details of the Doppler method are understood by those knowledgeable in this art. Typical outer diameter dimensions of the doppler system are approximately 0.020 inches.

Note that the visualization hardware referenced in Methods 1 through 4 under Step 1 may be an integral component of the embodiments of FIGS. 7, 8, and 15, i.e., not removed from the catheter during the procedure. However, in the embodiments of FIGS. 1 through 6 and 9 through 14 this hardware is used as part of the catheter system at the beginning of the procedure to determine orientation of the vessel true lumen, and then removed to allow the introduction of other elements used to conduct the procedure.

Method 5 under Step 1: Fluoroscopic Marking System (FIGS. 1–15)

Figure 25:
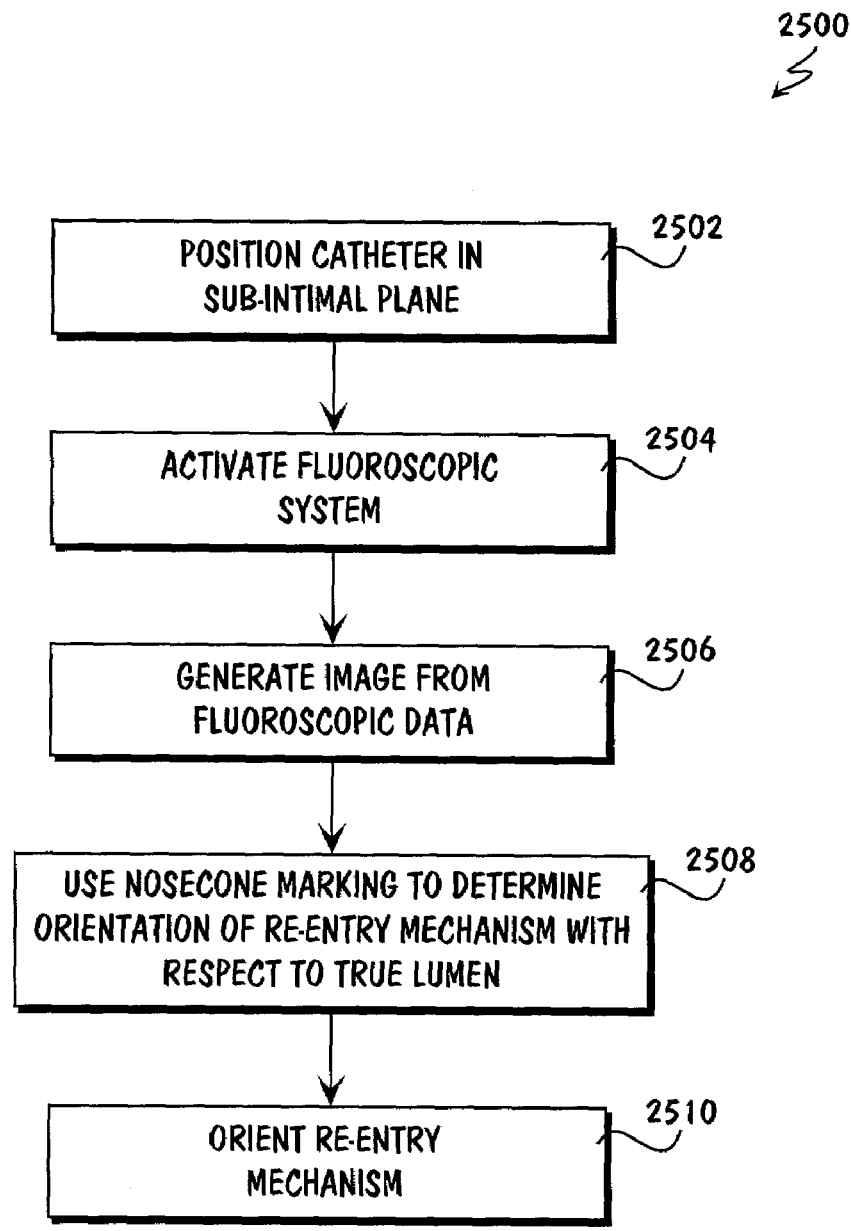
FIG. 25 is a flow diagram for identifying and determining orientation of a vessel true lumen using fluoroscopic marking systems, under an embodiment.

FIG. 25 is a flow diagram for identifying and determining orientation of a vessel true lumen using fluoroscopic marking systems, under an embodiment. This method describes the use of a fluoroscopic marking system at the distal end of the catheter to identify the location of the re-entry mechanism, with respect to the vessel true lumen. One implementation of this method takes advantage of the catheter nosecone itself which may be fabricated from a fluoroscopic material, e.g. stainless steel, platinum, or gold coated ceramic. For example the side port of the nosecone, which identifies the re-entry direction of the catheter, should be readily visible under fluoroscopy. Alternatively, a marking cutout may be placed within the proximal section of the nosecone, the design of which would indicate the position of the re-entry mechanism of the catheter.

Step 2: Physically Secure the Sub-Intimal Tissue at the Re-Entry Site

In the formation of a sub-intimal plane, extra-vascular fluid as well as blood may collect in this space, and the sub-intimal space may grow in volume. A re-entry catheter advanced into the sub-initimal space can thus "float" within this space. This can result in the catheter's inability to establish a "purchase" on the sub-intimal tissue that separates the catheter from the vessel true lumen. Thus, it is procedurally important to evacuate this volume of fluid so as to allow the re-entry portion of the catheter to be placed in direct, intimate contact with the sub-intimal tissue. This increases the likelihood of the re-entry mechanism successfully establishing a re-entry path to the vessel true lumen.

Method 1 under Step 2: Evacuating Fluid of Sub-Intimal Plane (FIGS. 1–15)

Figure 26:
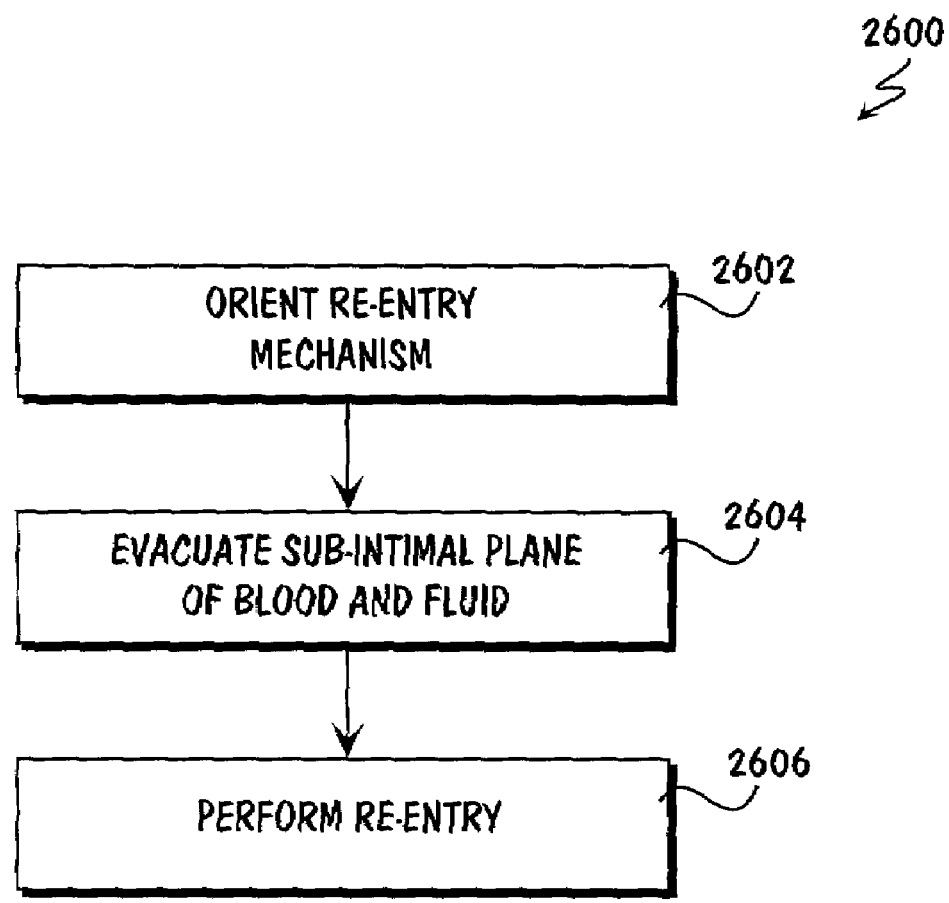
FIG. 26 is a flow diagram for securing sub-intimal tissue at a vessel re-entry site by evacuating fluid of the sub-intimal plane, under an embodiment.

FIG. 26 is a flow diagram for securing sub-intimal tissue at a vessel re-entry site by evacuating fluid of the sub-intimal plane, under an embodiment. This method describes the action of evacuating the volume of fluid that is typically contained within the sub-intimal plane. The action of evacuating the sub-intimal plane of all extra-vascular fluid and blood, can subsequently "lock" the sub-intimal tissue onto the surface of the catheter. Thus, the sub-intimal tissue that separates the sub-intimal plane from the true lumen is held in position on the surface of the re-entry catheter, facilitating a chosen method of creating a re-entry pathway back to the true lumen.

More specifically, the embodiments described herein and shown in the Figures include a distal nosecone having a sideport or catheter distal termination with ports which may be used to translate a vacuum to within the sub-intimal space. Note that in some embodiments the distal guide wire port serves to communicate vacuum to within the sub-intimal space. Further, additional evacuation/vacuum ports of various sizes and shapes may be positioned along the distal portion of the catheter which would reside in the sub-intimal plane.

Method 2 under Step 2: Application of Vacuum (FIGS. 1–3, 5–12, 14)

Figure 27:
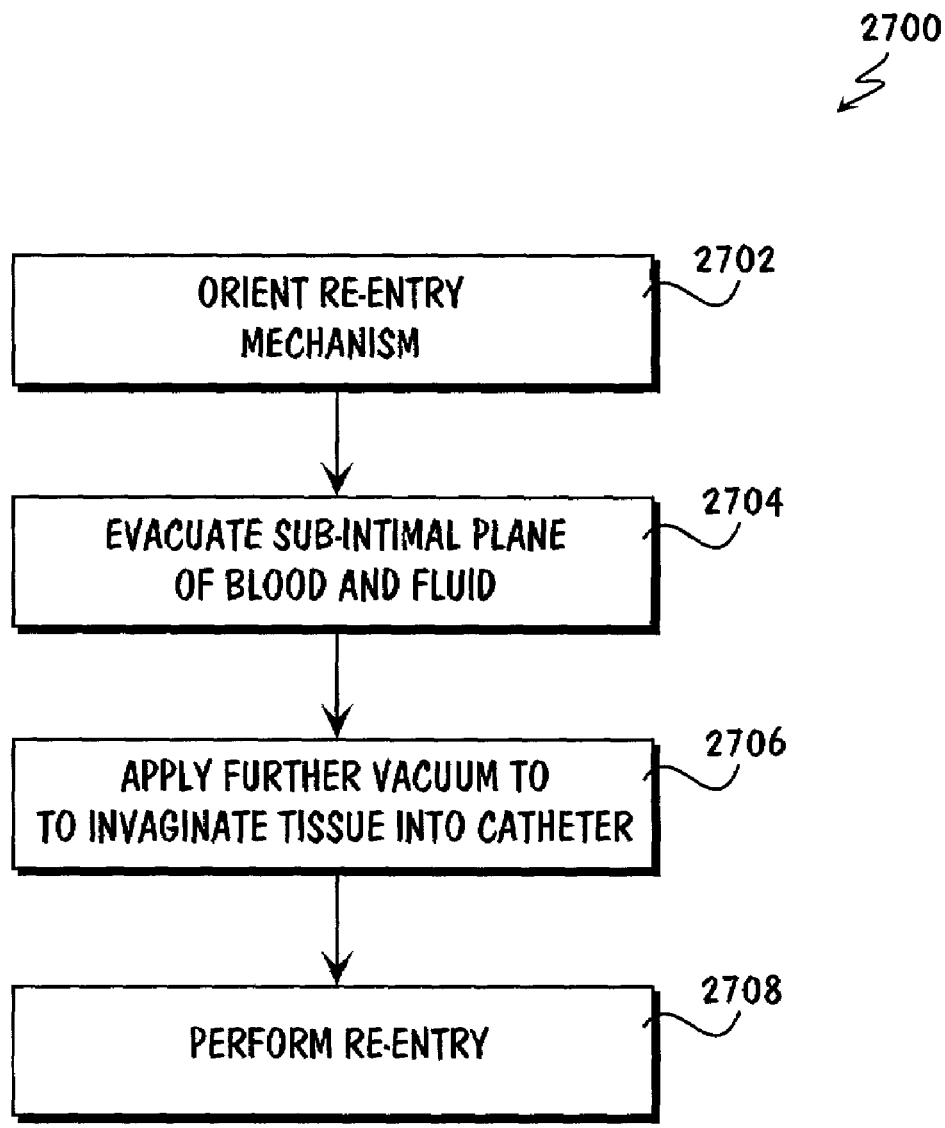
FIG. 27 is a flow diagram for securing sub-intimal tissue at a vessel re-entry site using vacuum, under an embodiment.

FIG. 27 is a flow diagram for securing sub-intimal tissue at a vessel re-entry site using vacuum, under an embodiment. This method describes the further application of vacuum such that the sub-intimal tissue that separates the sub-intimal plane from the vessel true lumen is invaginated within a distal portion of the catheter. Once this tissue is contained within the interior of the catheter itself, various methods may be subsequently employed to establish a physical pathway through it and back to the vessel true lumen, as detailed below. One advantage of this method is that all re-entry techniques may be performed within the catheter, reducing risk to any surrounding vascular tissue and inadvertent perforation of the vessel wall to the pericardial space.

Method 3 under Step 2: Mechanical Means (FIG. 8)

Figure 28:
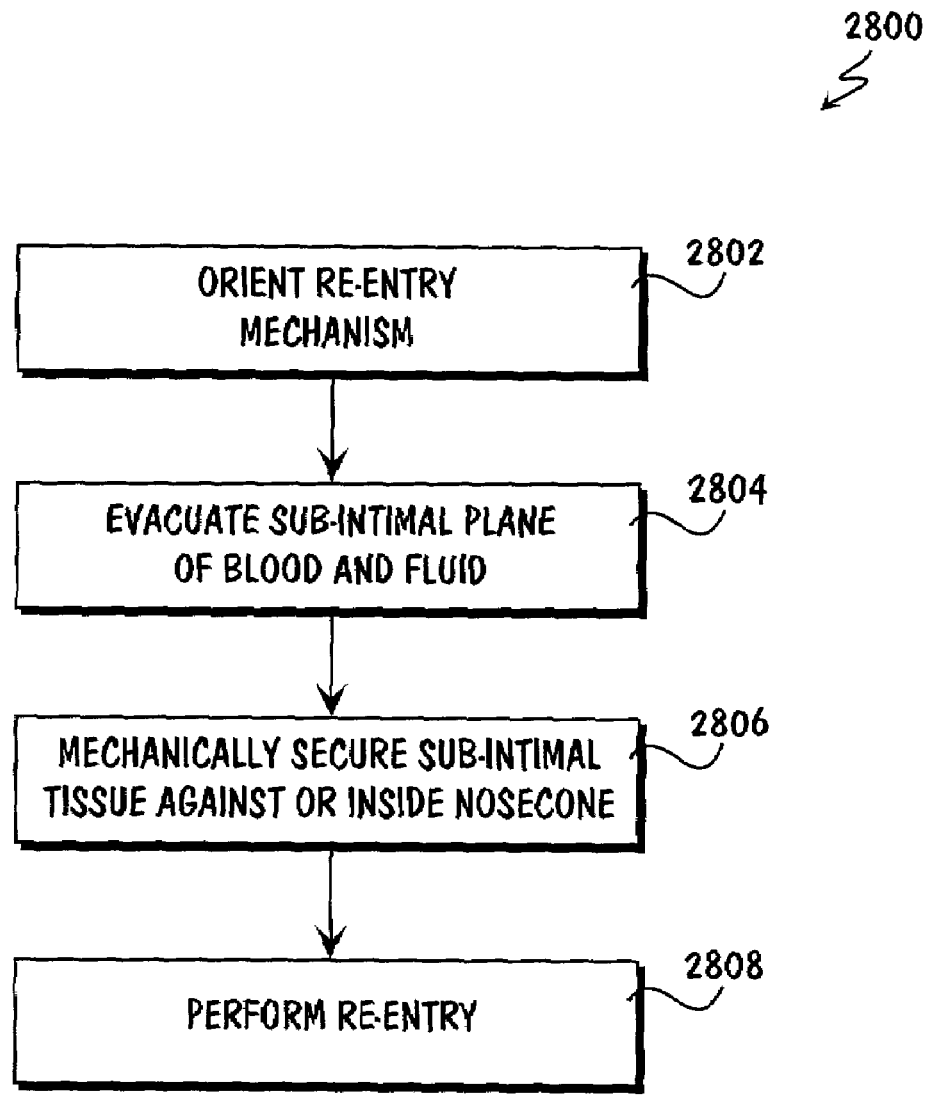
FIG. 28 is a flow diagram for securing sub-intimal tissue at a vessel re-entry site using mechanical devices, under an embodiment.

FIG. 28 is a flow diagram for securing sub-intimal tissue at a vessel re-entry site using mechanical devices, under an embodiment. This method describes mechanically securing the sub-intimal tissue prior to employment of a re-entry mechanism to gain access into the vessel true lumen, per Step 3 below. Physical or mechanical securing of the sub-intimal tissue may be accomplished by a variety of embodiments. Mechanical means including tweezing or forcep action, pinch rollers, or skewers are used to grab and secure the sub-intimal tissue. The tweezing- or forcep-type mechanical system can be used to simply hold the tissue secure against the nosecone, or grab and pull the sub-intimal tissue within the nosecone. Skewers may be used to pierce the sub-intimal tissue and hold it intimately against the catheter, or grab and pull the sub-intimal tissue within the nosecone. The skewer tip could remain embedded in the sub-intimal tissue, or could advance through the tissue such that the skewer tip pierces in and out of the tissue and the skewer is directed into a receiving port at the opposite section of the nosecone. In this last configuration, the tissue is held captive on the skewer.

Step 3: Establish a Re-Entry Path from the Sub-Intimal Plane into the Vessel True Lumen This section describes the methods to establish the re-entry pathway. As each method may apply to various ones of the embodiments herein, numerous combinations of method/catheter platform are presented.

Method 1 under Step 3: Cutting Sub-Intimal Tissue (FIGS. 1–3)

This method describes the cutting of a pathway through the sub-intimal tissue into the true lumen. Three embodiments for this method include a catheter shaft with a nosecone termination which houses the visualization element (Step 1, Methods 1–4) and the cutting member as shown in the referenced figures, and further described below. The nosecone has a sideport opening which allows for visualization of the vascular area (per Step 1, Methods 1 through 4) and identification of the orientation of the vessel true lumen. Fluoroscopic features of the nosecone can also be used in conjunction with the primary visualization method to facilitate alignment to the true lumen. The nosecone also has a distal end port that allows the catheter to be tracked in a co-linear fashion over a conventional guide wire to the chosen vascular site.

Contained within the outer shaft is an internal shaft to which a distal cutting element is attached. The catheter outer shaft and the internal shaft may be fabricated using any number of methods know in the art. An example would be polymer lamination onto a stainless steel braided tube. Alternatively, either shaft may be fabricated as described in U.S. patent application Ser. No. 09/984,498, filed Oct. 16, 2001. The cutting member may be fabricated starting with a stainless steel hypotube, and forming the appropriate cutting features, e.g. serrations (FIG. 1), needle point (FIGS. 2 and 3), or a sharpened conical termination (not shown). The cutting features may be formed using standard machining methods or electronic discharge machining (EDM). Representative dimensions of a cutting element may range from approximately 0.030 to 0.040 inches in diameter. The nosecone may be fabricated of similar materials, using similar fabrication methods.

Figure 29:
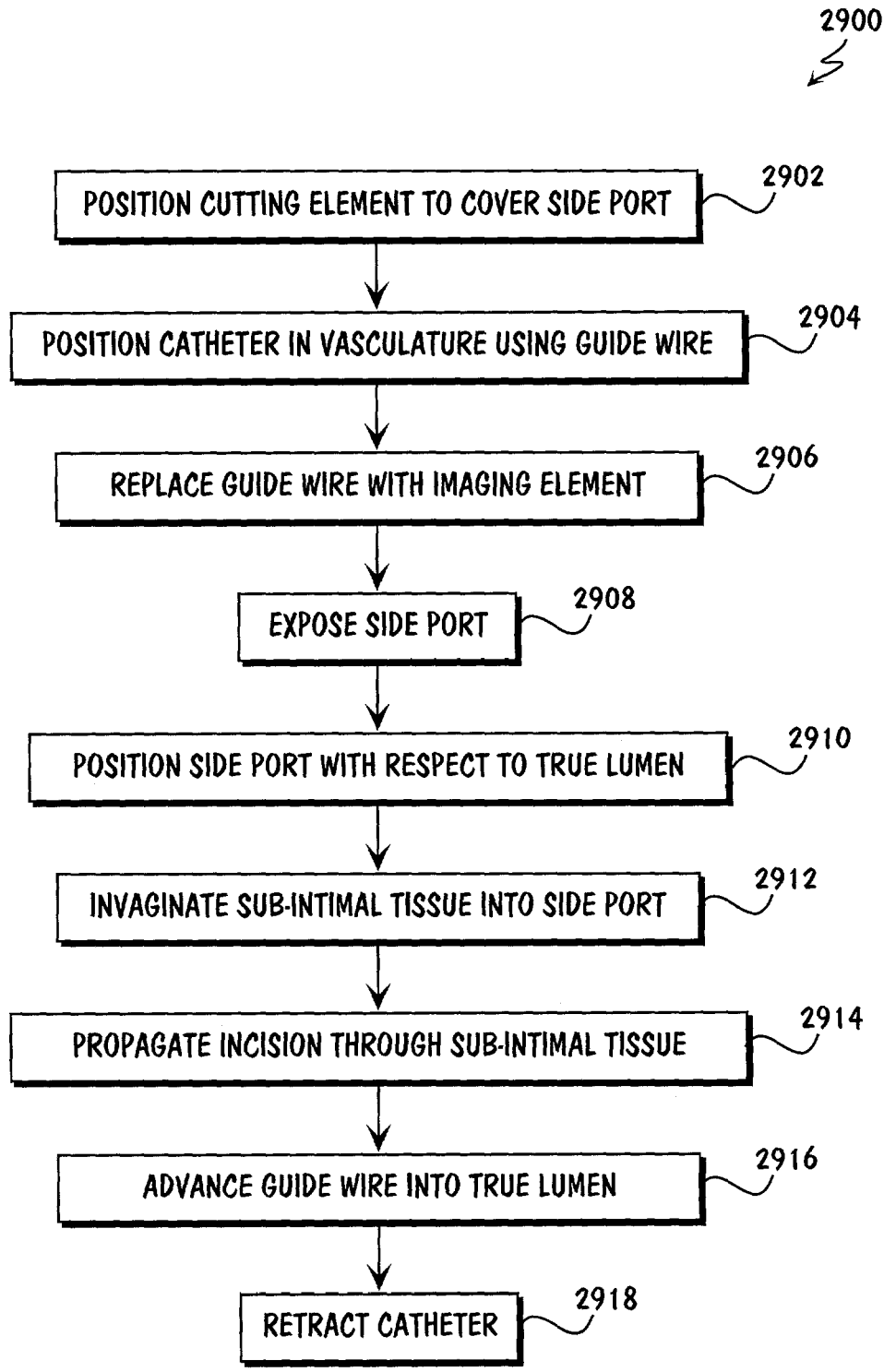
FIG. 29 is a flow diagram for cutting through sub-intimal tissue into a true lumen, under an embodiment.

FIG. 29 is a flow diagram for cutting through sub-intimal tissue into a true lumen, under an embodiment. Procedurally, prior to introducing the catheter into the vasculature, the imaging element is removed from the catheter. The inner shaft/cutting element is first positioned such that it covers the nosecone sideport. For the embodiments of FIGS. 1 and 2, the cutting element is advanced fully distal such that the distal termination of the cutting element is "garaged" within the distal receiving section of the nosecone. In the embodiment of FIG. 3, the cutting element is rotated until it is positioned opposite the nosecone sideport, e.g., the sideport is covered by the wall of the hypotube opposite the cutting feature. In these configurations, the cutting element covers the nosecone sideport and presents an uninterrupted surface that can be effectively tracked through the vasculature. The catheter may then be introduced onto a guide wire and tracked to the appropriate vascular location.

Once the vascular site has been reached, the guide wire is removed and the imaging element is introduced and advanced until it is positioned at the nosecone sideport. The cutting element is retracted, exposing the sideport. The imaging element is activated and the sideport is rotationally positioned towards the vessel true lumen. Vacuum is applied to the interior of the catheter outer shaft per Step 2, Method 2, thus beginning the process to invaginate the sub-intimal tissue into the nosecone sideport. While confirming that the sideport remains directed towards the vessel true lumen, the imaging element is retracted, allowing more space for the sub-intimal tissue to further invaginate into the nosecone sideport. Note that under this configuration, visualization of the vessel true lumen is no longer possible since the imaging element is retracted proximal to the sideport. While maintaining vacuum, the cutter is then advanced, distally for the embodiments of FIGS. 1 and 2, and proximally for the embodiment of FIG. 3. In the embodiment of FIG. 1, the cutting element may also be rotated to facilitate the cutting action. In this process, the actuation of the cutting element mechanically traps and compresses the tissue within the sideport, allowing the cutting features to propagate an incision through the sub-intimal tissue, and through to the vessel true lumen.

Note that an alternative to the process described above is to not retract the visualization element prior to the cutting action. Thus the visualization element is postioned at the nosecone sideport, and cutting is performed while simultaneously viewing the alignment to the vessel true lumen. Also note that in this alternative technique, the presence of the visualization element in the nosecone prevents maximum invagination of tissue into the nosecone. Thus the first technique allows cutting through thicker sub-intimal tissue which separates the sub-intimal plane from the vessel true lumen.

Upon establishment of a pathway into the vessel true lumen, the vacuum still applied at the nosecone will aspirate blood from the vessel true lumen, through the pathway in the sub-intimal tissue and into the catheter shaft, ultimately reaching the proximal end of the catheter. The vacuum will also be lost. These two events would indicate that a pathway has been successfully established into the vessel true lumen.

Once a pathway has been established into the vessel true lumen, the imaging element is removed, the cutting element is once again positioned to cover the nosecone sideport, and a guide wire is advanced through the catheter to exit the nosecone endport. The guide wire is thus manipulated through the pathway into the vessel and the catheter is removed from the vasculature.

Typical dimensions of the catheter components are as follows: outer shaft/nosecone outside diameter is approximately 0.060 to 0.070 inches; cutting element outside diameter is approximately 0.040 to 0.050 inches; and imaging element outside diameter is as described above.

Method 2 under Step 3: Piercing (FIGS. 8 and 9)

This method describes the general piercing of a pathway through the sub-intimal tissue into the true lumen. This can be approached under a first embodiment where the sub-intimal tissue is held onto the surface of the catheter via vacuum (FIG. 9), or under a second embodiment where the sub-intimal tissue is invaginated into the catheter via vacuum (FIG. 8). These two embodiments are now described.

Embodiment 1 (Method 2 under Step 3) (FIG. 9)

This embodiment includes a nosecone or molded catheter termination attached to the distal end of the catheter, and an internal slidably disposed actuating cannula.

The catheter shaft may be any of a number of catheter shafts known in the art. The nosecone includes a side exit port and a distal end port coupled via a slot which, and as will be described below, allows the guide wire to move from the side port into the distal end port when the catheter is retracted proximally over the guide wire. The cannula is guided out of the nosecone sideport via two internal exit ramps, one on either side of the cannula. The distal end port of the nosecone allows the catheter to be tracked in a co-linear fashion over a standard coronary guide wire.

Figure 30:
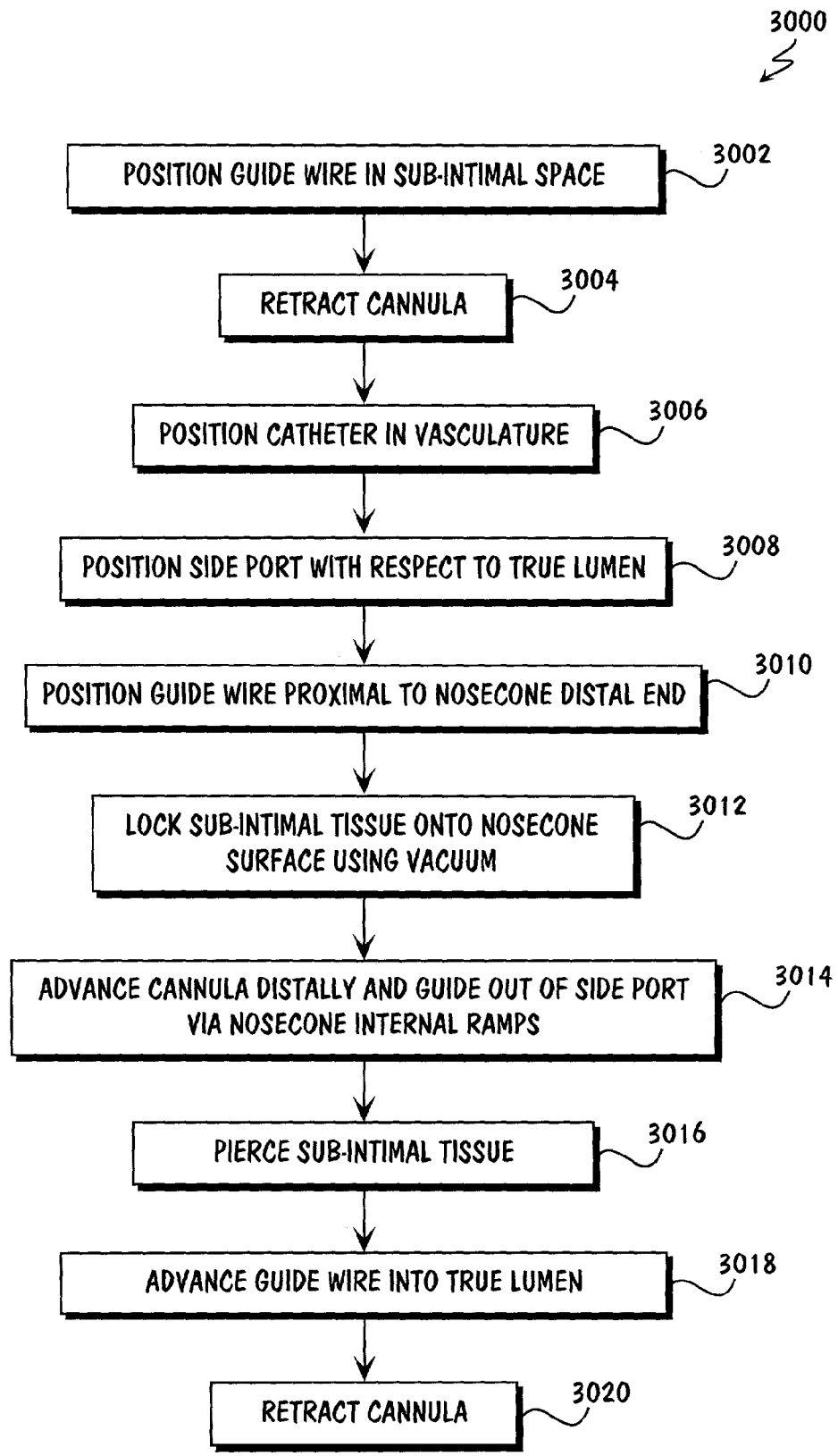
FIG. 30 is a flow diagram for piercing a pathway through sub-intimal tissue into a true lumen, under an embodiment.

FIG. 30 is a flow diagram for piercing a pathway through sub-intimal tissue into a vessel true lumen under an embodiment. Procedurally, a guide wire is placed in the sub-intimal space of the target vasculature such that the guide wire distal end is located distal to the occluded area of the vessel. The cannula is retracted to a position proximal to the exit ramp so that the cannula exit port is co-linear with the inner diameter of the nosecone. This configuration allows the proximal end of the guide wire to be passed through the nosecone distal end port. The cannula, the catheter shaft, and thus the catheter may be tracked over the guide wire to the vascular site.

The catheter is then aligned to the vessel true lumen. This is accomplished per Step 1, Methods 1 through 4, or Step 1, Method 5. FIG. 9 illustrates both configurations. In the case using Step 1, Methods 1 through 4, the guide wire is retracted from the catheter, and the visualization element is advance into the nosecone. The element is activated at the nosecone side port and the side port is rotated to face the vessel true lumen. The visualization element is removed, and the cannula and guide wire are re-introduced.

In the case using Method 5, the side port is rotated to face the vessel true lumen per fluoroscopic visualization.

The distal tip of the guide wire is now positioned approximately 2 centimeters (cm) proximal from the distal tip of the nosecone. At this point the application of vacuum as described in Step 2, Method 1 can be used to evacuate fluid from the sub-intimal plane and lock the sub-intimal tissue onto the surface of the nosecone.

Next, the cannula is advanced distally and guided out of the nosecone sideport via the internal exit ramps to pierce the sub-intimal tissue and gain access to the vessel true lumen. Once the vessel true lumen is accessed, the cannula remains in place while the guide wire is advanced into the true lumen. The cannula may then be retracted into the catheter and resume its original position. The cannula may have various distal terminations, e.g. needle shaped, sharpened conical shaped, or circular serrations. The angle of the internal ramp can vary from approximately 30 to 80 degrees, but is not limited to these angles.

Lastly, the guide wire is held in position while the catheter is removed. As the catheter is retracted proximally over the guide wire, the floppy distal end of the guide wire may be able to pass through the nosecone side port. However, as the nosecone reaches the stiff mid and proximal sections of the guide wire, the guide wire falls through the slot connecting the side port with the end port. Therefore, as the catheter nosecone is retracted over the mid and proximal sections of the guide wire, it does so with the guide wire traveling through the nosecone distal port.

Typical dimensions of the catheter components are as follows: outer shaft/nosecone outside diameter is approximately 0.050 to 0.060 inches; cannula element outside diameter is approximately 0.020 to 0.030 inches.

Embodiment 2 (Method 2 under Step 3) (FIG. 8)

This embodiment includes: a nosecone or molded catheter termination attached to the distal end of the catheter lumen which houses the visualization element (Step 1, Methods 1 through 4); a lumen which houses either a guide wire or the piercing element; lumens for vacuum ports; and optional forceps to physically secure the sub-intimal tissue.

The nosecone has a side port opening which allows for visualization of the vascular area (per Step 1, Methods 1–4) and identification of the orientation of the vessel true lumen. It also has an end port for tracking over a guide wire. Fluoroscopic features of the nosecone may also be used in conjunction with the primary visualization method to facilitate alignment to the true lumen. The nosecone also has a distal end port that allows the catheter to be tracked in a co-linear fashion over a conventional guide wire to the chosen vascular site.

The catheter shaft may be any of a number of catheter shafts known in the art. An example includes polymer lamination onto a stainless steel braided tube. Alternatively, the shafts may be fabricated as described in U.S. patent application Ser. No. 09/984,498, filed Oct. 16, 2001. The nosecone may be fabricated/machined from stainless steel and EDM methods.

Figure 31:
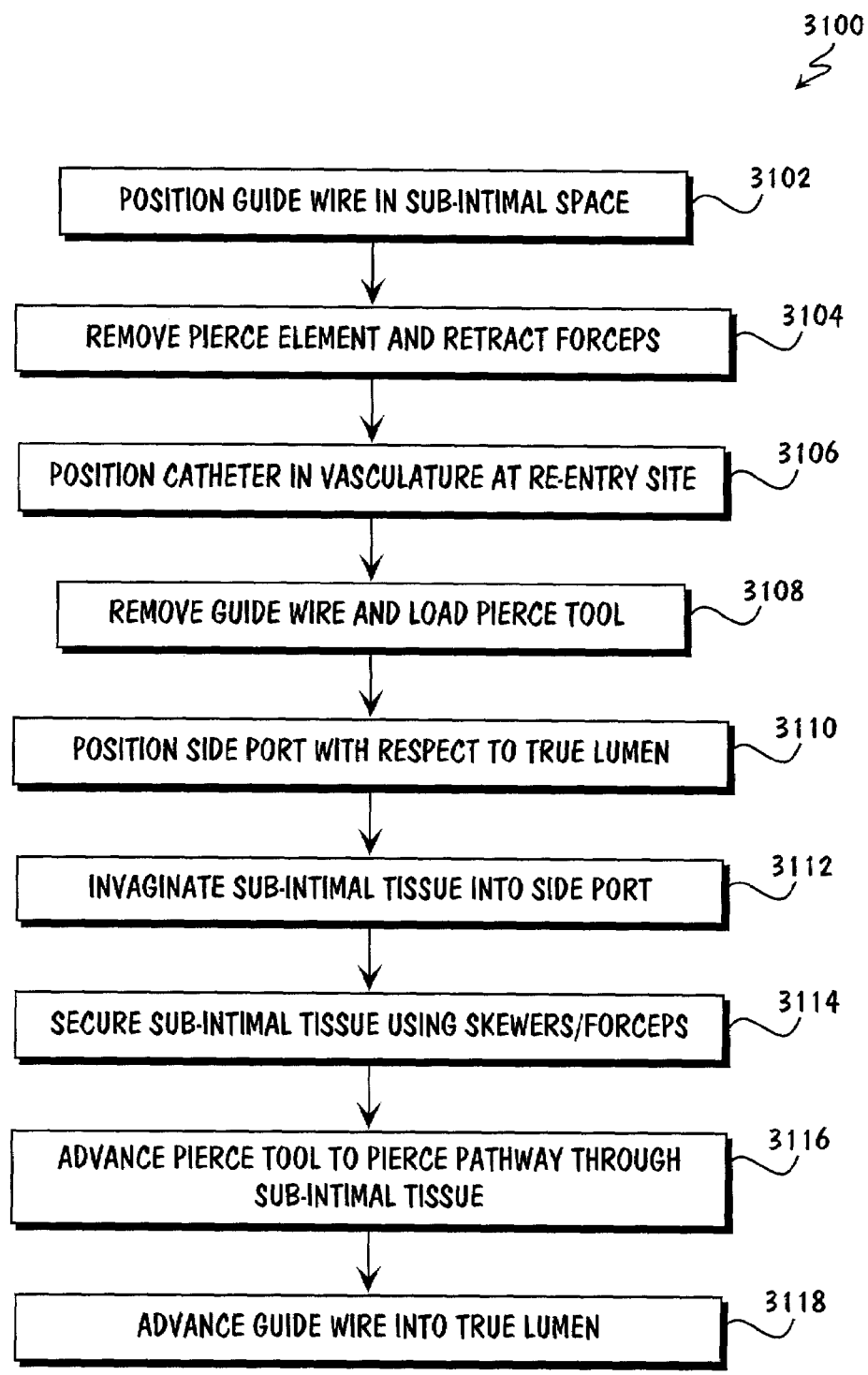
FIG. 31 is a flow diagram for establishing a pathway through sub-intimal tissue into a true lumen, under an alternative embodiment.

FIG. 31 is a flow diagram for piercing a pathway through sub-intimal tissue into a vessel true lumen, under an alternative embodiment. Procedurally, a guide wire is placed in the sub-intimal space of the target vasculature such that the guide wire distal end is located distal to the occluded area of the vessel. The pierce element is removed from the catheter, and the forceps (optional) are retracted to within the nosecone. The catheter is loaded onto the guide wire and tracked to the vascular site. The guide wire is removed. The pierce tool may be loaded into the catheter and the distal tip positioned just proximal to the nosecone sideport. The visualization element is activated and the sideport is directed towards the vessel true lumen.

Next, vacuum is applied to the vacuum lumens per Step 2, Method 2 thus beginning the process to invaginate the sub-intimal tissue into the nosecone sideport. While confirming that the sideport remains directed towards the vessel true lumen, the skewers/forceps may be advanced thereby further securing the sub-intimal tissue per Step 2, Method 3.

The imaging element is then retracted, allowing more space for the sub-intimal tissue to further invaginate into the nosecone sideport. Note that under this configuration, visualization of the vessel true lumen is no longer possible since the imaging element is retracted proximal to the sideport.

Next, while maintaining vacuum, the pierce tool is advanced to pierce a pathway through the sub-intimal tissue, and through to the vessel true lumen. The pierce element is one of two fundamental types: including a lumen for a guide wire; and without a lumen. Each pierce element can have a variety of distal terminations, e.g., needle shaped, sharpened conical shaped or circular serrations around the outer diameter.

When using the pierce element without a lumen, once the pierce element has pierced a pathway across the sub-intimal tissue, it is retracted and removed from the catheter, and a guide wire introduced into the same catheter lumen and advanced through the sub-intimal tissue, and into the vessel true lumen.

When using the pierce element with an end lumen, once the pierce element has pierced a pathway across the sub-intimal tissue, its distal position is maintained within the vessel true lumen while a guide wire is advanced through the pierce element lumen. The guide wire exits the distal end of the pierce element and enters the vessel true lumen. The pierce element is then retracted fully into the nosecone.

For procedures using a pierce tool having a side lumen, after piercing, the guide wire is passed through the side port and into the vessel true lumen. The pierce tool is not retracted, and the catheter is removed over the guide wire.

Note that an alternative to the process described above is to not retract the visualization element prior to the piercing action. Thus the visualization element is positioned at the nosecone side port, and piercing is performed while simultaneously viewing the alignment to the vessel true lumen. Also note that in this alternative technique, the presence of the visualization element in the nosecone prevents the maximum invagination of tissue into the nosecone. Thus the first technique allows cutting through thicker sub-intimal tissue which separates the sub-intimal plane from the vessel true lumen.

Once a pathway is established into the vessel true lumen, the vacuum still applied at the nosecone aspirates blood from the vessel true lumen through the pathway in the sub-intimal tissue and into the catheter shaft, ultimately reaching the proximal end of the catheter. Further, the vacuum is lost. These two events may indicate that a pathway has been successfully established into the vessel true lumen. Once a pathway is established the guide wire is advanced into the true lumen, and the guide wire is held in position while the catheter is removed.

Typical dimensions of the catheter components are as follows: outer shaft/nosecone outside diameter is approximately 0.050 to 0.060 inches; pierce element outside diameter is approximately 0.010 to 0.015 inches; and the imaging element outside diameter is as described in Step 1 above.

Method 3 under Step 3: Guidewire (FIGS. 4, and 7 through 15)

This method describes a catheter system which facilitates the use of either a conventional guide wire or specialized guide wire to establish a pathway across the sub-intimal tissue. The guide wire may be specially designed with a tip configuration that contains minute cutting members, or flutes, or the tip may be processed to provide an abrasive surface. In either case, these tip surface features would cut or abrade a pathway through the sub-intimal tissue.

Micro-machining methods to fabricate the flutes or cutting features may include laser machining, electric discharge machining (EDM), or high-precision conventional machining. An abrasive tip surface may be fabricated using a micro-abrasive blaster using abrasive materials such as titanium oxide, or sodium bicarbonate. Very small abrasive features may also be laser machined on to the surface of the guide wire tip by the use of an Excimer laser in combination with a de-focusing mask. The de-focusing mask is a flat sheet fabricated from metal or other appropriate material, designed with a pattern of holes and/or slits or other shapes, which is placed between the laser light and the guide wire tip. This pattern is reduced in size and ablated onto the surface of the guide wire tip by the laser light that passes through the mask.

Note that these specialized guide wire tips are designed to cut or abraid a pathway through sub-intimal tissue when agitated/rotated and used in conjunction with the re-entry catheter, yet once introduced into the vessel true lumen, would not have the ability to exit into an extra-vascular space.

Embodiment 1 (Method 3 under Step 3) (FIG. 4)

A first embodiment includes a distal nosecone and dual lumen catheter shaft. One lumen of the catheter shaft houses the imaging element, per Step 1, Methods 1–4, and the other lumen houses the guide wire.

Figure 32:
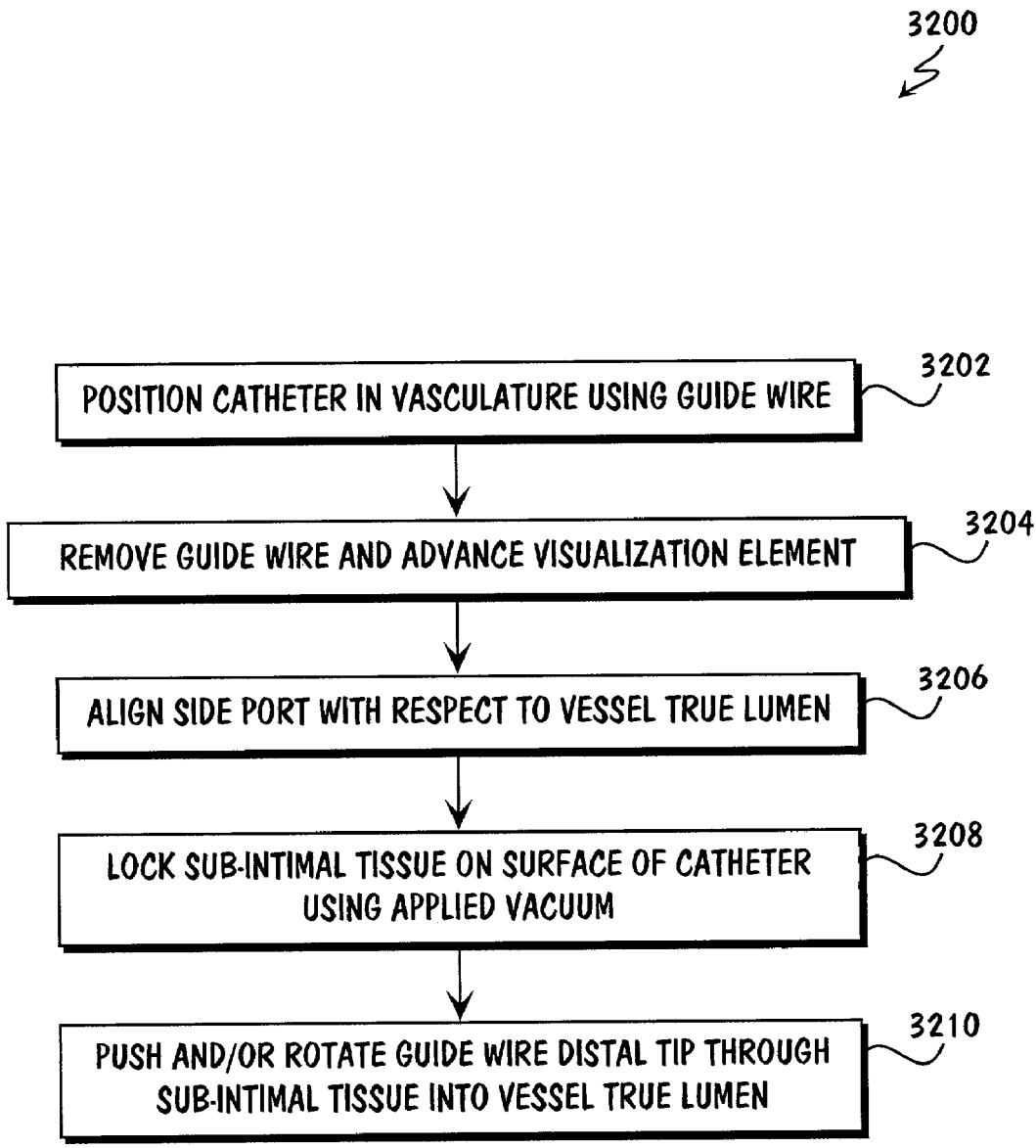
FIG. 32 is a flow diagram for using a guide wire to establish a pathway through sub-intimal tissue into a vessel true lumen, under an embodiment.

FIG. 32 is a flow diagram for using a guide wire to establish a pathway through sub-intimal tissue into a vessel true lumen, under an embodiment. Procedurally, the visualization element is removed from the catheter, and using this lumen the catheter is tracked over a guide wire to the desired sub-intimal location.

Once the catheter is properly advanced in the sub-intimal plane, the guide wire is removed and the visualization element is advanced to the distal end of the nosecone. The visualization element is activated and the catheter is properly aligned to the vessel true lumen. Note that the pathway of the visualization element to the tissue may be through the shaft material itself. In the case of IVUS, this type of visualization may "see" through HDPE, and thus this is the preferred material for the dual lumen shaft for the visualization element lumen and the guide wire lumen. Alternatively, other visualization methods, e.g. Doppler, fiber optic, OCT may require a "window" through the visualization lumen to view the tissue.

Vacuum may be applied per Step 2, Method 1, evacuating the dissection plane and locking the sub-intimal tissue on the surface of the catheter. The guide wire is then pushed, and/or rotated to allow the guide wire distal tip to establish a pathway through the sub-intimal tissue and into the vessel true lumen. Lastly, while maintaining the guide wire position, the catheter is retracted and removed from the vasculature.

Typical dimensions of the catheter components are: outer shaft/nosecone outside diameter is approximately 0.050 to 0.070 inches; specialized guide wire outside diameter is approximately 0.010 to 0.018 inches; imaging element outside diameter is as described in Step 1 above.

Embodiment 2 (Method 3 under Step 3) (FIGS. 7 and 8)

This embodiment includes a distal nosecone and a multiple lumen catheter shaft that houses a visualization element per Step 1, Methods 1 through 4, a specialized guide wire, and optional separate vacuum ports.

Figure 33:
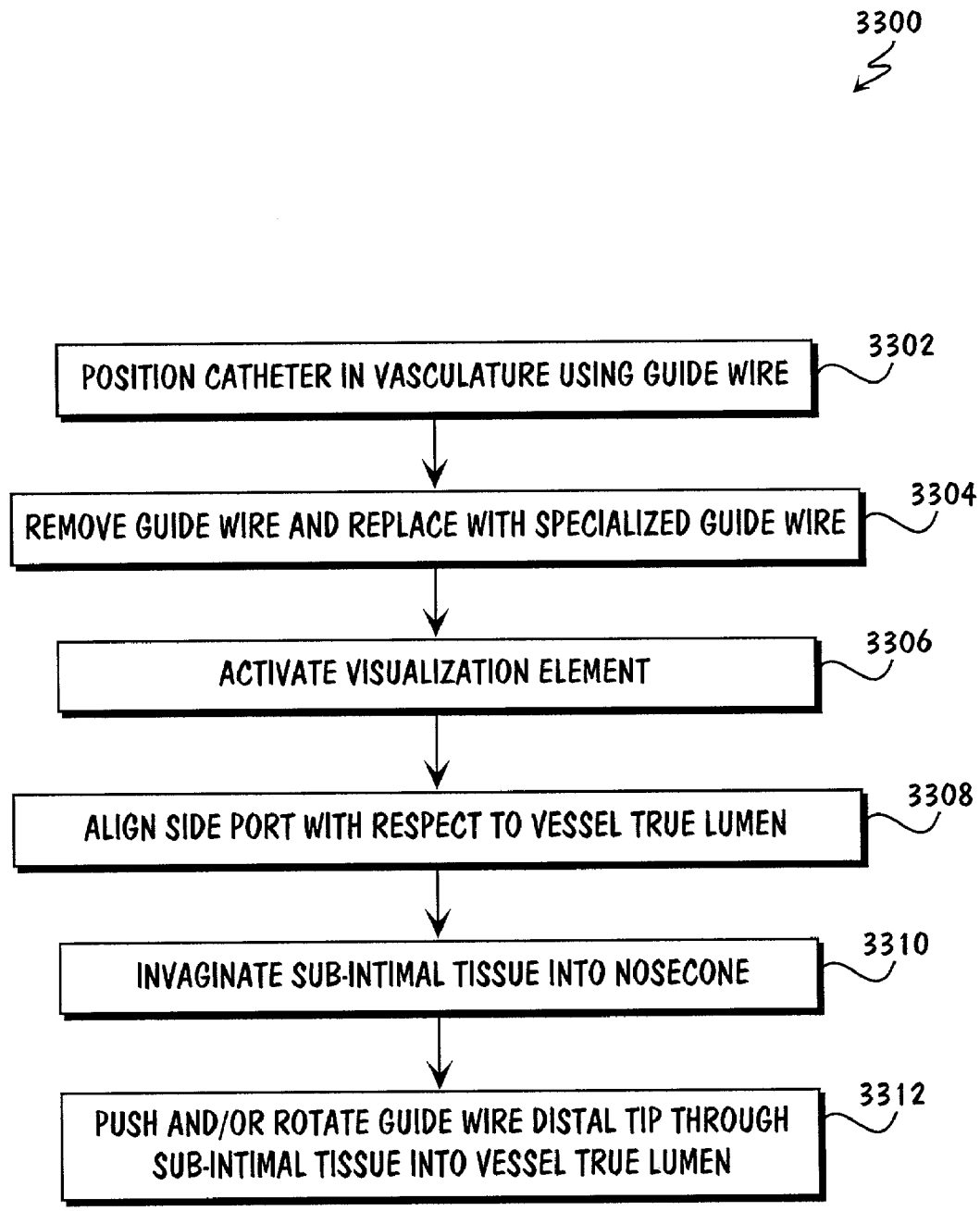
FIG. 33 is a flow diagram for using a guide wire to establish a pathway through sub-intimal tissue into a vessel true lumen, under a first alternative embodiment.

FIG. 33 is a flow diagram for using a guide wire to establish a pathway through sub-intimal tissue into a vessel true lumen, under a first alternative embodiment. Prior to the introduction of the catheter into the vasculature, the specialized guide wire is removed. Using this same lumen, the catheter is tracked over a guide wire to the desired sub-intimal location. Once the catheter is properly advanced in the sub-intimal plane, the guide wire is removed and replaced by the specialize guide wire.

The visualization element is activated and the catheter is properly aligned to the vessel true lumen. Vacuum may be applied per Step 2, Method 2, evacuating the dissection plane and invaginating the sub-intimal tissue into the catheter. Note that vacuum may be applied through the guide wire lumen, the visualization element lumen, or through optional vacuum ports as shown in FIG. 7. At this point, the visualization element may be retracted proximally into the catheter shaft, adding more room for the sub-intimal tissue to be invaginated into the nosecone. This may be desired in the case that the sub-intimal tissue is thick, and requires a deeper purchase in order to create a pathway into the vessel true lumen. Note FIG. 8 is a similar embodiment which shows optional forceps or skewers to hold the sub-intimal tissue.

Next, the guide wire is pushed, and/or rotated to allow the guide wire distal tip to establish a pathway through the sub-intimal tissue and into the vessel true lumen. While maintaining the guide wire position, the catheter is retracted and removed from the vasculature.

Typical dimensions of the catheter components are as follows: outer shaft/nosecone outside diameter is approximately 0.050 to 0.060 inches; specialized guide wire outside diameter is approximately 0.010 to 0.018 inches; imaging element outside diameter is as described in Step 1 above.

Embodiment 3 (Method 3 under Step 3) (FIG. 9)

This embodiment includes a nosecone or molded catheter termination attached to the distal end of the catheter, and an internal slidably disposed actuating cannula. The catheter shaft may be any of a number of catheter shafts known in the art. The nosecone includes a side exit port and a distal end port coupled via a slot which, and as will be described later, allows the guide wire to move from the side port into the distal end port when the catheter is retracted proximally over the guide wire. The cannula is guided out of the nosecone side port via internal exit ramps. The angle of the internal ramp is from approximately 30 degrees to 80 degrees, but not necessarily limited to these angles. The distal end port of the nosecone allows the catheter to be tracked in a co-linear fashion over a standard coronary guide wire. Representative dimensions are as follows: side port width is approximately 0.027 inches; slot width and distal port widths are approximately 0.016 inches; cannula outside diameter is approximately 0.025 inches; and cannula inside diameter is approximately 0.016 inches. Note that the internal ramp is the same width as the side port.

Figure 34:
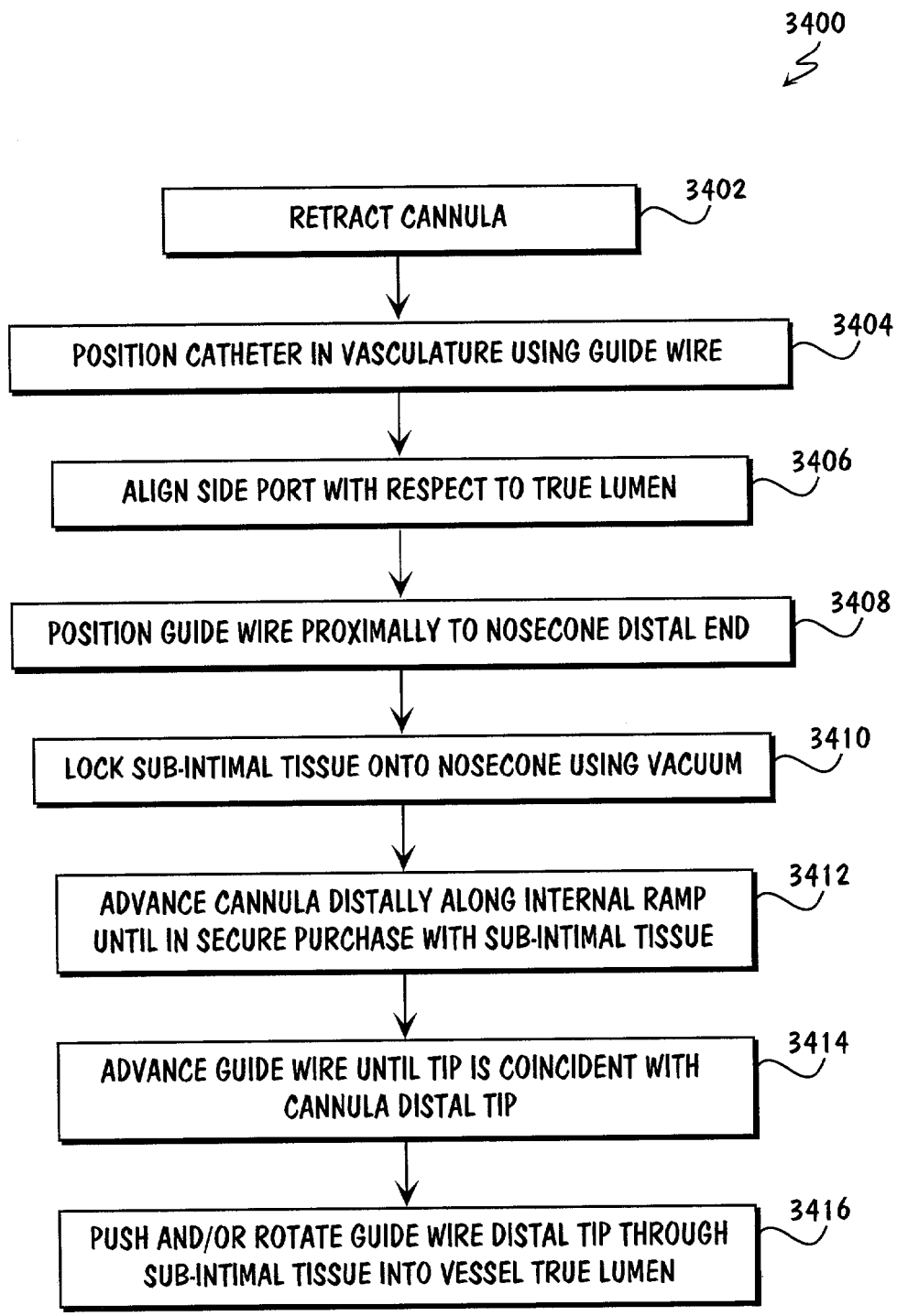
FIG. 34 is a flow diagram for using a guide wire to establish a pathway through sub-intimal tissue into a vessel true lumen, under a second alternative embodiment.

FIG. 34 is a flow diagram for using a guide wire to establish a pathway through sub-intimal tissue into a vessel true lumen, under a second alternative embodiment. Procedurally, a guide wire is placed in the sub-intimal space of the target vasculature such that the guide wire distal end is located distal to the occluded area of the vessel. The cannula is retracted to a position proximal to the exit ramp so that the cannula exit port is co-linear with the inner diameter of the nosecone. This configuration allows the proximal end of the guide wire to be passed through the nosecone distal end port, the cannula and the catheter shaft, and thus the catheter may be tracked over the guide wire to the vascular site.

The catheter is then aligned to the vessel true lumen. This may be accomplished per Step 1 Methods 1–4, or Step 1, Method 5. In the case where Methods 1–4 are used, the guide wire (and optionally the cannula) is retracted from the catheter, and the visualization element is advance into the nosecone. The element is activated at the nosecone sideport and the side port is rotated to face the vessel true lumen. The visualization element is removed, and the cannula and guide wire are re-introduced. When Method 5 is used, the side port is rotated to face the vessel true lumen per fluoroscopic visualization.

The distal tip of the guide wire is now positioned approximately 2 centimeters proximal from the distal tip of the nosecone. At this point the application of vacuum as described in (Step 2, Method 1) may be used to evacuate fluid from the sub-intimal plane and lock the sub-intimal tissue onto the surface of the nosecone.

Next, the cannula is advanced distally and guided through the internal ramp until it is brought into secure purchase with the sub-intimal tissue. The guide wire is then advanced until the tip is coincident with the cannula distal tip, such that both are in contact with the sub-intimal tissue. Utilizing the combined effects of the vacuum and the slight extension of the cannula against the sub-intimal tissue, the guide wire is then rotated and pushed to initiate a pathway through the sub-intimal tissue.

After a re-entry pathway has been formed, the cannula is advanced into the true lumen, the RF system removed, and a conventional guide wire is placed into the true lumen. Alternatively, the cannula may remain retracted in the nosecone, and the guide wire fed directly through the pathway in the sub-intimal tissue and into the true lumen.

After the guide wire has been advanced into the vessel true lumen, the cannula may then be retracted into the catheter and resume its original position.

The position of the guide wire is maintained in the vessel true lumen, and the entire catheter system is retracted from the vasculature. As the catheter is retracted proximally over the guide wire, the floppy distal end of the guide wire may be able to pass through the nosecone side port, however as the nosecone reaches the stiff mid and proximal sections of the guide wire, the guide wire must now fall through the slot connecting the side port with the end port. Therefore, as the catheter nosecone is retracted over the mid- and proximal sections of the guide wire, it does so with the guidewire traveling through the nosecone distal port.

Typical dimensions of the catheter components are as follows: outer shaft/nosecone outside diameter is approximately 0.050 to 0.060 inches; cannula element outside diameter is approximately 0.020 to 0.030 inches; and specialized guide wire outside diameter is approximately 0.010 to 0.018 inches.

Embodiment 4 (Method 3 under Step 3) (FIG. 10)

This embodiment includes a catheter having a nosecone or molded distal termination, a single lumen catheter shaft, and a specialized guide wire to be used specifically with the catheter. This guide wire will be described in detail later. The catheter shaft may be any of a number of catheter shafts known in the art. The nosecone is similar to the nosecone of FIG. 9 in that it includes a side exit port and a distal end port coupled via a slot. However, the dimensions of these features are peculiar to this design.

As previously stated, the nosecone of FIG. 10 is similar to that of FIG. 9 with the exception that the width of the side port and the outside diameter of the end port are slightly larger than the width of the connecting slot. As example dimensions, the width of the side port and the outside diameter of the end port may be approximately 0.016 inches, and the slot may be approximately 0.012 inches. The significance of these dimensions will become evident once the guide wire is dimensionally described. The internal ramp has a width approximately equal to the size of the side port. The angle of the internal ramp may also vary from approximately 30 degrees to 80 degrees, but is not necessarily limited to these angles. The distal end port of the nosecone allows the catheter to be tracked in a co-linear fashion over the specialized guide wire.

The guide wire may be fabricated using standard methods and materials known by those skilled in the art. The outside diameter over the distal most 5–8 centimeters may be approximately 0.014 inches, followed proximally by a 1–2 centimeter portion with an outside diameter of approximately 0.010 inches, followed proximally by the remainder of the guide wire with an outside diameter of approximately 0.014 inches.

Figure 35:
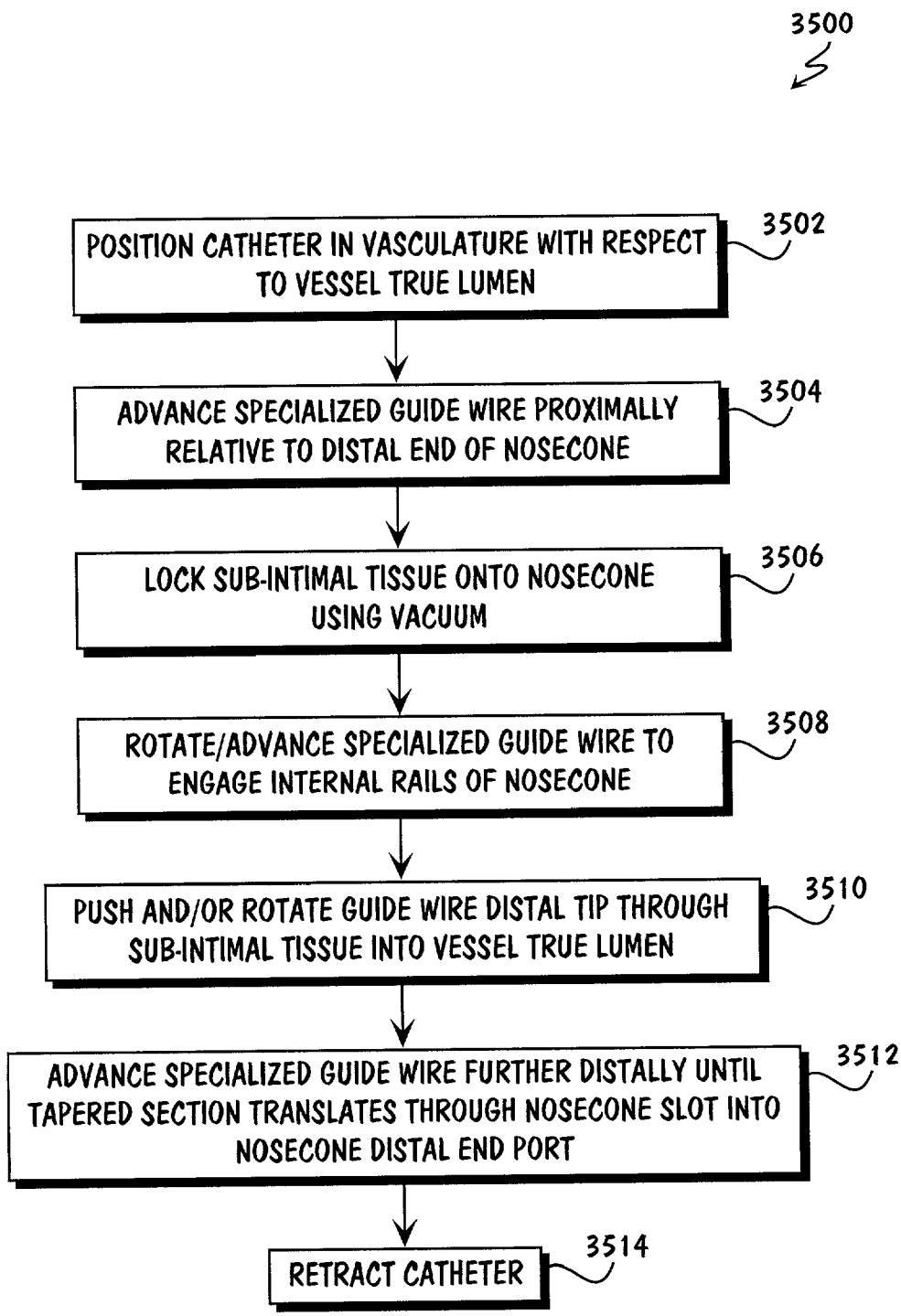
FIG. 35 is a flow diagram for using a guide wire to establish a pathway through sub-intimal tissue into a vessel true lumen, under a third alternative embodiment.

FIG. 35 is a flow diagram for using a guide wire to establish a pathway through sub-intimal tissue into a vessel true lumen, under a third alternative embodiment. Procedurally, the catheter is tracked over a standard guide wire, or over the specialized guide wire, either of which has been placed in the desired sub-intimal space of the target vasculature. If a standard guide wire is initially used, it may then be removed and the specialized guide wire advanced into the catheter.

Next, the catheter must be aligned to the vessel true lumen. This may be accomplished per Step 1 Methods 1–4, or Step 1, Method 5. In the case where Methods 1–4 are used, the guide wire is retracted from the catheter, and the visualization element is advance into the nosecone. The element is activated at the nosecone sideport and the side port is rotated to face the vessel true lumen. The visualization element is removed, and the specialized guide wire is reintroduced. In the case that Method 5 is used, the side port is rotated to face the vessel true lumen per fluoroscopic visualization.

Next, the distal tip of the specialized guide wire is positioned approximately 2 centimeters proximal from the distal tip of the nosecone. At this point the application of vacuum as described in (Step 2, Method 1) may be used to evacuate fluid from the sub-intimal plane and lock the sub-intimal tissue onto the surface of the nosecone.

The specialized guide wire is now advanced distally. Note that because the nosecone exit port is co-incident with the catheter lumen, the natural tendency of the specialized guide wire may be for it to simply pass out the distal port of the nosecone. The intent, however is to advance the specialized guide wire out of the nosecone side port. This issue is easily resolved. Prior to the introduction of any guide wire into the vasculature, the physician routinely places a small curve on the end of the guide wire to facilitate negotiating the tortuosity in the vasculature. Therefore, the specialized wire need only be rotated until the curved distal portion of the wire engages the internal rails. It may then be advanced onto the internal ramp of the side port.

The distal 5–8 centimeters of the specialized guide, at a width of approximately 0.014 inches, will advance on the two rails of the internal ramp, since the rails are separated by the 0.012-inch width of the slot, and the side port is 0.016 inches wide. The specialized guide wire is brought into contact with the sub-intimal tissue. Utilizing the effect of the vacuum, the specialized guide wire can be rotated and pushed to initiate a pathway through the sub-intimal tissue.

After the specialized guide wire has crossed to the vessel true lumen, the wire is advanced further distally. In this process, the 5–8 centimeters of distal length guide wire (0.014 inches outside diameter) continues to advance over the internal rails, until the 1 centimeter section of guide wire (0.010 inches outside diameter) reaches the distal edge of the ramp. At this point the section of guide wire having a 0.010 inch outside diameter falls through the 0.012-inch wide slot and into the 0.016-inch wide distal end port.

At this point, the distal 6–9 centimeters of the guide wire is across the sub-intimal plane and into the vessel true lumen. While maintaining the wire position in the vasculature, the catheter may now be retracted proximally along the wire, because the nosecone end port is 0.016 inches in diameter, and the proximal portion of the wire is 0.014 inches in diameter.

Typical dimensions of the catheter components are as follows: outer shaft/nosecone outside diameter is approximately 0.030 to 0.050 inches; specialized guide wire outside diameter is as described above.

Embodiment 5 (Method 3 under Step 3) (FIG. 11)

This embodiment includes a catheter having a simple nosecone or molded distal termination, and a single lumen catheter shaft. The catheter shaft may be any of a number of catheter shafts known in the art. The nosecone includes an internal ramp connecting the catheter lumen with a single side exit port. This embodiment has no distal port to track over a guide wire. This catheter can be used in conjunction with a conventional guide wire, or a specialized guide wire as described at the end of this section.

Figure 36:
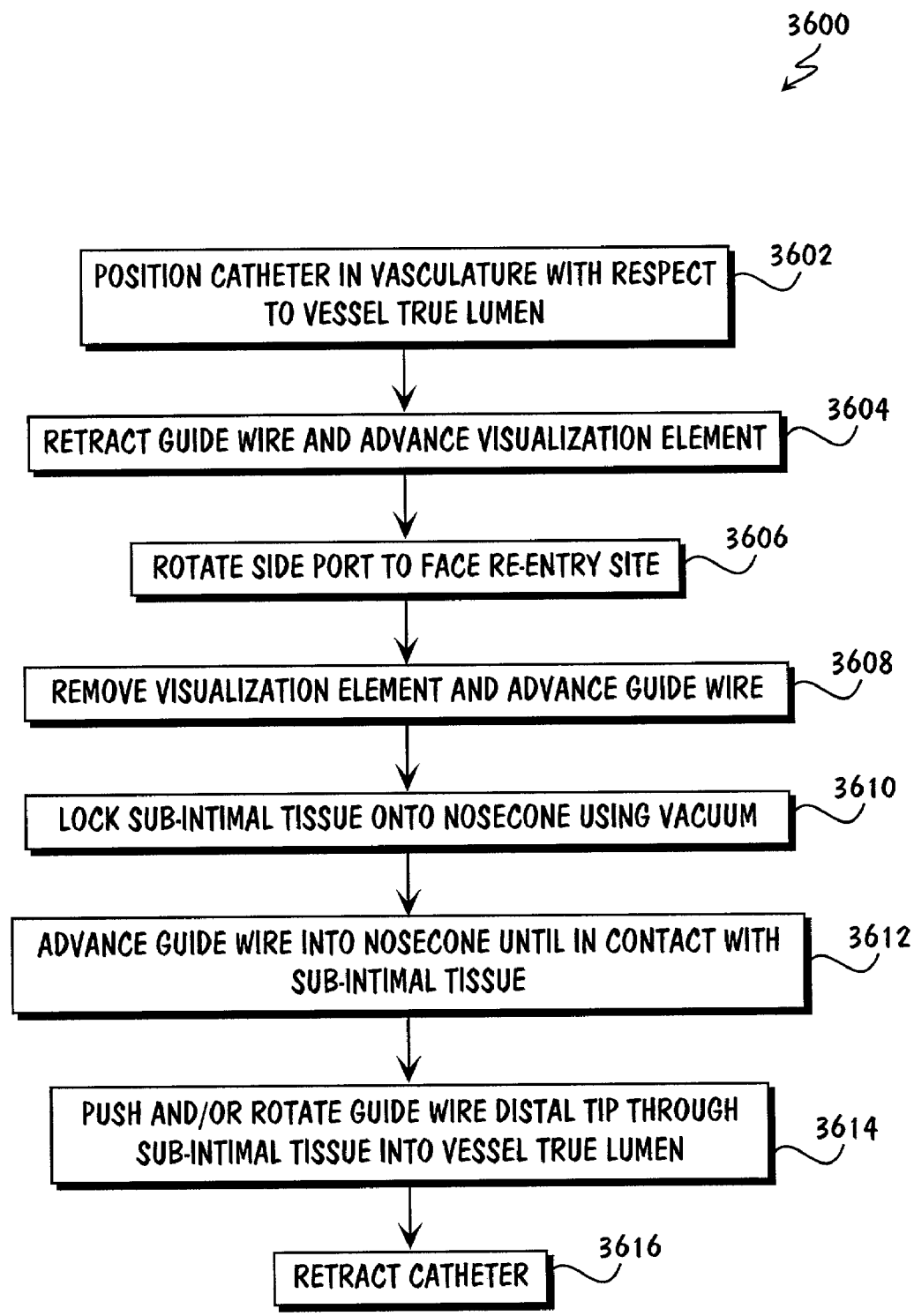
FIG. 36 is a flow diagram for using a guide wire to establish a pathway through sub-intimal tissue into a vessel true lumen, under a fourth alternative embodiment.

FIG. 36 is a flow diagram for using a guide wire to establish a pathway through sub-intimal tissue into a vessel true lumen, under a fourth alternative embodiment. Procedurally, the catheter is tracked over a standard guide wire which has been placed in the desired sub-intimal space of the target vasculature. Note that since the guide wire emerges laterally from the nosecone, the very tip of the catheter will track eccentrically over the guide wire.

Next, the catheter is aligned to the vessel true lumen. This may be accomplished per Step 1 Methods 1–4, or Step 1, Method 5. FIG. 11 shows both configurations. In the case of Methods 1–4, the guide wire is retracted from the catheter, and the visualization element is advanced into the nosecone. The element is activated at the nosecone side port and the side port is rotated to face the vessel true lumen. The visualization element is removed, and the guide wire is re-introduced. In the case of Method 5, the side port is rotated to face the vessel true lumen per fluoroscopic visualization.

Next, the distal tip of the guide wire is positioned approximately 2 centimeters proximal from the distal tip of the nosecone. At this point the application of vacuum as described in (Step 2, Method 1) may be used to evacuate fluid from the sub-intimal plane and lock the sub-intimal tissue onto the surface of the nosecone. Vacuum is translated to the nosecone via the single shaft lumen.

The guide wire is then advanced distally into the nosecone. The guide wire is brought into contact with the sub-intimal tissue at the nosecone side port at an angle determined by the exit ramp of the nosecone. The wire is then rotated and pushed in order to initiate and propagate a pathway through the sub-intimal tissue. The angle of the internal ramp may vary from approximately 30 degrees to 80 degrees, but is not necessarily limited to these angles.

After the guide wire has successfully been advanced into the vessel true lumen, the guide wire position is maintained and the catheter may be retracted proximally over the guide wire and removed from the vasculature.

Typical dimensions of the catheter components are as follows: outer shaft/nosecone outside diameter is approximately 0.030 to 0.050 inches; specialized guide wire outside diameter is approximately 0.010 to 0.018 inches.

Embodiment 6 (Method 3 under Step 3) (FIG. 12)

This embodiment includes a catheter having a nosecone or molded distal termination, a single lumen catheter shaft, and an internal slidably disposed tube the distal end of which translates within the catheter nosecone. The distal end of the push tube or member is slidably disposed within the nosecone. Upon actuation of the push member in a distal direction, a percentage of the proximal section of the nosecone side port is covered. The percentage of coverage is controlled by a distal stop within the nosecone that limits the distal translation of the internal sliding member or tube. In the case the internal sliding member is a tube, the internal sliding member becomes the guide wire lumen.

As the internal sliding member is advanced into this distal position, it reduces the effective length of the nosecone side port. This forces the guide wire to exit the side port at a more acute angle that is more normal to the axis of the catheter, and more normal to the sub-intimal tissue plane. The exit angle of the guide wire is governed by the proximal contact point against the internal sliding member, and the distal contact point against the exit ramp of the nosecone. The greater acute angle allows the guide wire to produce more force normal to the sub-intimal tissue surface, and improves the ability of the wire to establish a pathway across the sub-intimal tissue.

Figure 37:
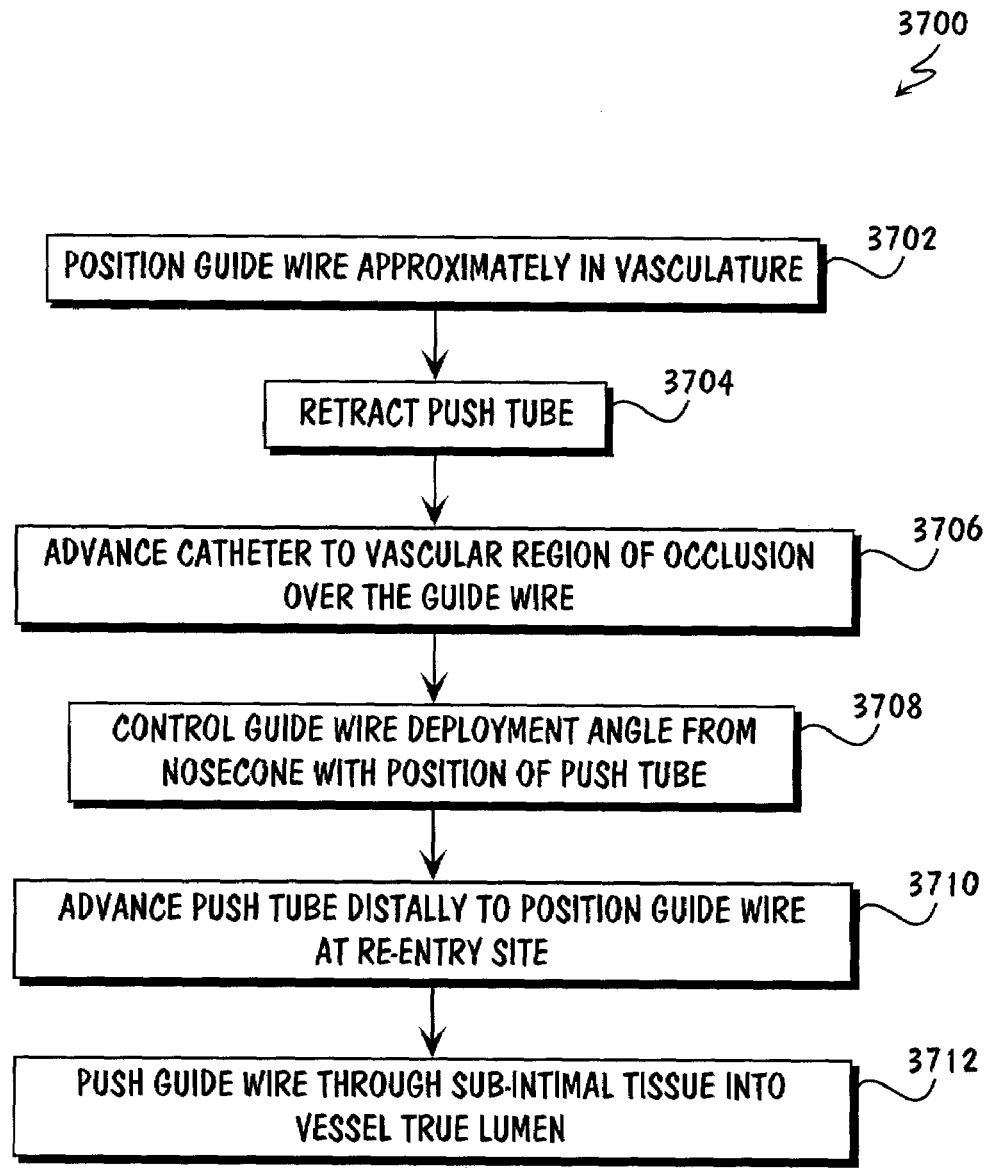
FIG. 37 is a flow diagram for using a guide wire to establish a pathway through sub-intimal tissue into a vessel true lumen, under a fifth alternative embodiment.

FIG. 37 is a flow diagram for using a guide wire to establish a pathway through sub-intimal tissue into a vessel true lumen, under a fifth alternative embodiment. Procedurally, the sliding tube may remain in the catheter at all times. In preparation of the catheter and during delivery of the catheter to the vascular site, the tube is retracted just proximal to the nosecone. Prior to the advancement of the guide wire out of the nosecone sideport, the sliding tube is advance to its distal most position, thus reducing the effective length of the nosecone sideport.

Typical dimensions of the catheter components are as follows: outer shaft/nosecone outside diameter is approximately 0.030 to 0.050 inches; internal slide tube outside diameter is approximately 0.020 to 0.030 inches; and specialized guide wire outside diameter is approximately 0.010 to 0.018 inches.

Embodiment 7 (Method 3 under Step 3) (FIG. 13)

FIG. 13 is a diagram of a single lumen catheter shaft, terminated in a "J" tip, used in conjunction with a conventional or specialized guide wire. The "J" tip configuration of the catheter is designed to be torqued into position within the sub-intimal plane and directed towards the sub-intimal tissue. The guide wire is directed at an angle normal to the sub-intimal tissue, which improves the ability of the wire to establish a pathway across the sub-intimal tissue.

The "J" termination of the catheter can be fluoroscopically visible to facilitate the positioning process in the sub-intimal plane. This type of termination may be easily fabricated or molded from fluoroscopically visible materials such as platinum coils or gold coated stainless steel coils laminated with a variety of polymers, e.g. nylons, HDPE, or Pebax. The "J" tip is designed to straighten in order to track over a guide wire to the vascular site, yet re-form its shape when positioned in the vasculature, and the guide wire is retracted. A visualization window may be incorporated just proximal to the "J" tip to be used in conjunction with an on-board visualization technique, per Step 1, Methods 1–4. For the use of IVUS, for example, this window may be fabricated from HDPE.

Figure 38:
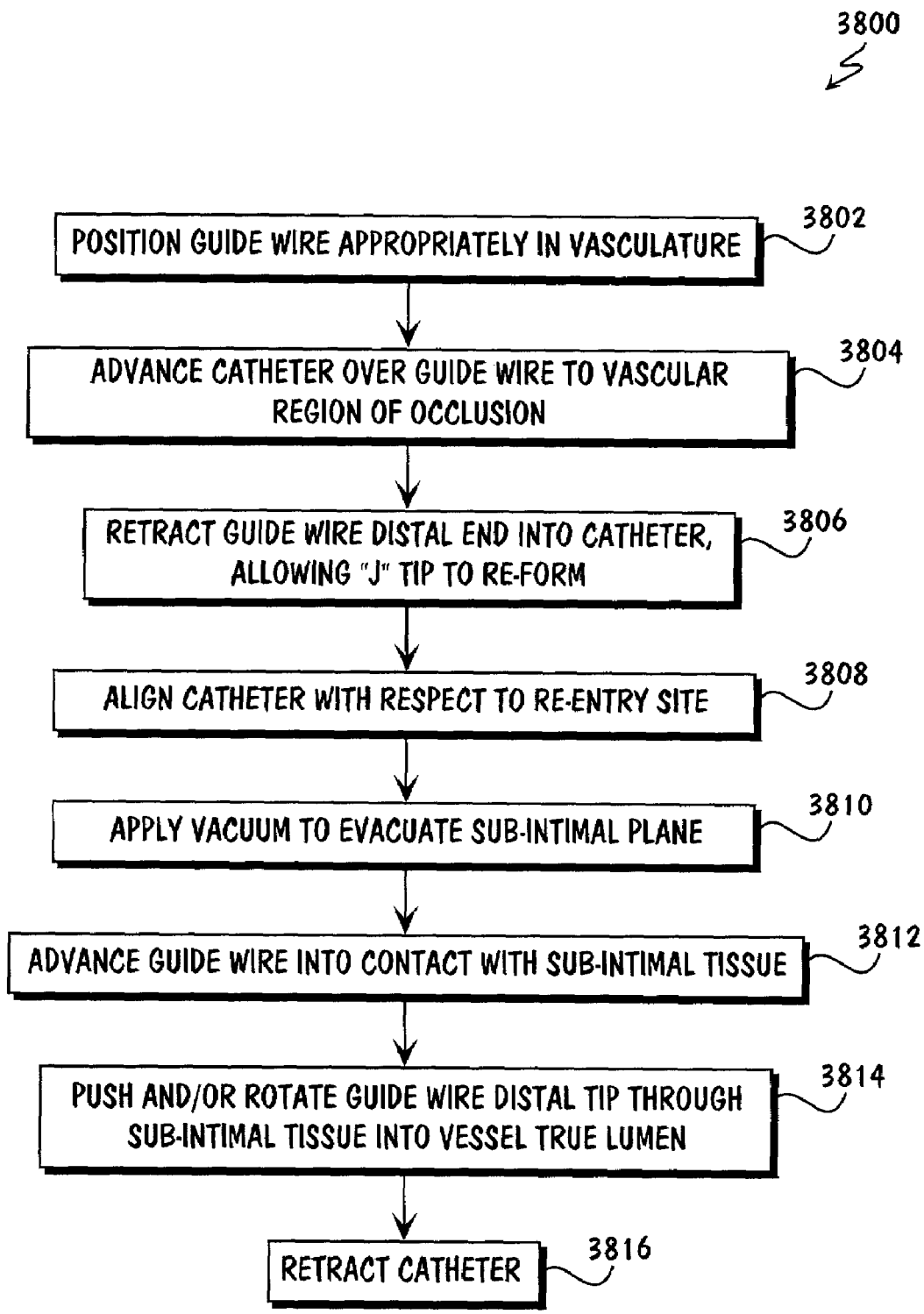
FIG. 38 is a flow diagram for using a guide wire to establish a pathway through sub-intimal tissue into a vessel true lumen, under a sixth alternative embodiment.

FIG. 38 is a flow diagram for using a guide wire to establish a pathway through sub-intimal tissue into a vessel true lumen, under a sixth alternative embodiment. Procedurally, a guide wire is positioned in the sub-intimal space. The distal end of the catheter is loaded onto the guide wire. In this process the "J" tip is straightened as it tracks over the wire and to the sub-intimal site. Once the terminal end of the catheter has reached the desired location, the guide wire is retracted, allowing the "J" tip to re-form.

The catheter is now aligned to the vessel true lumen. This may be accomplished per Step 1 Methods 1–4, or Step 1, Method 5. FIG. 13 shows both configurations. In the case of Methods 1–4, the guide wire is retracted from the catheter, and the visualization element is advanced to the visualization window. The visualization element is activated at the window and the "J" tip is rotated to face the vessel true lumen. The visualization element is removed, and the guide wire is re-introduced. In the case of Method 5, the side port is rotated to face the vessel true lumen per fluoroscopic visualization.

Next, vacuum may be applied through the catheter lumen per Step 2, method 1 to evacuate the sub-intimal plane. The guide wire is then advanced until it is brought into contact with the sub-intimal tissue. Procedurally, the wire is then pushed or rotated as required in order to initiate and propagate a pathway through the sub-intimal tissue and into the vessel true lumen. Once the guide wire has established a pathway through the sub-intimal tissue, the wire position is maintained, and the catheter is retracted, leaving the distal portion of the wire positioned in the vessel true lumen.

Typical dimensions of the catheter components are as follows: single lumen shaft outside diameter is approximately 0.030 to 0.050 inches; specialized guide wire outside diameter is approximately 0.010 to 0.018 inches.

Embodiment 8 (Method 3 under Step 3) (FIG. 14)

This embodiment includes a catheter having a nosecone or molded distal termination, an internal push-ramp which is actuated by an internal push tube or member, and a single lumen catheter shaft. The push ramp may be constructed of a flexible metal such as Nitinol or spring steel, or a polymer such as nylon or PEEK, any of which fabricated with or without appropriate detents to allow for bending, as required. The distal end of the push ramp is connected or hinged in some fashion about the internal distal termination of the catheter shaft, opposite the side port. When the push tube or member is fully retracted proximally, the push ramp assumes a linear configuration, lying essentially flat against the inside wall of the catheter, opposite the nosecone side port. When the push tube or member is advanced distally, the push ramp forms an incline that leads from the proximal end of the ramp, opposite the nosecone side port, to the distal end of the side port. This ramp will re-direct the guide wire out of the nosecone side port as it is advanced distally in the catheter.

This catheter system may be used with any of the visualization techniques of Step 1.

Figure 39:
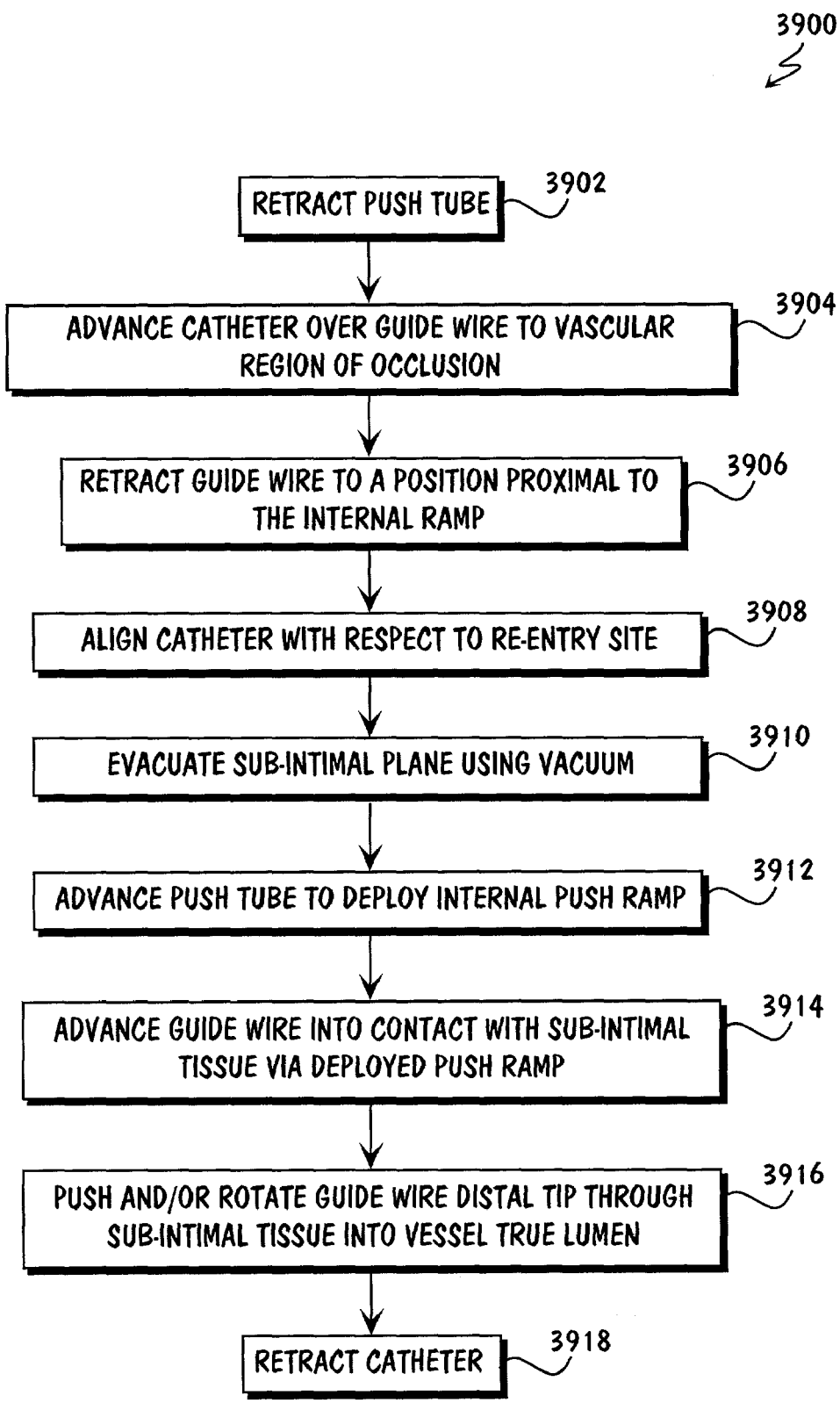
FIG. 39 is a flow diagram for using a guide wire to establish a pathway through sub-intimal tissue into a vessel true lumen, under a seventh alternative embodiment.

FIG. 39 is a flow diagram for using a guide wire to establish a pathway through sub-intimal tissue into a vessel true lumen, under a seventh alternative embodiment. Procedurally, a guide wire is positioned in the sub-intimal space. The pull tube or member is retracted proximally, and the distal end of the catheter is loaded onto the guide wire. Once the terminal end of the catheter has reached the desired location, the guide wire is retracted just proximal to the proximal portion of the ramp.

The catheter is aligned to the vessel true lumen. This may be accomplished per Step 1 Methods 1–4, or Step 1, Method 5. FIG. 13 shows both configurations. In the case of Methods 1–4, the guide wire is retracted from the catheter, and the visualization element is advanced to the visualization window. The visualization element is activated at the nosecone sideport and the sideport is rotated to face the vessel true lumen. The visualization element is removed, and the guide wire is re-introduced. In the case of Method 5, the side port is rotated to face the vessel true lumen per fluoroscopic visualization.

Next, vacuum may be applied through the catheter lumen per Step 2, method 1 to evacuate the sub-intimal plane. The push tube or member is then advanced distally to urge the push ramp into its hinged configuration. The guide wire is then advanced distally, following the ramp to the nosecone cone port until it is brought into contact with the sub-intimal tissue. Procedurally, the wire is then pushed or rotated as required in order to initiate and propagate a pathway through the sub-intimal tissue and into the vessel true lumen. Once the guide wire has established a pathway through the sub-intimal tissue, the wire position is maintained and the catheter is retracted, leaving the distal portion of the wire positioned in the vessel true lumen.

Typical dimensions of the catheter components are as follows: outer shaft/nosecone outside diameter is approximately 0.030 to 0.050 inches; internal push tube outside diameter is approximately 0.020 to 0.030 inches; and specialized guide wire outside diameter is approximately 0.010 to 0.018 inches.

Embodiment 9 (Method 3 under Step 3) (FIG. 15)

This embodiment includes a dual lumen catheter shaft terminating in a single lumen "J" tip, and is used in conjunction with a conventional or specialized guide wire. This dual lumen catheter has the same "J" type single lumen distal termination as described in Method 3, Embodiment 7, with the exception that it transitions proximally to a dual lumen catheter shaft. Fabrication and materials for the "J" tip are as stated in Method 3, Embodiment 7. The dual lumen catheter shaft may be fabricated using standard materials and methods known to those skilled in the art. Only one of the slidably disposed elements contained within either lumen can be advanced individually into the "J" tip single lumen, as required by the procedure. The "J" tip may accommodate only one element at any time.

For example, one lumen may contain the guide wire while the other lumen may be used to deliver various elements to the vascular site, e.g. visualization elements per Step 1, Methods 1–4, or other types of re-entry elements such as a wire with a stiff distal tip which could be used only to pierce a hole through the sub-intimal tissue, but would be too stiff to be advanced into the vessel true lumen.

Figure 40:
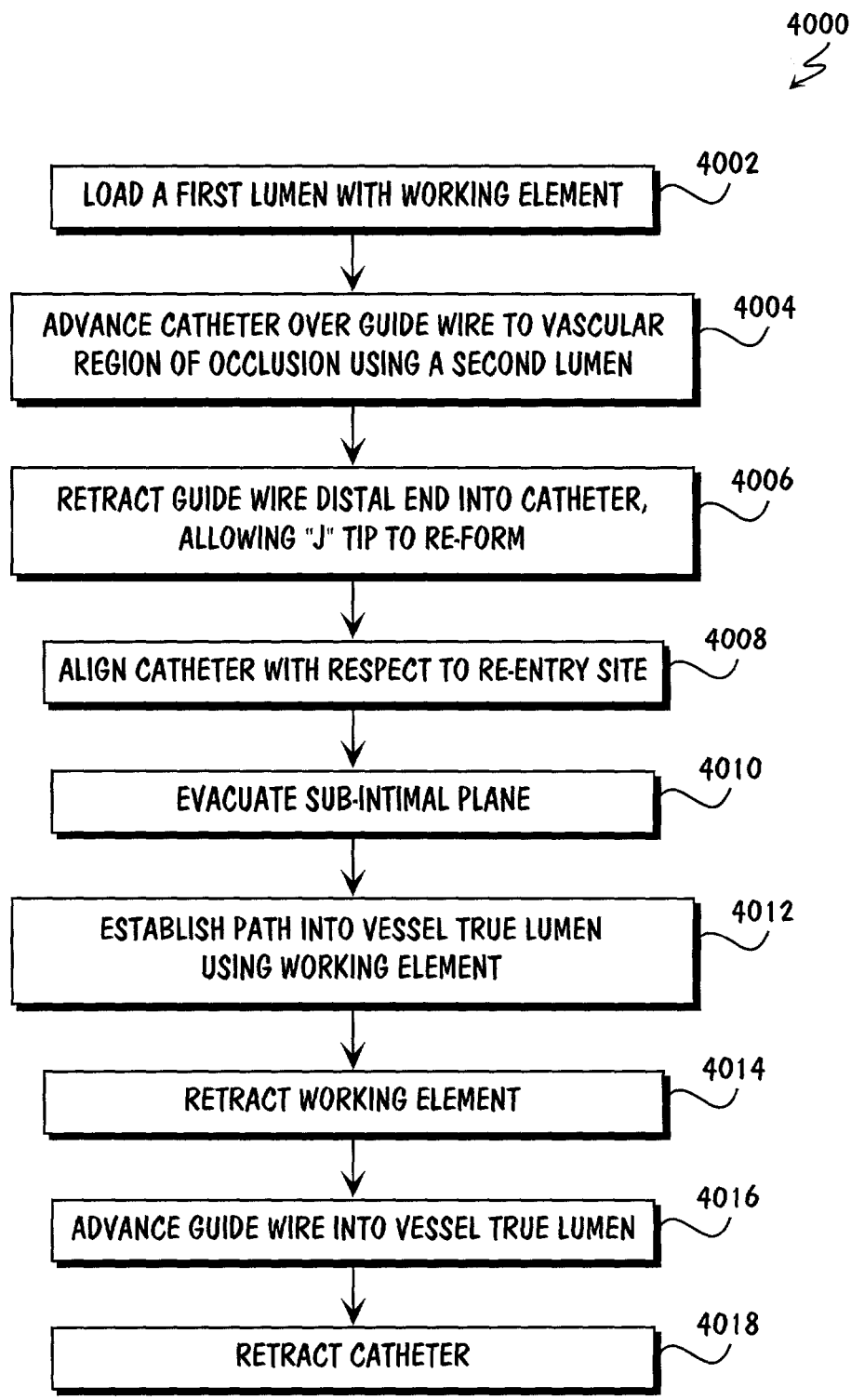
FIG. 40 is a flow diagram for using a guide wire to establish a pathway through sub-intimal tissue into a vessel true lumen, under an eighth alternative embodiment.

FIG. 40 is a flow diagram for using a guide wire to establish a pathway through sub-intimal tissue into a vessel true lumen, under an eighth alternative embodiment. In a first scenario, the first lumen of the dual lumen contains a standard guide wire and the second lumen contains a re-entry wire or re-entry element to pierce or otherwise establish a pathway into the vessel true lumen. Procedurally, one lumen is loaded with a re-entry wire or element and advanced just proximal to the entrance to the single distal lumen.

The distal end of the catheter is then loaded onto a standard guide wire which has been advanced into a sub-intimal plane. The catheter is advanced to the desired vascular location, and the guide wire withdrawn just proximal to the entrance to the single lumen. The catheter is now aligned to the vessel true lumen. This embodiment would make use of Step 1, Method 5 to align the catheter.

The sub-intimal plane is now evacuated per Step 2, Method 2. Next, the guide wire or re-entry element is advanced into the "J" tip and manipulated to establish a pathway through the sub-intimal plane and into the vessel true lumen. The re-wire or re-entry element is retracted out of the single lumen. The standard guide wire may then be advanced into the distal single lumen, and out of the "J" tip, through the pathway produced in the sub-intimal tissue, and into the vessel true lumen. Lastly, the guide wire is held in place while the catheter is retracted proximally and removed from the vasculature.

Figure 41:
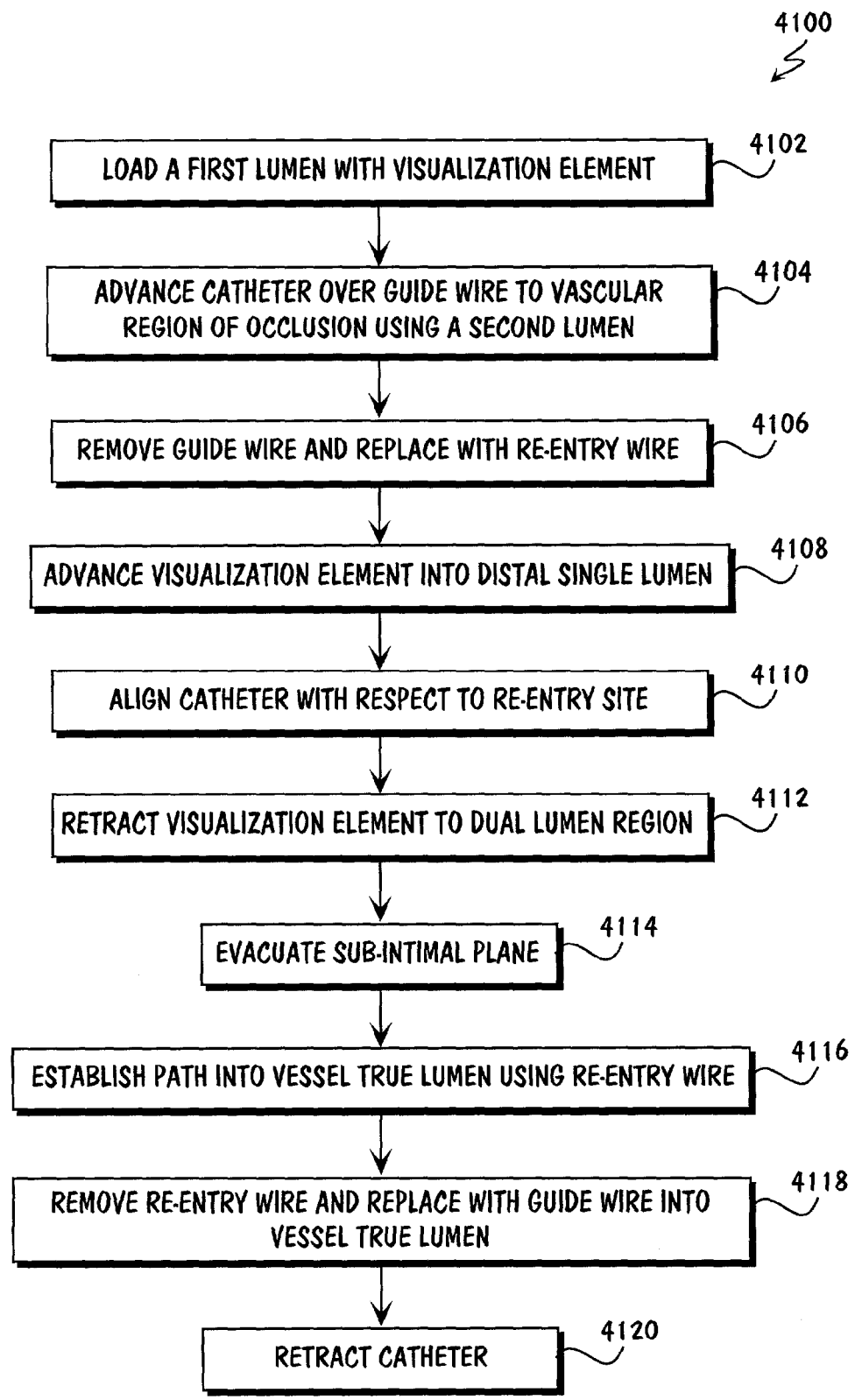
FIG. 41 is a flow diagram for using a guide wire to establish a pathway through sub-intimal tissue into a vessel true lumen, under a ninth alternative embodiment.

FIG. 41 is a flow diagram for using a guide wire to establish a pathway through sub-intimal tissue into a vessel true lumen, under a ninth alternative embodiment. In a second scenario, the first lumen of the dual lumen contains a visualization element, per Step 1, Method 1–4, and the second lumen contains a re-entry wire to establish a pathway into the vessel true lumen.

Procedurally, one lumen is loaded with the visualization element and advanced proximal to the entrance to the distal single lumen. The distal end of the catheter is then loaded onto a standard guide wire that has been advanced into a sub-intimal plane. The catheter is advanced to the desired vascular location, the guide wire is removed from the catheter and replaced with the re-entry wire. Next the visualization element is advanced into the distal single lumen within the area of the window for viewing, and the "J" tip is aligned with the vessel true lumen. The visualization element is then withdrawn to within the dual lumen portion of the shaft.

The sub-intimal plane is now evacuated per Step 2, Method 2. This is best accomplished through the lumen which houses the visualization element because the visualization element need not be translated proximally/distally through the proximal hemostasis seal for the remainder of the procedure. Next, the re-entry wire is advanced into the "J" tip and manipulated to establish a pathway through the sub-intimal tissue and into the vessel true lumen. The re-entry wire is retracted and replaced with the guide wire, and the guide wire is held in place while the catheter is retracted proximally and removed from the vasculature.

In a third scenario, all steps are similar to the second scenario, with the exception that a stiff re-entry wire or element is used to establish the pathway through the sub-intimal tissue, and is then replaced by a standard guide wire and advanced into the vessel true lumen before removal of the catheter.

Typical dimensions of the catheter components are as follows: single lumen shaft outside diameter is approximately 0.030 to 0.050 inches; dual lumen shaft is approximately 0.030 to 0.050 inches (each lumen); and specialized guide wire outside diameter is approximately 0.010 to 0.018 inches.

Method 4 under Step 3: Radio Frequency (RF) Energy (FIGS. 5, 6, 7, 9, 11 through 15, and 18)

This method describes the application of radio frequency (RF) energy to ablate a select section of sub-intimal tissue to create a path into the true lumen. The RF energy can be delivered as continuous with an unspecified duration. Alternatively, the RF energy may be gated such that it is defined by a predetermined duration, e.g., 5–50 milliseconds.

Two separate modes of application of RF energy may be employed, unipolar or bi-polar. Both methods may be employed in all embodiments described herein.

In a unipolar configuration, a single active electrode (or a group of common electrodes) is located at a distal position of the re-entry catheter. The active electrode(s) may be contained on the outside surface of the catheter, or within the distal nosecone or distal termination of the catheter, such that a communication path exists to the outside of the catheter. The placement of the active electrode(s) is such that when the catheter is aligned to the vessel true lumen per Step 1, the electrode(s) faces the sub-intimal tissue to be ablated. A second grounding electrode is external to the patient and placed against the patient's buttocks. The surface area of the grounding electrode is very large with respect to the catheter active electrode.

As RF energy is applied between the catheter active electrode(s) and the grounding electrode, a closed circuit is established from one electrode to the other, through the patients body tissue. The energy density (RF power) and duration is adjusted to ablate only the sub-intimal tissue that separates the dissection plane from the vessel true lumen. As the RF energy travels between the catheter electrode(s) and the grounding electrode, the energy density decreases significantly such that immediately peripheral to the volume of sub-intimal tissue to be ablated, the energy density is insufficient to affect the surrounding vessel structure or other body tissues.

In a bipolar configuration both the active electrode and the grounding electrode are contained at the distal portion of the catheter. One or both can be mounted on the outside surface of the catheter, or within the catheter itself. Both electrodes are intended to be of similar size, although exact size and configuration may vary to meet the overall design requirements of the re-entry catheter system. The placement of the electrodes is such that when the catheter is aligned to the vessel true lumen per Step 1, the sub-intimal tissue to be ablated completes the circuit between electrodes.

As RF energy is applied between the catheter electrodes, a closed circuit is established from one electrode to the other, co-linear with the sub-intimal tissue plane that separates the dissection plane from the vessel true lumen. The energy density (RF power) and duration is adjusted to ablate the sub-intimal tissue that separates the dissection plane from the vessel true lumen. Unlike the unipolar technique described above, the energy density between the two bipolar electrodes is relatively constant, and only the sub-intimal tissue along the path between the two electrodes is ablated. It is surmised that the bipolar mode may have more accurate control over tissue ablation than the unipolar configuration.

Embodiment 1 (Method 4 under Step 3) (FIGS. 5 through 7A)

This embodiment includes a catheter having a nosecone or molded distal termination, an internal visualization element, and one or more RF electrodes. In this embodiment the single lumen catheter shaft is terminated by a formed nosecone having a sideport for imaging the sub-intimal tissue and locating the vessel true lumen, and an endport for tracking the catheter over a guide wire. The nosecone is also shown with one or more RF electrodes, suitable to embody either the unipolar or bipolar configuration.

Figure 42:
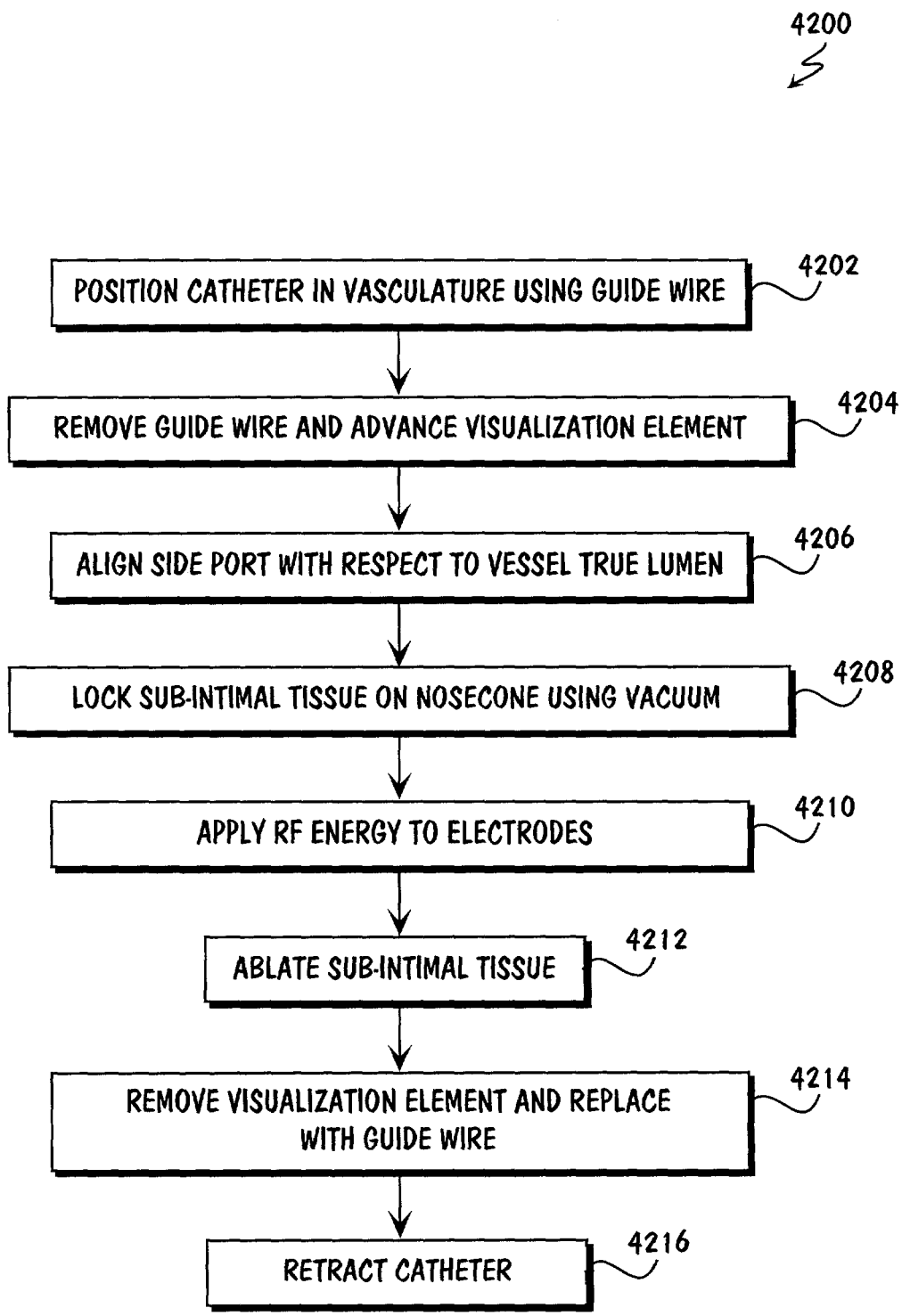
FIG. 42 is a flow diagram for establishing a path into a vessel true lumen using radio frequency (RF) energy, under an embodiment.

FIG. 42 is a flow diagram for creating a path into a vessel true lumen using radio frequency (RF) energy, under an embodiment. Procedurally, the visualization element is removed from the catheter (FIG. 5 and 6 only), and the catheter is loaded onto a guide wire that has been advanced into a sub-intimal plane. The catheter is tracked to the vascular site, and the guide wire is removed. The visualization element is loaded into the catheter, and advanced into the nosecone sideport. The visualization element is activated and the sideport is directed towards the vessel true lumen.

Next, vacuum is applied within the catheter lumen per Step 1, Method 1 to secure the sub-intimal tissue to the nosecone, and bring the sub-intimal tissue into contact with the RF electrodes. Next, RF energy may be applied to the electrodes as required to ablate the sub-intimal tissue and form a pathway into the vessel true lumen.

If the sub-intimal tissue is thick, it may be advantageous to invaginate more sub-intimal tissue into the nosecone by retracting the visualization element and continuously applying vacuum per Step 2, Method 2. This enhances the likelihood of ablating the volume of sub-intimal tissue necessary to establish a pathway into the true lumen.

As addressed in the beginning of this Method, RF energy may be applied in the unipolar configuration to one or more of the electrodes mounted on the catheter, treating the electrodes as a common pole with respect to the grounding plate. Alternatively, in the bipolar configuration, the RF signal may be applied to one of the catheter mounted electrodes, using the other as the ground return.

The visualization element is removed (FIG. 5 and 6 only), and a standard guide wire is introduced either through the nosecone end port or side port into the vessel true lumen.

Typical dimensions of the catheter components are as follows: outer shaft/nosecone outside diameter is approximately 0.040 to 0.060 inches; imaging element outside diameter is as described in Step 1 above.

Embodiment 2 (Method 4 under Step 3) (FIG. 9)

This embodiment includes a nosecone or molded catheter termination attached to the distal end of the catheter, an internal slidably disposed actuating cannula, and an element slidably disposed in the cannula which contains distal electrodes.

Figure 43:
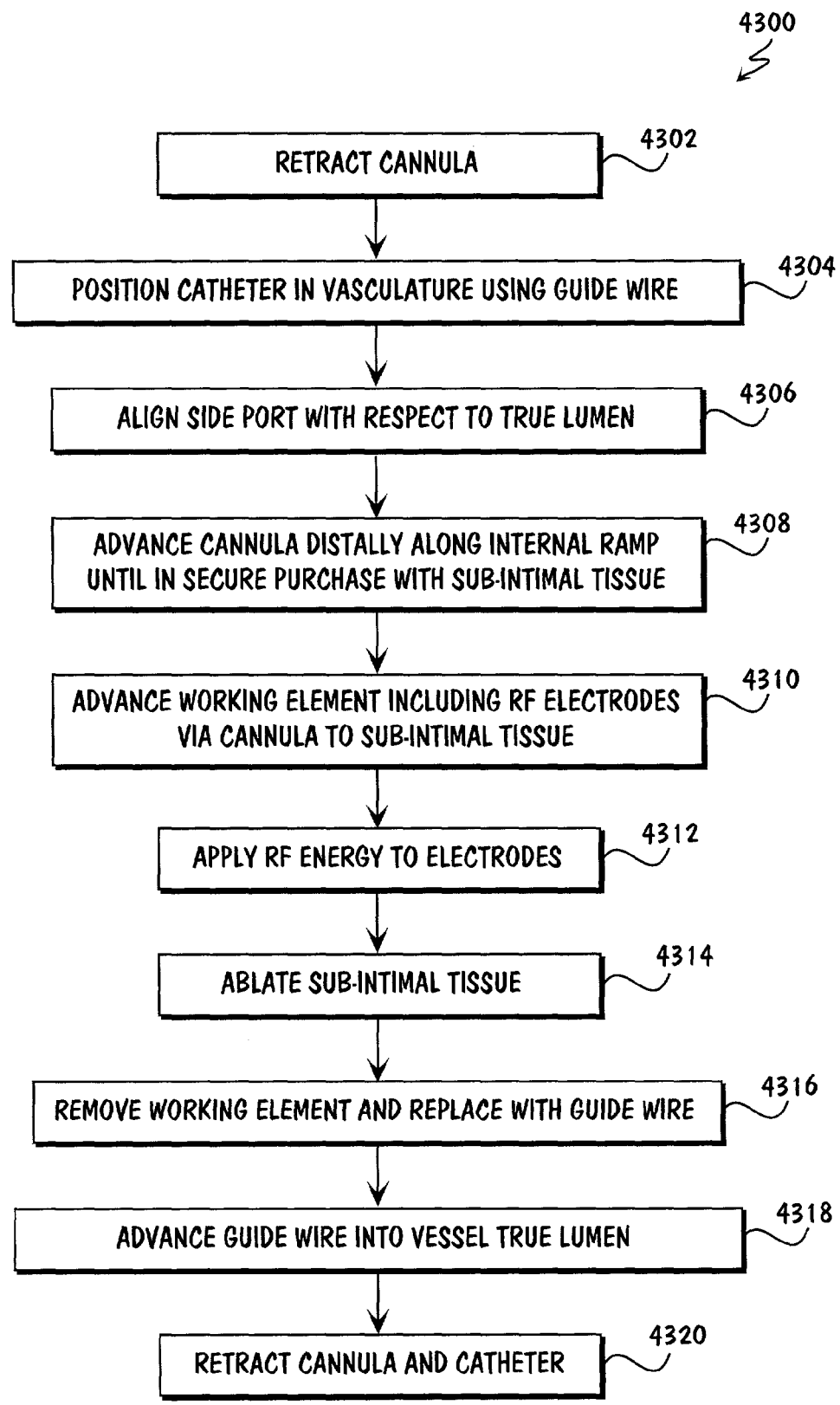
FIG. 43 is a flow diagram for establishing a path into a vessel true lumen using RF energy, under a first alternative embodiment.

FIG. 43 is a flow diagram for creating a path into a vessel true lumen using radio frequency (RF) energy, under a first alternative embodiment. This embodiment is essentially similar to that of Method 3, Embodiment 3 with the exception that in place of the guide wire, an element is delivered inside the cannula which contains one or more electrodes to ablate the sub-intimal tissue.

Typical dimensions of the catheter components are as follows: single lumen shaft outside diameter is approximately 0.030 to 0.050 inches; cannula element outside diameter is approximately 0.020 to 0.030 inches; and RF element outside diameter is approximately 0.015 to 0.020 inches.

Embodiment 3 (Method 4 under Step 3) (FIG. 11)

This embodiment includes a catheter having a simple nosecone or molded distal termination, a single lumen catheter shaft and an element slidably disposed in the catheter which contains distal electrodes.

Figure 44:
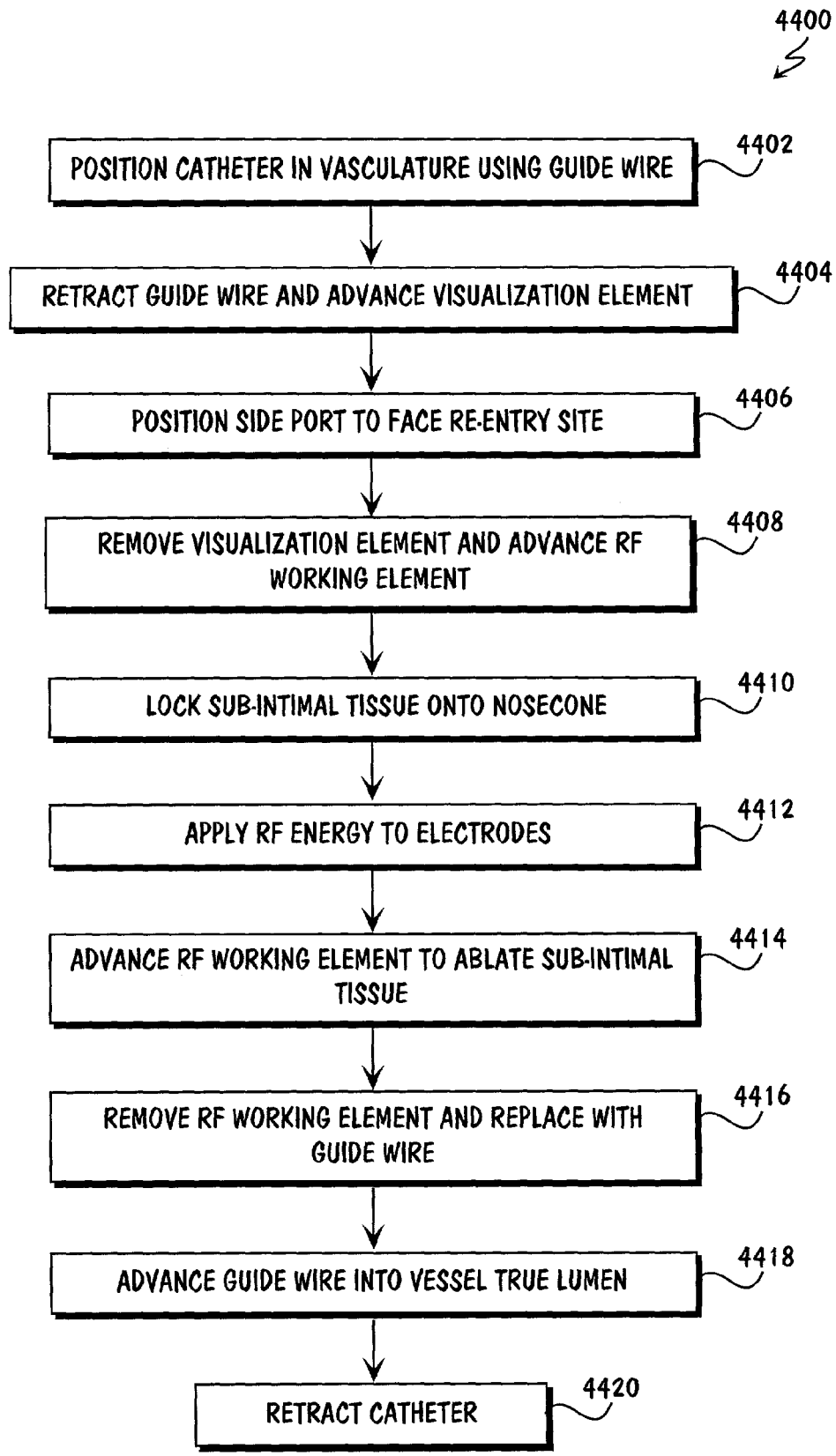
FIG. 44 is a flow diagram for establishing a path into a vessel true lumen using RF energy, under a second alternative embodiment.

FIG. 44 is a flow diagram for creating a path into a vessel true lumen using radio frequency (RF) energy, under a second alternative embodiment. Procedurally, this embodiment is essentially similar to that of Method 3, Embodiment 5 with the exception that in place of the guide wire, an element is delivered inside the catheter which contains one or more distal electrodes to ablate the sub-intimal tissue.

After a pathway has been established through the sub-intimal tissue, the slidably disposed element is removed from the catheter, and a standard guide wire is advanced into the vessel true lumen.

Typical dimensions of the catheter components are as follows: outer shaft/nosecone outside diameter is approximately 0.030 to 0.050 inches; and RF element outside diameter is approximately 0.015 to 0.020 inches.

Embodiment 4 (Method 4 under Step 3) (FIG. 12)

This embodiment includes a catheter having a simple nosecone or molded distal termination, a single lumen catheter shaft, an internal slidably disposed tube, and an element slidably disposed in the tube which contains distal electrodes.

Figure 45:
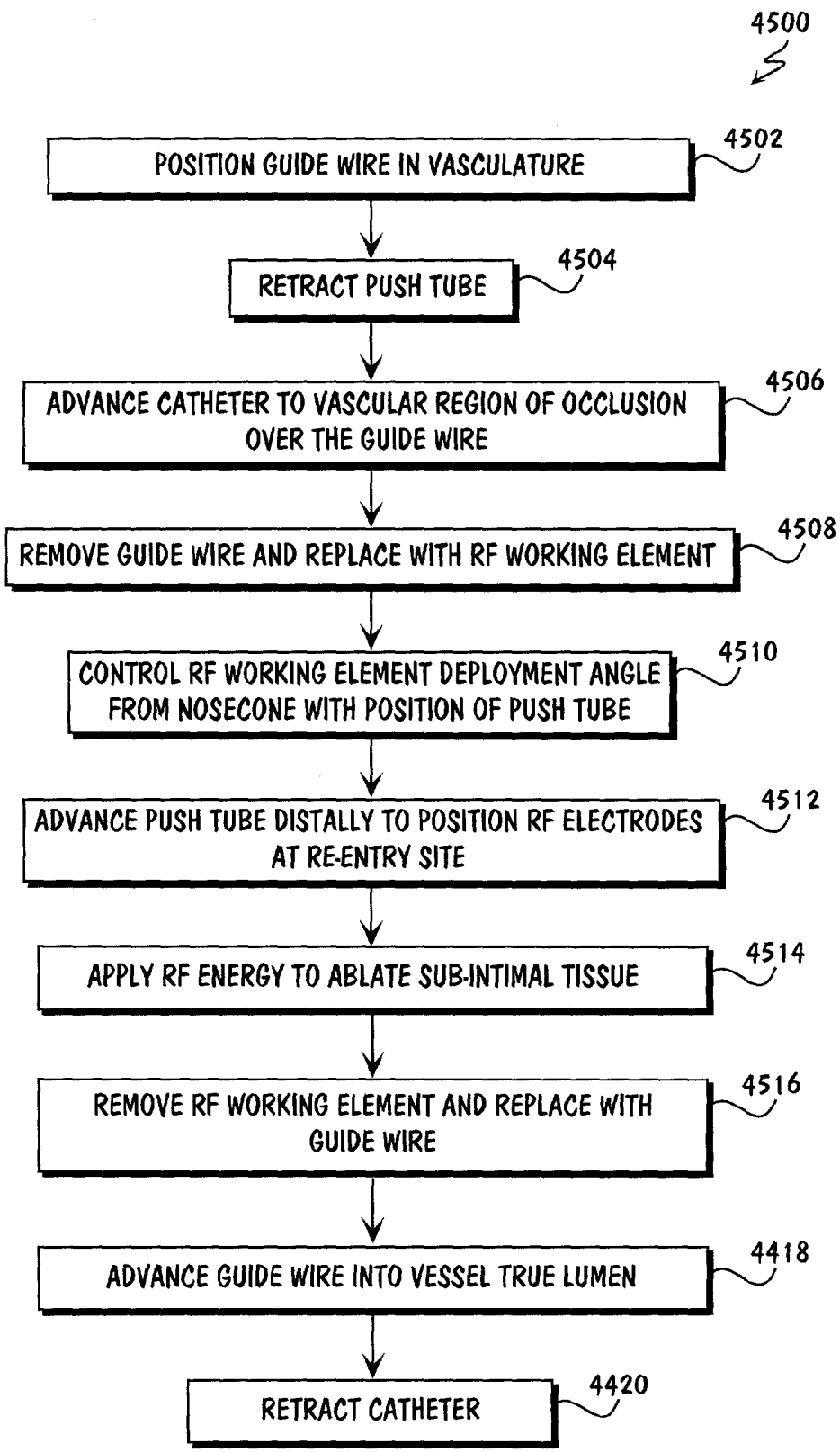
FIG. 45 is a flow diagram for establishing a path into a vessel true lumen using RF energy, under a third alternative embodiment.

FIG. 45 is a flow diagram for creating a path into a vessel true lumen using radio frequency (RF) energy, under a third alternative embodiment. Procedurally, this embodiment is essentially similar to that of Method 3, Embodiment 6, with the exception that in place of the guide wire, a slidably disposed element is used which contains one or more electrodes to ablate the sub-intimal tissue.

After a pathway has been established through the sub-intimal tissue, the slidably disposed element is removed from the catheter, and a standard guide wire is advanced into the vessel true lumen.

Typical dimensions of the catheter components are as follows: outer shaft/nosecone outside diameter is approximately 0.030 to 0.050 inches; internal slide tube outside diameter is approximately 0.020 to 0.030 inches; and RF element outside diameter is approximately 0.015 to 0.020 inches.

Embodiment 5 (Method 4 under Step 3) (FIG. 13)

This embodiment includes a single lumen catheter shaft, terminated in a "J" tip, used in conjunction with an element slidably disposed in the catheter which contains distal electrodes. Procedurally, this embodiment is used in a similar fashion to Method 3, Embodiment 7. In this embodiment, and with further reference to FIG. 38, the slidably disposed element contains one or more electrodes to ablate the sub-intimal tissue, and takes the place of the guide wire.

After a pathway has been established through the sub-intimal tissue, the slidably disposed element is removed from the catheter, and a standard guide wire is advanced into the vessel true lumen Typical dimensions of the catheter components are as follows: single lumen shaft outside diameter is approximately 0.030 to 0.050 inches; and RF element outside diameter is approximately 0.015 to 0.020 inches.

Embodiment 6 (Method 4 under Step 3) (FIG. 14)

This embodiment includes a catheter having a nosecone or molded distal termination, an internal push-ramp which is actuated by an internal push tube or member, an element slidably disposed in the catheter which contains distal electrodes and a single lumen catheter shaft.

Procedurally, this embodiment is used in a similar fashion to Method 3, Embodiment 8. In this embodiment, and with further reference to FIG. 39, the slidably disposed element contains one or more electrodes to ablate the sub-intimal tissue, and takes the place of the guide wire.

After a pathway has been established through the sub-intimal tissue, the slidably disposed element is removed from the catheter, and a standard guide wire is advanced into the vessel true lumen Typical dimensions of the catheter components are as follows: outer shaft/nosecone outside diameter is approximately 0.030 to 0.050 inches; internal push tube outside diameter is approximately 0.020 to 0.030 inches; and RF element outside diameter is approximately 0.015 to 0.020 inches.

Embodiment 7 (Method 4 under Step 3) (FIG. 15)

Describes a dual lumen catheter shaft, terminated in a single lumen "J" tip, used in conjunction with an element slidably disposed in the catheter which contains distal electrodes. Procedurally, this embodiment is used in a similar fashion to Method 3, Embodiment 9. In this embodiment, and with further reference to FIGS. 40 and 41, the slidably disposed element contains one or more electrodes to ablate the sub-intimal tissue, and takes the place of the guide wire.

After a pathway has been established through the sub-intimal tissue, the slidably disposed element is removed from the catheter, and a standard guide wire is advanced into the vessel true lumen Typical dimensions of the catheter components are as follows: single lumen shaft outside diameter is approximately 0.030 to 0.050 inches; dual lumen shaft outside diameter is approximately 0.030 to 0.050 inches (each lumen); and RF element outside diameter is approximately 0.015 to 0.020 inches.

Method 5 under Step 3: Laser Energy (FIGS. 4, 7 through 15; and 17)

This method describes the application of laser energy to ablate the sub-intimal tissue that separates the dissection plane from the vessel true lumen. In the following embodiments, optical fiber(s) is/are contained within the catheter, such that the terminal end of the optical fiber(s) is/are positioned to deliver laser energy to ablate the sub-intimal tissue.

In the following embodiments, the optical fiber element may comprise: a single optical fiber contained within a protective sheath such as polyimide or high density polyethelene; a bundle of optical fibers collectively protected by a sheath such as polyimide, or high density polyethelene; or an optical fiber bundle arranged in an annular fashion, such that the interior of the bundle is an open lumen sized to accommodate a standard guide wire. In this embodiment, the optical fibers may be arranged in the annular fashion within a polymer extrusion. The extrusion design thus encases the fibers in the annular arrangement, provides a lumen within the extrusion for the passage of a guide wire, and provides an outer smooth surface, such that the fiber optic bundle may be translated within a catheter lumen. These optical fiber embodiments are shown in FIG. 16.

Embodiment 1 (Method 5 under Step 3) (FIG. 4)

This embodiment includes a distal nosecone or molded shaft termination and dual lumen catheter shaft. A first lumen of the catheter shaft houses the imaging element, per Step 1, Method 1–4, and a second lumen houses the optical fiber system or a guide wire.

This embodiment allows simultaneous visualization of the true lumen and sub-intimal tissue, while delivering laser energy via the optical fiber system to ablate the sub-intimal tissue. In operation, small volumes of sub-intimal tissue are sequentially ablated with each pulsed delivery of optical energy, until a pathway has been established. The exit angle from the nosecone of the lumen which houses the optical fiber system is approximately in the range of 20 degrees to 90 degrees, but is not necessarily limited to these angles.

The termination of the optical fiber may be normal to the axis of the optical fiber, such that the exit angle is zero degrees with respect to the optical fiber. Alternatively, the termination of the optical fiber may be angled with respect to the axis to provide total internal reflection of the light, such that the light emerges at an angle to the axis of the optical fiber. The angle termination provides a greater overall exit angle of the laser light, when combined with the angle by which the optical fiber exits the corresponding lumen, and provides overall operational flexibility.

Figure 46:
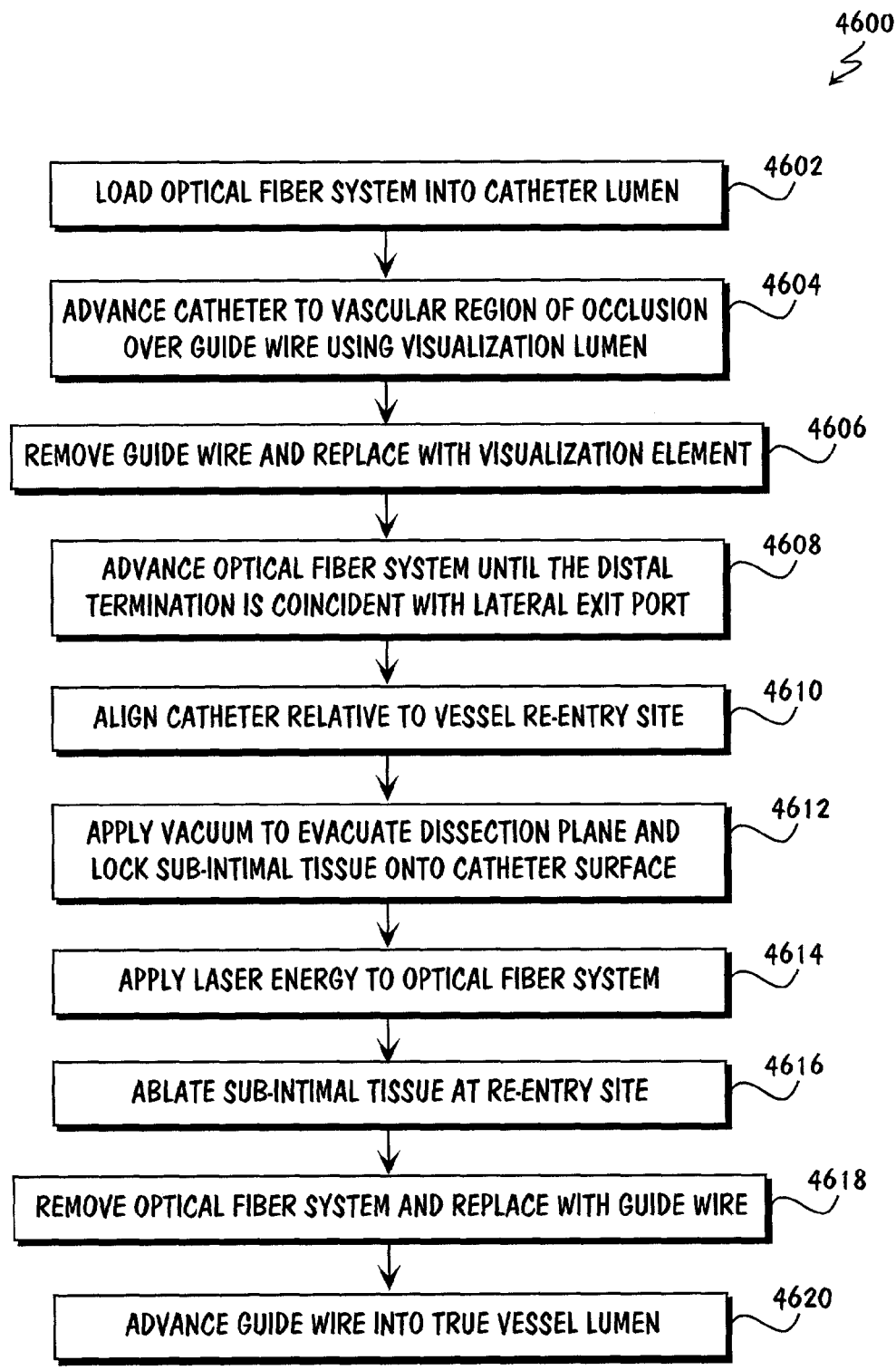
FIG. 46 is a flow diagram for establishing a path into a vessel true lumen using laser energy, under an embodiment.

FIG. 46 is a flow diagram for creating a path into a vessel true lumen using laser energy, under an embodiment. Procedurally, prior to introducing the catheter into the vasculature, the optical fiber system is loaded into a lumen, and the visualization element is removed from the catheter. Using the visualization lumen, the catheter is loaded onto a guide wire that has been advanced into a sub-intimal plane, and the catheter is advanced to the desired vascular site. In this configuration, the catheter tracks on the wire in a co-linear fashion.

The guide wire is next removed from the catheter and the visualization element is advanced in the same lumen until it is properly positioned at the distal end of the catheter. The optical fiber system is advanced until the distal termination is coincident with the lateral exit port at the nosecone.

Next, the visualization element is activated and the catheter is properly aligned to the vessel true lumen. Note that the pathway from the visualization element to the tissue may be through the shaft material itself. In the case of IVUS, this type of visualization may "see" through HDPE, and thus is the preferred material for the dual lumen shaft, the visualization element lumen, and the guide wire lumen. Alternatively, other visualization methods, e.g., Doppler, fiber optic, and OCT may require a "window" from the visualization lumen to view the tissue.

Vacuum is now applied per Step 2, Method 1, evacuating the dissection plane and locking the sub-intimal tissue onto the surface of the catheter. Vacuum may be applied through the visualization element lumen, the optical fiber lumen, or both lumens.

Laser energy is delivered to the optical fiber system as required to ablate the sub-intimal tissue which separates the dissection plane from the vessel true lumen. If the fiber optic system that does not incorporate the guide wire is used, the fiber optic system is removed and a standard guide wire is introduced for advancement through the pathway in the sub-intimal tissue and into the true lumen. In the case of the fiber optic system that contains a guide wire lumen, a guide wire is simply advanced through the lumen, through the pathway in the sub-intimal tissue, and into the true lumen.

Typical dimensions of the catheter components are as follows: outer shaft/nosecone outside diameter is approximately 0.050 to 0.070 inches; fiber optic system outside diameter is approximately 0.010 to 0.030 inches; and imaging element outside diameter is as described in Step 1 above.

Embodiment 2 (Method 5 under Step 3) (FIGS. 7 and 8)

The embodiment of FIG. 7 includes a distal nosecone and a muti-lumen catheter shaft which house a visualization element per Methods 1–4 under Step 1, an optical fiber system, and optional separate vacuum ports. The embodiment of FIG. 8 includes optional sub-intimal tissue forceps.

Figure 47:
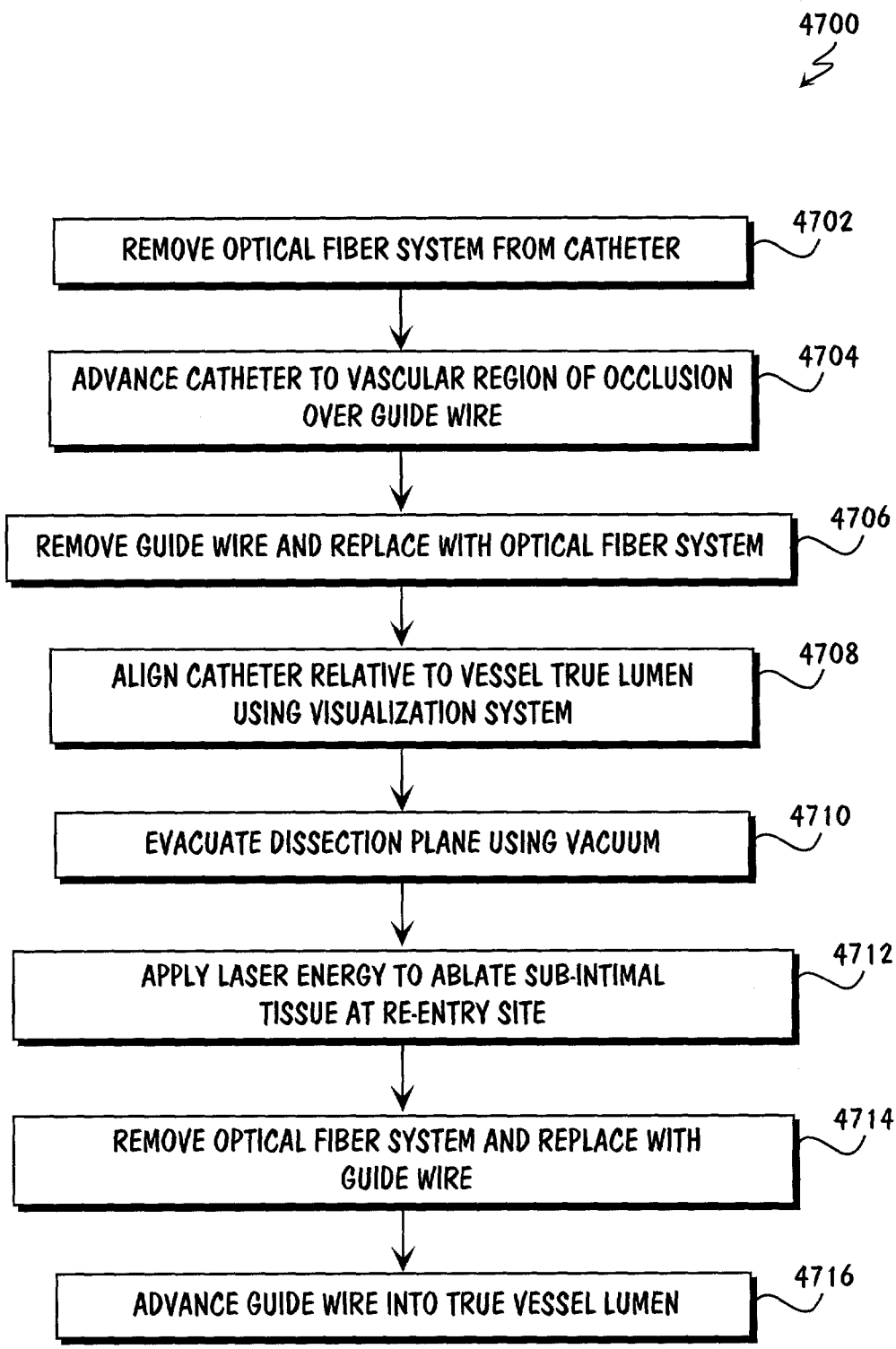
FIG. 47 is a flow diagram for establishing a path into a vessel true lumen using laser energy, under a first alternative embodiment.

FIG. 47 is a flow diagram for creating a path into a vessel true lumen using laser energy, under a first alternative embodiment. Prior to the introduction of the catheter into the vasculature, the optical fiber system is removed from a corresponding lumen. The catheter is tracked over a guide wire within this lumen to the desired sub-intimal location. Once the catheter is properly advanced in the sub-intimal plane, the guide wire is removed and the optical fiber system is replaced.

The visualization element is now activated and the catheter is properly aligned to the vessel true lumen. Next, vacuum may be applied per Step 2, Method 2, thereby evacuating the dissection plane and invaginating the sub-intimal tissue into the catheter nosecone or distal termination. Note that vacuum may be applied through the fiber optic lumen, the visualization element lumen, or through optional vacuum ports like those shown in FIGS. 7 and 8.

While maintaining alignment to the vessel true lumen, the visualization element may be retracted proximally into the catheter shaft, making more room for the sub-intimal tissue to be invaginated into the nosecone. This may be desired in the case that the sub-intimal tissue is thick, and requires a deeper purchase in order to create a pathway into the vessel true lumen. FIG. 8 is a similar embodiment showing optional forceps or skewers holding the sub-intimal tissue.

Next, laser energy is delivered to the optical fiber system as required to ablate the sub-intimal tissue that separates the dissection plane from the vessel true lumen. If a fiber optic system that does not incorporate the guide wire is used, the fiber optic system is removed and a standard guide wire is introduced for advancement through the pathway in the sub-intimal tissue and into the true lumen. In the case of the fiber optic system that contains a guide wire lumen, a guide wire is simply advanced through the lumen, through the pathway in the sub-intimal tissue, and into the true lumen.

Typical dimensions of the catheter components are as follows: outer shaft/nosecone outside diameter is approximately 0.050 to 0.060 inches; fiber optic system outside diameter is approximately 0.010 to 0.030 inches; and imaging element outside diameter is as described in Step 1 above.

Embodiment 3 (Method 5 under Step 3) (FIG. 9)

This embodiment includes a nosecone or molded catheter termination attached to the distal end of the catheter, an internal slidably disposed actuating cannula, and an optical fiber system.

The catheter shaft may be any of a number of catheter shafts known in the art. The nosecone includes a side exit port and a distal end port coupled via a slot which, and as is described below, allows the guide wire to translate or move from the side port into the distal end port when the catheter is retracted proximally over the guide wire. The cannula is guided out of the nosecone sideport via an internal exit ramp. The cannula tip of an embodiment is bluntly terminated, but is not so limited. The angle of the internal ramp may vary from approximately 30 degrees to 80 degrees, but is not necessarily limited to these angles. The distal end port of the nosecone allows the catheter to be tracked in a co-linear fashion over a standard coronary guide wire. Representative component dimensions of an embodiment are as follows: side port width is approximately 0.027 inches; slot width and distal port width are both approximately 0.016 inches; and cannula outside diameter is approximately 0.025 inches and inside diameter is approximately 0.016 inches. Note that the internal ramp is the same width as the side port.

Figure 48:
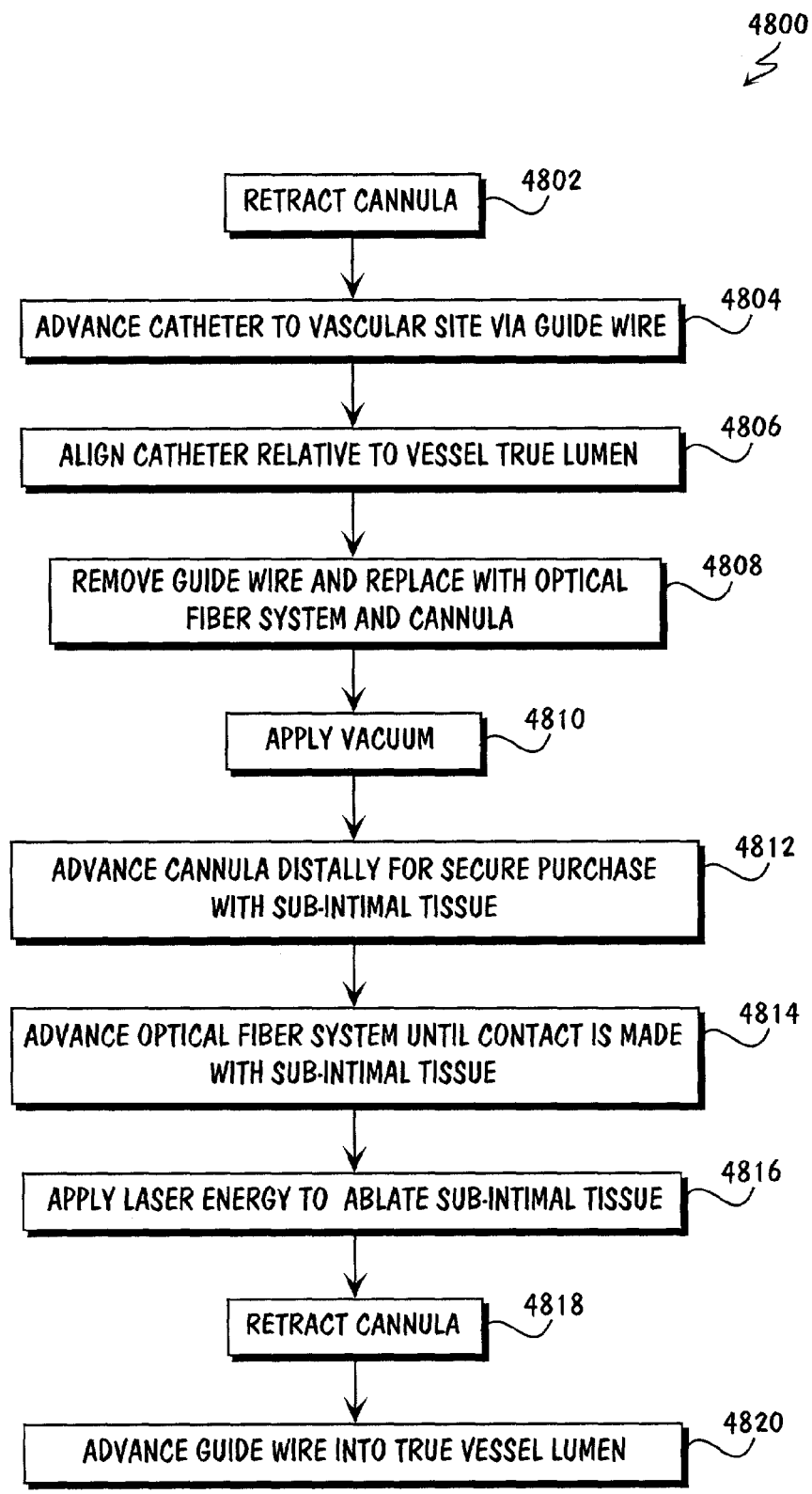
FIG. 48 is a flow diagram for establishing a path into a vessel true lumen using laser energy, under a second alternative embodiment.

FIG. 48 is a flow diagram for creating a path into a vessel true lumen using laser energy, under a second alternative embodiment. Procedurally, a guide wire is placed in the sub-intimal space of the target vasculature such that the guide wire distal end is located distal to the occluded area of the vessel. The cannula is retracted to a position proximal to the exit ramp so that the cannula exit port is co-linear with the inner diameter of the nosecone. This configuration allows the proximal end of the guide wire to be passed through the nosecone distal end port, the cannula and the catheter shaft. Thus the catheter may be tracked over the guide wire to the vascular site.

Next, the catheter is aligned to the vessel true lumen. This may be accomplished per under Step 1, Methods 1–4 or Step 1, Method 5. In the scenario where any of Methods 1–4 are used, the guide wire (and optionally the cannula) is retracted from the catheter, and the visualization element is advance into the nosecone. The element is activated at the nosecone side port and the side port is rotated to face the vessel true lumen. The visualization element is then removed. When using Method 5, the side port is rotated to face the vessel true lumen per fluoroscopic visualization. The guide wire is then removed.

The cannula and fiber optic system are re-introduced. The distal tip of the optical fiber system is positioned approximately 2 centimeters proximal from the distal tip of the nosecone. At this point, the application of vacuum can be used to evacuate fluid from the sub-intimal plane and lock the sub-intimal tissue onto the surface of the nosecone.

Next, the cannula is advanced distally and guided through the internal ramp until it is brought into secure purchase with the sub-intimal tissue. The optical fiber system is then advanced until the tip is coincident with the cannula distal tip such that both are in contact with the sub-intimal tissue.

Laser energy is now delivered to the optical fiber system as required to ablate the sub-intimal tissue that separates the dissection plane from the vessel true lumen. If the fiber optic system that does not incorporate the guide wire is used, the fiber optic system is removed and a standard guide wire is introduced for advancement through the pathway in the sub-intimal tissue and into the true lumen. In the case of the fiber optic system that contains a guide wire lumen, a guide wire is advanced through the lumen, through the pathway in the sub-intimal tissue, and into the true lumen. The cannula is subsequently retracted to its original position, so that its distal end is positioned just proximal to the nosecone internal ramp.

The position of the guide wire is maintained in the vessel true lumen, and the entire catheter system is retracted from the vasculature. As the catheter is retracted proximally over the guide wire, the floppy distal end of the guide wire may be able to pass through the nosecone side port. However as the nosecone reaches the stiff mid and proximal sections of the guide wire, the guide wire falls through the slot connecting the side port with the end port. Therefore, as the catheter nosecone is retracted over the mid- and proximal sections of the guide wire, it does so with the guide wire traveling through the nosecone distal port.

Typical dimensions of the catheter components are as follows: single lumen shaft outside diameter is approximately 0.030 to 0.050 inches; cannula element outside diameter is approximately 0.020 to 0.030 inches; and fiber optic system outside diameter is approximately 0.010 to 0.030 inches.

Embodiment 4 (Method 5 under Step 3) (FIG. 11)

This embodiment includes a catheter having a simple nosecone or molded distal termination, a single lumen catheter shaft, and a fiber optic system slidably disposed in the catheter lumen. The catheter shaft can be any of a number of catheter shafts known in the art. The nosecone includes an internal ramp connecting the catheter lumen with a single side exit port. This design has no distal port to track over a guide wire. The fiber optic system is as described above.

Figure 49:
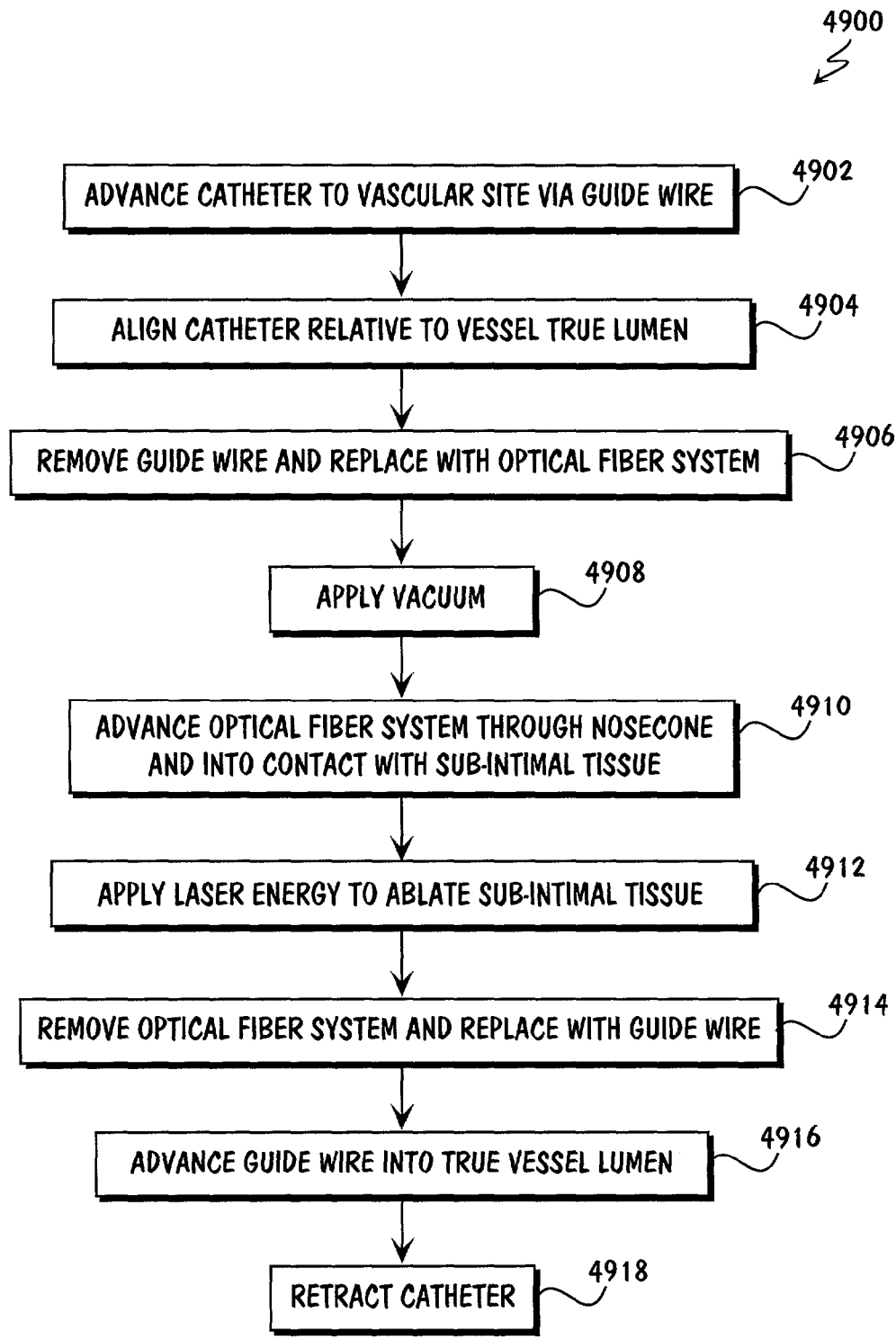
FIG. 49 is a flow diagram for establishing a path into a vessel true lumen using laser energy, under a third alternative embodiment.

FIG. 49 is a flow diagram for creating a path into a vessel true lumen using laser energy, under a third alternative embodiment. Procedurally, the optical fiber system is removed from the catheter and the catheter is tracked over a standard guide wire placed in the desired sub-intimal space of the target vasculature. Because the guide wire emerges laterally from the nosecone, the tip of the catheter will track eccentrically over the guide wire.

The catheter is aligned to the vessel true lumen in accordance with Step 1, Methods 1–4 or Step 1, Method 5 above. In the case of Methods 1–4, the guide wire is retracted from the catheter, and the visualization element is advanced into the nosecone. The element is activated at the nosecone side port and the side port is rotated to face the vessel true lumen. The visualization element is removed, and the fiber optic system is re-introduced. When Method 5 is used the side port is rotated to face the vessel true lumen per fluoroscopic visualization.

The distal tip of the fiber optic system is now positioned approximately 2 centimeters proximal from the distal tip of the nosecone. At this point the application of vacuum as described above may be used to evacuate fluid from the sub-intimal plane and lock the sub-intimal tissue onto the surface of the nosecone. Vacuum is translated to the nosecone via the single shaft lumen.

Next, the fiber optic system is advanced distally into the nosecone. The fiber optic system is brought into contact with the sub-intimal tissue at the nosecone side port at an angle determined by the exit ramp of the nosecone. The angle of the internal ramp may vary from approximately 30 degrees to 80 degrees, but is not necessarily limited to these angles.

Next, laser energy is delivered to the optical fiber system as required to ablate the sub-intimal tissue separating the dissection plane from the vessel true lumen. If the fiber optic system does not incorporate the guide wire, the fiber optic system is removed and a standard guide wire is introduced for advancement through the pathway in the sub-intimal tissue and into the true lumen. In the case of the fiber optic system including a guide wire lumen, a guide wire is simply advanced through the lumen, through the pathway in the sub-intimal tissue, and into the true lumen.

The vacuum is now released, the guide wire position is maintained, and the catheter is retracted from the vasculature, leaving the distal portion of the guide wire in place in the vessel true lumen.

Typical dimensions of the catheter components are as follows: outer shaft/nosecone outside diameter is approximately 0.030 to 0.050 inches; and fiber optic system outside diameter is approximately 0.010 to 0.030 inches.

Embodiment 5 (Method 5 under Step 3) (FIG. 12)

This embodiment includes a catheter having a simple nosecone or molded distal termination, a single lumen catheter shaft, an internal slidably disposed tube, and a fiber optic system which is slidably disposed in the internal tube. The distal end of the push tube or member is slidably disposed within the catheter shaft and nosecone. Upon actuation of the push member in a distal direction, a percentage of the proximal section of the nosecone side port becomes covered. The percentage of coverage is controlled by a distal stop within the nosecone that limits the distal translation of the internal sliding member or tube. When the internal sliding member is a tube, it becomes the lumen for both the fiber optic system and guide wire.

As the internal sliding member advances into the distal position, it reduces the effective length of the nosecone side port and forces the fiber optic system or guide wire to exit the side port at a more acute angle, or an angle that is more normal to the axis of the catheter, and more normal to the sub-intimal tissue plane. This angle is governed by the proximal contact point which is against the internal sliding member, and the distal contact point which is against the exit ramp of the nosecone. The greater acute angle is designed to allow the laser energy to ablate a more direct and efficient pathway across the sub-intimal tissue.

Figure 50A:
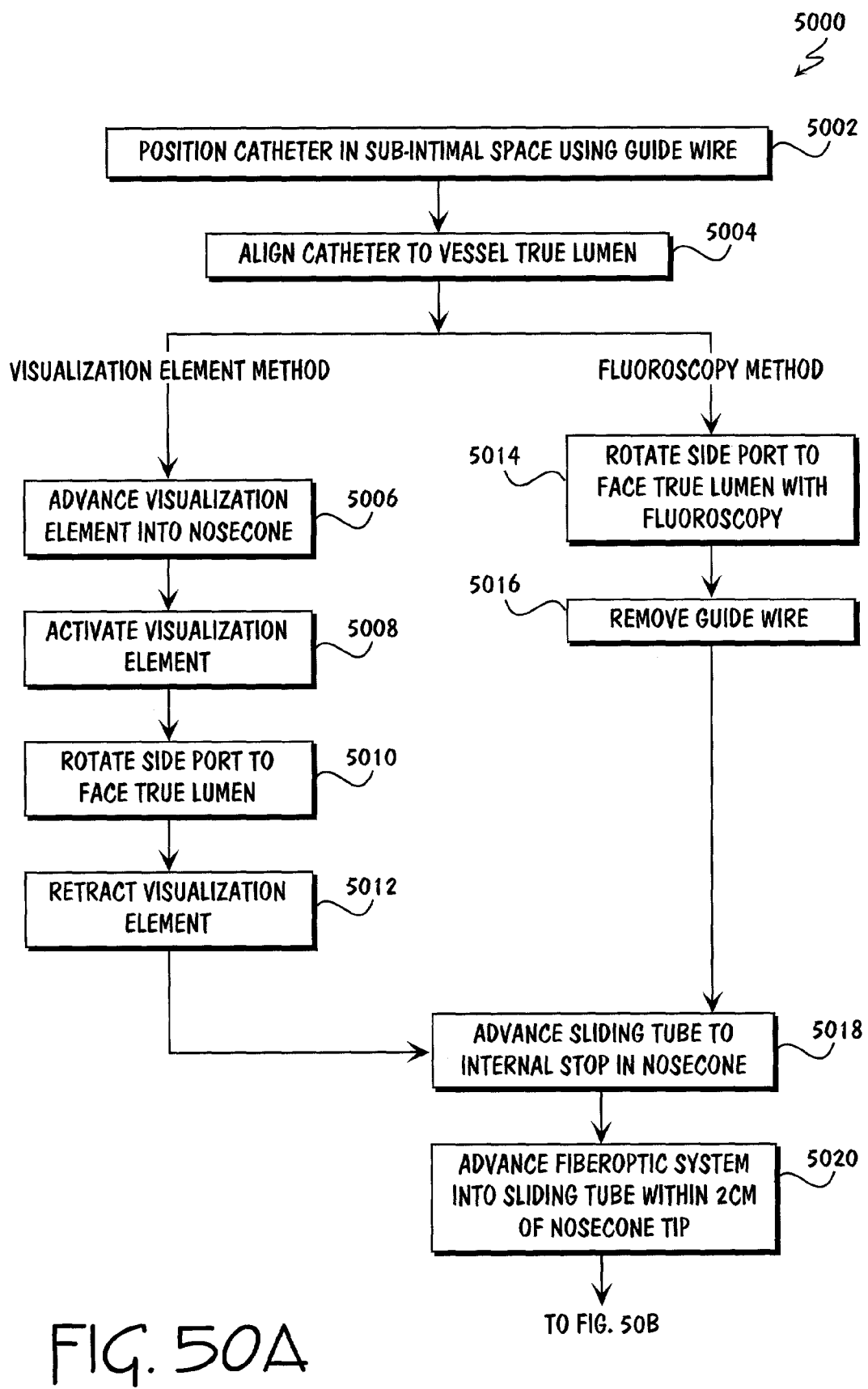
FIGS. 50A and 50B are a flow diagram for establishing a path into a vessel true lumen using laser energy, under a fourth alternative embodiment.
Figure 50B:
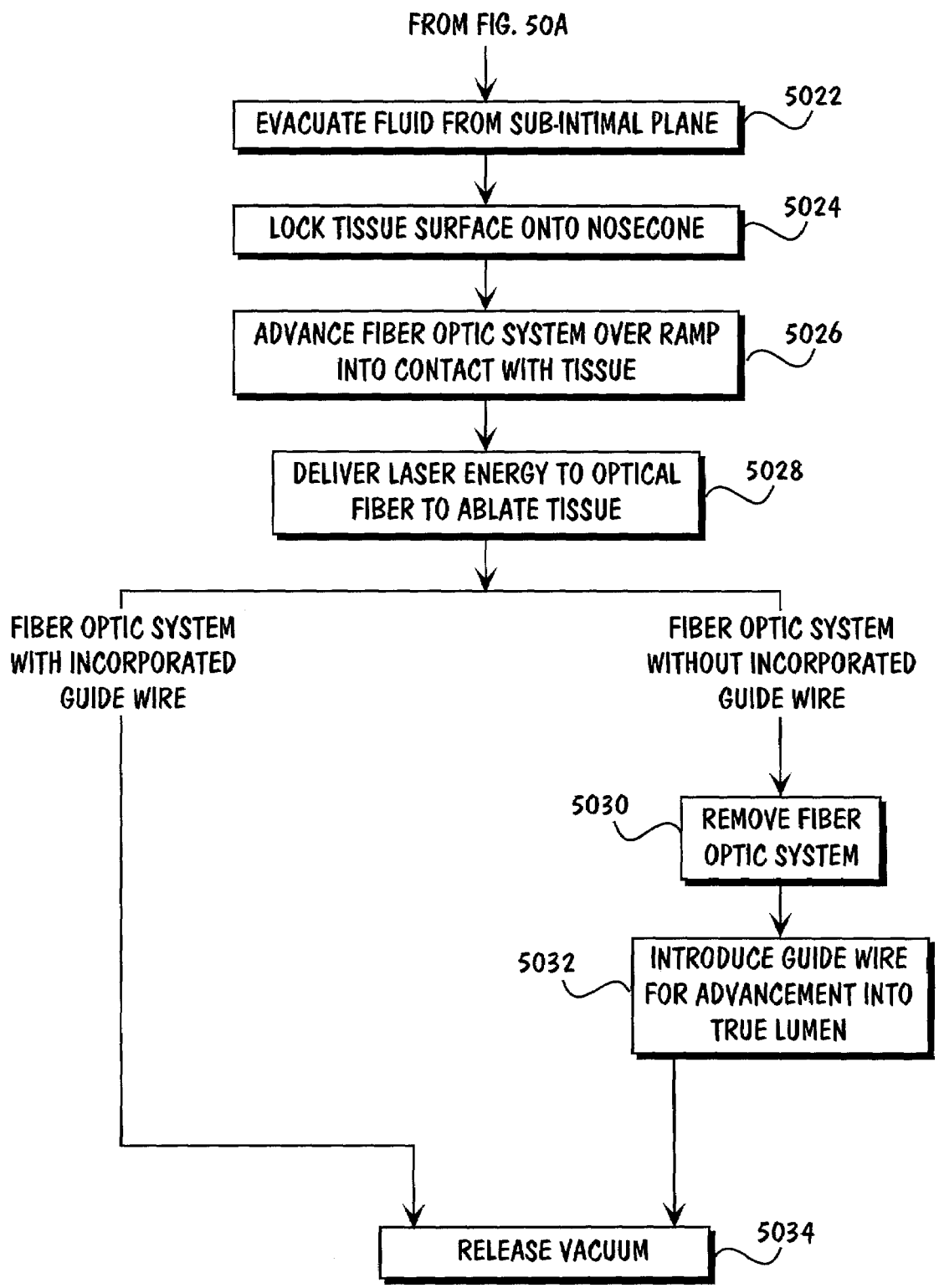

FIGS. 50A and 50B show a flow diagram for creating a path into a vessel true lumen using laser energy, under a fourth alternative embodiment. Procedurally, the sliding tube may remain in the catheter at all times. In preparation of the catheter and during delivery of the catheter to the vascular site, the distal end of the tube is retracted just proximal to the nosecone.

The optical fiber system is removed from the catheter and the catheter is tracked over a standard guide wire placed in the desired sub-intimal space of the target vasculature. Because the guide wire emerges laterally from the nosecone, the tip of the catheter will track eccentrically over the guide wire.

Next, the catheter is aligned to the vessel true lumen. This is accomplished per Step 1, Methods 1–4 or Step 1, Method 5. In the case of Methods 1–4, the guide wire is retracted from the catheter, and the visualization element is advanced into the nosecone. The element is activated at the nosecone side port and the side port is rotated to face the vessel true lumen. The visualization element is removed. In the case of Method 5, the side port is rotated to face the vessel true lumen per fluoroscopic visualization. The guide wire is then removed.

The internal sliding tube is then advanced until the distal end reaches the internal stop within the nosecone. The fiber optic system is introduced into the internal sliding tube and advanced to within 2 centimeters of the distal tip of the nosecone. At this point the application of vacuum can be used to evacuate fluid from the sub-intimal plane and lock the sub-intimal tissue onto the surface of the nosecone. Vacuum may be translated to the nosecone via the inner sliding tube, or via the annular lumen between the catheter shaft and the inner sliding tube. The fiber optic system is subsequently advanced distally into the nosecone, engaging the internal ramp, until a distal end reaches the exit of the side port and is in approximate contact with the sub-intimal tissue.

Laser energy is delivered to the optical fiber system as required to ablate the sub-intimal tissue separating the dissection plane from the vessel true lumen. If the fiber optic system without a guide wire is used, the fiber optic system is removed and a standard guide wire is introduced for advancement through the pathway in the sub-intimal tissue and into the true lumen. When the fiber optic system includes a guide wire lumen, a guide wire is advanced through the lumen, through the pathway in the sub-intimal tissue, and into the true lumen. The vacuum is then released, the guide wire position is maintained, and the catheter is retracted from the vasculature, leaving the distal portion of the guide wire in place in the vessel true lumen.

Typical dimensions of the catheter components are as follows: outer shaft/nosecone outside diameter is approximately 0.030 to 0.050 inches; internal slide tube outside diameter is approximately 0.020 to 0.030 inches; and fiber optic system outside diameter is approximately 0.010 to 0.030 inches.

Embodiment 6 (Method 5 under Step 3) (FIG. 13)

This embodiment includes a single lumen catheter shaft, terminated in a "J" tip, used with a fiber optic system, and a standard guide wire. The "J" tip configuration can be torqued into position within the sub-intimal plane and directed towards the sub-intimal tissue. This allows the fiber optic system to be directed at an angle normal to the sub-intimal tissue, to ablate the minimum tissue necessary to establish a pathway across the sub-intimal tissue and into the vessel true lumen.

The "J" termination of the catheter can be fluoroscopically visible in an embodiment to facilitate the positioning process in the sub-intimal plane. This type of termination is fabricated or molded from fluoroscopically visible materials such as platinum coils or gold coated stainless steel coils laminated with a variety of polymers, e.g., nylons, HDPE, and Pebax.

The "J" tip is designed to straighten in order to track over a guide wire to the vascular site, yet re-form to the "J" shape when positioned in the vasculature and the guide wire is retracted. One embodiment incorporates a visualization window just proximal to the "J" tip that is used in conjunction with an on-board visualization technique, per Step 1, Methods 1–4. For the use of IVUS, for example, this window can be fabricated from HDPE.

Figure 51A:
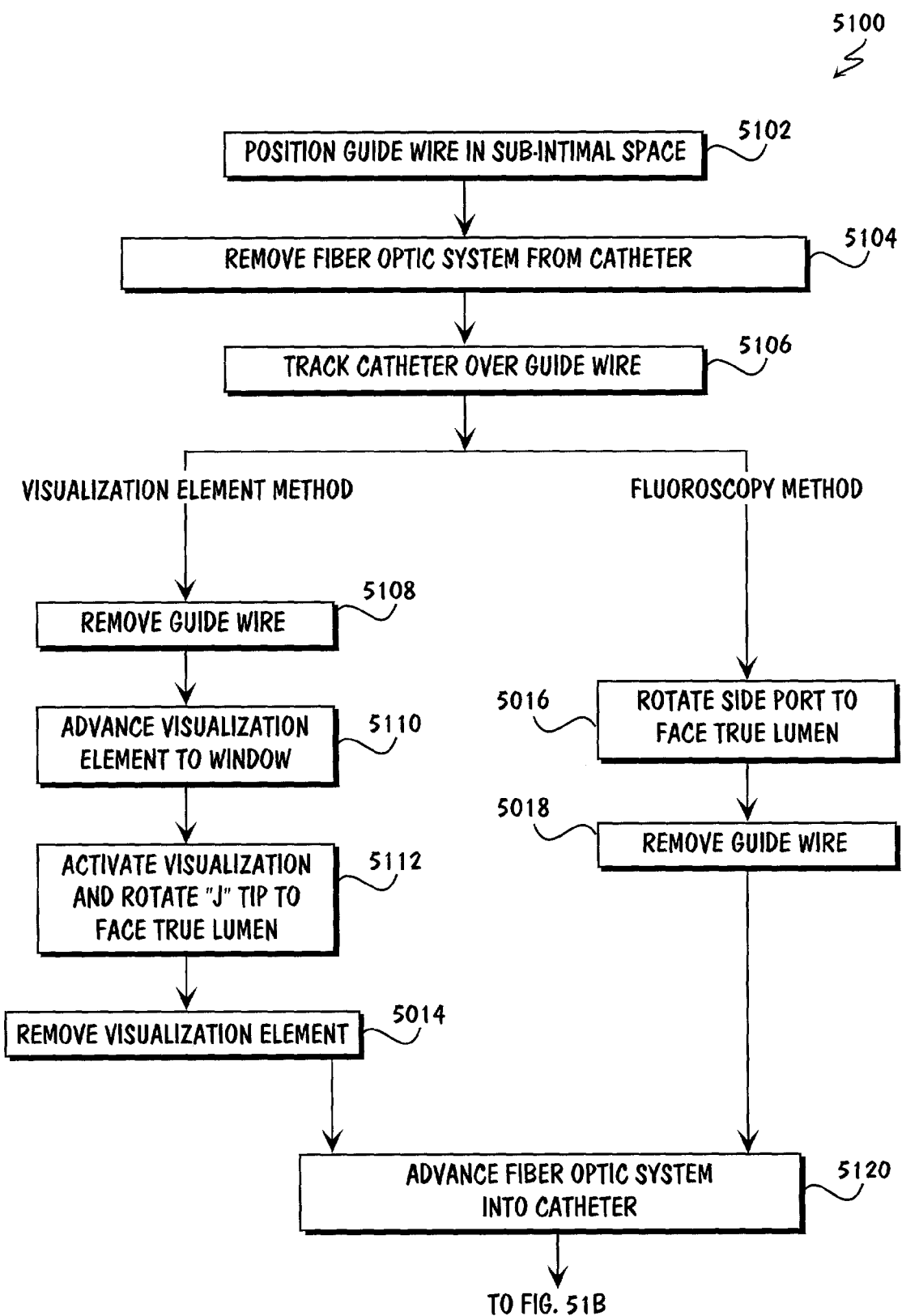
FIGS. 51A and 51B are a flow diagram for establishing a path into a vessel true lumen using laser energy, under a fifth alternative embodiment.
Figure 51B:
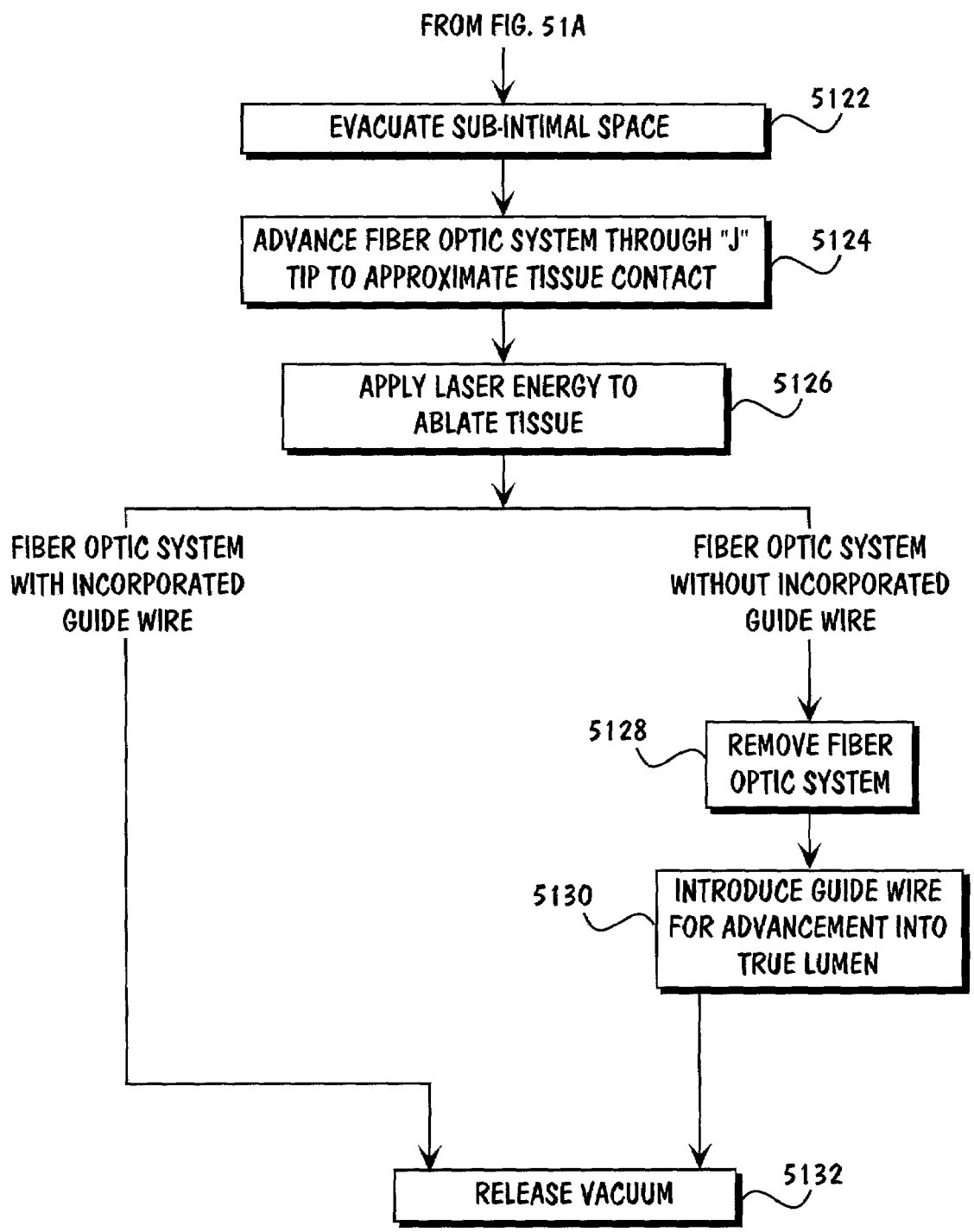

FIGS. 51A and 51B are a flow diagram for creating a path into a vessel true lumen using laser energy, under a fifth alternative embodiment. Procedurally, a guide wire is positioned in the sub-intimal space. The fiber optic system is removed from the catheter. The distal end of the catheter is loaded onto the guide wire. In this process the "J" tip is straightened as it tracks over the wire to the sub-intimal site. Once the terminal end of the catheter has reached the desired location, the guide wire is retracted, allowing the "J" tip to re-form.

The catheter is now aligned to the vessel true lumen per Step 1, Methods 1–4, or Step 1, Method 5. In the case of Methods 1–4, the guide wire is retracted from the catheter, and the visualization element is advanced to the visualization window. The visualization element is activated at the window and the "J" tip is rotated to face the vessel true lumen. The visualization element is then removed. In the case of Method 5, the side port is rotated to face the vessel true lumen per fluoroscopic visualization. The guide wire is then removed.

The fiber optic system is then loaded into the catheter and advanced to within 1 centimeter of the distal end of the catheter tip. Vacuum is applied through the catheter lumen per Step 2, method 1 to evacuate the sub-intimal plane. The fiber optic system is then advanced until its distal end is coincident with the distal end of the catheter "J" tip, and is brought into approximate contact with the sub-intimal tissue.

Laser energy is delivered to the optical fiber system as required to ablate the sub-intimal tissue that separates the dissection plane from the vessel true lumen. If the fiber optic system does not include the guide wire, the fiber optic system is removed and a standard guide wire is introduced to be advanced through the pathway in the sub-intimal tissue and into the true lumen. When the fiber optic system includes a guide wire lumen, a guide wire is advanced through the lumen, through the pathway in the sub-intimal tissue and into the true lumen.

The vacuum is then released, the guide wire position is maintained, and the catheter is retracted from the vasculature, leaving the distal portion of the guide wire in place in the vessel true lumen.

Typical dimensions of the catheter components are as follows: single lumen shaft outside diameter is approximately 0.030 to 0.050 inches; and fiber optic system outside diameter is approximately 0.010 to 0.030 inches.

Embodiment 7 (Method 5 under Step 3) (FIGS. 14A and 14B)

This embodiment includes a catheter having a nosecone with a side port and end port connected by a slot, an internal push-ramp that is actuated by an internal push tube or member, and a fiber optic system slidably disposed in the catheter. This catheter includes a distal nosecone having a side port and a separate end port, a single lumen catheter shaft, and an internal push-tube or member that is attached to an internal hinged ramp which actuates within the nosecone side port. This catheter system may be used with any of the visualization techniques of Step 1.

The push ramp may be constructed of a flexible metal such as Nitinol or spring steel, or a polymer such as nylon or PEEK, any of which can be fabricated with or without appropriate detents to allow for bending, as required. The distal end of the push ramp is connected or hinged about the internal distal termination of the catheter shaft, opposite the side port. When the push tube or member is fully retracted proximally, the push ramp assumes a linear configuration, lying essentially flat against the inside wall of the catheter, opposite the nosecone side port.

When the push tube or member is advanced distally, the push ramp forms an incline that leads from the proximal end of the ramp, opposite the nosecone side port, to the distal end of the side port. This ramp re-directs the fiber optic system or guide wire within the nosecone side port as either is advanced distally through the nosecone side port.

FIG. 52 is a flow diagram for establishing a path into a vessel true lumen using laser energy, under a sixth alternative embodiment. Procedurally, a guide wire is positioned in the sub-intimal space. The push tube or member is retracted proximally, and the distal end of the catheter is loaded onto the guide wire. The catheter is tracked over the guide wire to the desired vascular location.

The catheter is then aligned to the vessel true lumen per Step 1, Methods 1–4, or Step 1, Method 5. When Methods 1–4 are used, the guide wire is retracted from the catheter, and the visualization element is advanced to the visualization window. The visualization element is activated at the nosecone side port and the side port is rotated to face the vessel true lumen. The visualization element is subsequently removed.

When Method 5 is used, the side port is rotated to face the vessel true lumen per fluoroscopic visualization. The guide wire is then removed.

The fiber optic system is loaded into the catheter and the distal end advanced until it is approximately 2 centimeters proximal to the nosecone or proximal to the push ramp. Vacuum is then applied through the catheter lumen per Step 2, method 1 to evacuate the sub-intimal plane. Vacuum may be applied via within the push tube or via the annular space between the push-tube and the catheter shaft. The optical fiber system is then advanced following the ramp to the nosecone cone port until it is brought into contact with the sub-intimal tissue.

Next, laser energy is delivered to the optical fiber system as required to ablate the sub-intimal tissue separating the dissection plane from the vessel true lumen. If the fiber optic system does not incorporate the guide wire, the fiber optic system is removed and a standard guide wire is introduced for advancement through the pathway in the sub-intimal tissue and into the true lumen. When the fiber optic system incorporates a guide wire lumen, a guide wire is simply advanced through the lumen, through the pathway in the sub-intimal tissue and into the true lumen.

The push tube or member is now retracted proximally, collapsing the internal push ramp to a flat configuration, and allowing the guide wire to fall through the slot and into the nosecone distal exit port. The vacuum is then released, the guide wire position is maintained, and the catheter is retracted from the vasculature. As the catheter is retracted, the guide wire will gradually translate through the slot to the nosecone distal end port, allowing the catheter to be retracted over the guide wire in a co-linear fashion, and leaving the distal portion of the guide wire in place in the vessel true lumen.

Typical dimensions of the catheter components are as follows: outer shaft/nosecone outside diameter is approximately 0.030 to 0.050 inches; internal push tube outside diameter is approximately 0.020 to 0.030 inches; and the fiber optic system outside diameter is approximately 0.010 to 0.030 inches.

Embodiment 8 (Method 5 under Step 3) (FIG. 15)

This embodiment includes a dual lumen catheter shaft terminating in a single lumen "J" tip, used in conjunction with an optical fiber system, an optional visualization system, and guide wires. This dual lumen catheter shaft has the same "J" type single lumen distal termination as described in Method 3, Embodiment 7, with the exception that it transitions proximally to a dual lumen catheter shaft. Fabrication and materials for the "J" tip are as described in Method 3, Embodiment 7. The dual lumen catheter shaft may be fabricated using materials and methods known in the art, and as cited in other embodiments in this description. This embodiment allows one of the slidably disposed elements included within either lumen to be advanced individually into the "J" tip single lumen.

The procedure for using this dual lumen catheter is now described with further reference to FIG. 40. The working element described in this figure is the fiber optic system discussed below.

In a first scenario the first lumen of the dual lumen includes a standard guide wire and the second lumen includes a fiber optic system. Procedurally, the fiber optic system is loaded into its lumen and advanced until it is just proximal of the entrance to the distal single lumen ("J" tip). The catheter is loaded onto a guide wire that has been advanced into a sub-intimal plane. The catheter is then advanced over the guide wire until it reaches the desired vascular location, and the guide wire withdrawn just proximal to the entrance to the single lumen. Next, the catheter is aligned to the vessel true lumen. This embodiment makes use of Step 1, Method 5 to align the catheter.

The sub-intimal plane is now evacuated per Step 2, Method 2, and the optical fiber system is advanced into the "J" tip so that its distal end is approximately coincident with the distal tip of the catheter, or pointed towards the sub-intimal tissue. The procedure used dictates whether the tip of the fiber optic system is or is not in contact with the sub-intimal tissue. Laser energy is then delivered as required through the fiber optic system to ablate the sub-intimal tissue and create a pathway into the vessel true lumen. Once the pathway is established, the distal end of the fiber optic system is retracted from the single lumen, and into the dual lumen. The standard guide wire is then advanced into the distal single lumen, and out of the "J" tip, through the pathway produced in the sub-intimal tissue, and into the vessel true lumen. Lastly, the guide wire is held in place while the catheter is retracted proximally and removed from the vasculature.

In a second scenario, the first lumen of the dual lumen initially contains a visualization element, per Step 1, Method 1–4, and is exchanged for the fiber optic system. The second lumen contains a standard guide wire. Procedurally, one lumen of the dual lumen shaft is loaded with the visualization element and advanced proximal to the entrance to the distal single lumen. The distal end of the catheter is then loaded onto a standard guide wire that has been advanced into a sub-intimal plane. The catheter is advanced to the desired vascular location, and the guide wire is removed from the catheter and replaced with the fiber optic system.

The visualization element is then advanced into the distal single lumen within the area of the window for viewing, and the "J" tip is aligned with the vessel true lumen. The visualization element is then withdrawn from the catheter, and a standard guide wire is advance into this lumen to just proximal of the single lumen. Next, the sub-intimal plane is evacuated according to Step 2, Method 2. This may be accomplished through the lumen that houses either the guide wire, the optical fiber system, or both. Next, the optical fiber system is advanced into the "J" tip so that its distal end is approximately coincident with the distal tip of the catheter, or pointed towards the sub-intimal tissue. The tip of the fiber optic system may or may not be required to be in contact with the sub-intimal tissue, as directed by the particular procedure in use.

Laser energy is then delivered as required through the fiber optic system to ablate the sub-intimal tissue and create a pathway into the vessel true lumen. Once the pathway has been established, the distal end of the fiber optic system is retracted from the single lumen, and into the dual lumen. The standard guide wire may then be advanced into the distal single lumen, and out of the "J" tip, through the pathway produced in the sub-intimal tissue, and into the vessel true lumen. Finally, the guide wire is held in place while the catheter is retracted proximally and removed from the vasculature.

Typical dimensions of the catheter components are as follows: single lumen shaft outside diameter is approximately 0.030 to 0.050 inches; the dual lumen shaft outside diameter is approximately 0.030 to 0.050 inches (each lumen); and the fiber optic system outside diameter is approximately 0.010 to 0.030 inches.

Method 6 under Step 3: Rotational IVUS Element (FIGS. 9, 11–15, and 19)

This method describes re-entry using a rotational IVUS element including a specialized distal boring tip.

Embodiment 1 (Method 6 under Step 3) (FIG. 9)

This embodiment includes a nosecone or molded catheter termination attached to the distal end of the catheter, an internal slidably disposed actuating cannula, and an IVUS system with a specialized tip. Dimensions of the catheter components are as follows: the single lumen shaft outside diameter is approximately 0.055 inches; the cannula element outside diameter is approximately 0.040 inches; and the IVUS system outside diameter is approximately 0.030 inches.

Procedurally, with further reference to FIG. 34, this embodiment is similar to that described for Method 3, Embodiment 3, with the exception that the IVUS system with the specialized tip provides visualization as well as the subsequent re-entry mechanism.

Embodiment 2 (Method 6 under Step 3) (FIG. 11)

This embodiment includes a catheter having a nosecone or molded distal termination, a single lumen catheter shaft and an IVUS system with a specialized tip. Dimensions of the catheter components are as follows: outer shaft/nosecone outside diameter is approximately 0.045 inches; and the IVUS system outside diameter is approximately 0.030 inches.

Procedurally, with further reference to FIG. 36, this embodiment is similar to that described for Method 3, Embodiment 5, with the exception that the IVUS system with a specialized tip provides visualization as well as the subsequent re-entry mechanism.

Embodiment 3 (Method 6 under Step 3) (FIG. 12)

This embodiment includes a catheter having a nosecone or molded distal termination, a single lumen catheter shaft, an internal slidably disposed tube, the distal end of which translates within the catheter nosecone, and an IVUS system with a specialized tip. Dimensions of the catheter components are as follows: outer shaft/nosecone outside diameter is approximately 0.050 inches; the internal slide tube outside diameter is approximately 0.040 inches; and the IVUS system outside diameter is approximately 0.030 inches.

Procedurally, with further reference to FIG. 37, this embodiment is similar to that described for Method 3, Embodiment 6, with the exception that the IVUS system with a specialized tip provides visualization as well as the subsequent re-entry mechanism.

Embodiment 4 (Method 6 under Step 3) (FIG. 13)

The embodiment includes a single lumen catheter shaft, terminated in a "J" tip, and an IVUS system with a specialized tip. Dimensions of the catheter components are as follows: the single lumen shaft outside diameter is approximately 0.040 inches; and the IVUS system outside diameter is approximately 0.030 inches.

Procedurally, with further reference to FIG. 38, this embodiment is similar to that described for Method 3, Embodiment 7, with the exception that the IVUS system with a specialized tip provides visualization as well as the subsequent re-entry mechanism.

Embodiment 5 (Method 6 under Step 3) (FIG. 14)

This embodiment includes a catheter having a nosecone or molded distal termination, an internal push-ramp which is actuated by an internal push tube or member, a single lumen catheter shaft, and an IVUS system with specialized tip. Dimensions of the catheter components are as follows: outer shaft/nosecone outside diameter is approximately 0.050 inches; the internal push tube outside diameter is approximately 0.040 inches; and the IVUS system outside diameter is approximately 0.030 inches.

Procedurally, with further reference to FIG. 39, this embodiment is similar to that described for Method 3, Embodiment 8, with the exception that the IVUS system with a specialized tip provides visualization as well as the subsequent re-entry mechanism.

Embodiment 6 (Method 6 under Step 3) (FIG. 15)

FIG. 15 is an embodiment that includes a dual lumen catheter shaft, terminated in a single lumen "J" tip, and an IVUS system with specialized tip. Dimensions of the catheter components are as follows: the single lumen shaft outside diameter is approximately 0.040 inches; the dual lumen shaft outside diameter is approximately 0.040 inches (per lumen); and the IVUS system outside diameter is approximately 0.030 inches.

Procedurally, with further reference to FIG. 40, this embodiment is similar to that described under Method 3, Embodiment 9, with the exception that the IVUS system with a specialized tip provides visualization as well as the subsequent re-entry mechanism.

In general, alternatives and alternative embodiments described herein are substantially similar to previously described embodiments, and common elements and acts or steps are identified by the same reference numbers. Only significant differences in construction or operation are described in detail. The elements and acts of the various embodiments described above can be combined to provide further embodiments.

All of the above references and U.S. patents and applications are incorporated herein by reference. Aspects of the invention can be modified, if necessary, to employ the systems, functions and concepts of the various patents and applications described above to provide yet further embodiments of the invention.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," and words of similar import, when used in this application, shall refer to this application as a whole and not to any particular portions of this application.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings of the invention provided herein can be applied to other catheter systems, not only for the catheter system described above.

In general, in the following claims, the terms used should not be construed to limit the invention to the specific embodiments disclosed in the specification and the claims, but should be construed to include all medical systems that operate under the claims. Accordingly, the invention is not limited by the disclosure, but instead the scope of the invention is to be determined entirely by the claims.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

What we claim is:

1. A method for forming a pathway from a sub-intimal space of a blood vessel into a true lumen of the blood vessel, comprising:

positioning a catheter system within the sub-intimal space at a position proximate to a target entry site into the true lumen, the catheter system including at least one lumen in communication with at least one port in a distal region of the catheter system, the catheter system further including an internal incising element that is translatable across a portion of the port;

determining a radial position of the true lumen with respect to the port at the target entry site from a position in the sub-intimal plane using an imaging device of the catheter system; and forming an incision in tissue separating the sub-intimal space from the true lumen using the internal incising element, the incision having separate and distinct end points and forming a pathway between the sub-intimal space and the true lumen, wherein the tissue remains external to the port subsequent to forming the incision.

2. The method of claim 1, wherein the imaging device is a rotational imaging device.

3. The method of claim 1, wherein the imaging device is an ultrasonic device.

4. The method of claim 1, wherein the imaging device is an optical coherence tomography (OCT) device.

5. The method of claim 1, wherein the incising element is integral to the imaging device.

6. The method of claim 1, wherein the incising element is separate from and arranged concentrically outside the imaging device.

7. The method of claim 1, wherein determining the radial position includes use of an imaging device that is a fixed integral part of a body of the catheter system.

8. The method of claim 1, wherein determining the radial position includes use of a fluoroscopic marker on the catheter system.

9. The method of claim 8, wherein the fluoroscopic marker is located on a body of the catheter system.

10. The method of claim 8, wherein the fluoroscopic marker is located on one or more working elements of the catheter system.

11. The method of claim 1, further comprising evacuating fluid from the sub-intimal space and securing the tissue separating the sub-intimal space from the true lumen at the port by applying vacuum to the catheter lumen.

12. The method of claim 11, further comprising invaginating the tissue separating the sub-intimal space from the true lumen into the port and into a distal interior region of the catheter system upon application of the vacuum.

13. The method of claim 1, further comprising advancing a working element into the true lumen through the incision.

14. The method of claim 13, wherein the working element includes at least one of a guide wire and a cannula.

15. A method for forming a pathway from a sub-intimal space of a blood vessel into a true lumen of the blood vessel, comprising:
- positioning a catheter system within the sub-intimal space at a position proximate to a target entry site into the true lumen, the catheter system including at least one lumen in communication with at least one port in a distal region of the catheter system, the catheter system further including an internal incising element that is translatable across a portion of the port; and
- forming an incision in tissue separating the sub-intimal space from the true lumen using the internal incising element, the incision having separate and distinct end points and forming a pathway between the sub-intimal space and the true lumen, wherein the tissue remains external to the port subsequent to forming the incision.

16. A method for forming a pathway from a sub-intimal space of a blood vessel into a true lumen of the blood vessel, comprising:
- positioning a catheter system within the sub-intimal space at a position proximate to a target entry site into the true lumen, the catheter system including at least one lumen in communication with at least one port in a distal region of the catheter system, the catheter system further including an internal excising element that is translatable across a portion of the port;
- determining a radial position of the true lumen with respect to the port at the target entry site from a position in the sub-intimal plane using an imaging device of the catheter system;
- advancing the internal excising element along a portion of the port; and
- excising an area of tissue separating the sub-intimal space from the true lumen using the internal excising element, the excised area of tissue generating a pathway from the sub-intimal space to the true lumen.

17. A method for forming a pathway from a sub-intimal space of a blood vessel into a true lumen of the blood vessel, comprising:
- positioning a catheter system within the sub-intimal space at a position proximate to a target entry site into the true lumen, the catheter system including at least one lumen in communication with at least one port in a distal region of the catheter system, the catheter system further including an internal excising element that is translatable across a portion of the port;
- advancing the internal excising element along a portion of the port; and
- excising an area of tissue separating the sub-intimal space from the true lumen using the internal excising element, the excised area of tissue generating a pathway from the sub-intimal space to the true lumen.

18. A method for establishing a pathway through a chronic total occlusion of a blood vessel, the pathway connecting a first region of a true lumen of the blood vessel which is proximal to the occlusion to a second region of the true lumen of the blood vessel distal to the occlusion via an extra-luminal pathway within the vessel, comprising:
- forming a track longitudinally from the first region of the true lumen through the occlusion and into a sub-intimal space distal to the occlusion;
- positioning a catheter system within the sub-intimal space using the track, the catheter system including at least one lumen in communication with at least one port in a distal region of the catheter system, the catheter system further including an internal incising element that is translatable across a portion of the port;
- determining a radial position of the true lumen with respect to the port using an imaging device of the catheter system; and
- forming an incision in tissue separating the sub-intimal space from the true lumen using the internal incising element, the incision having separate and distinct end points and forming a pathway between the sub-intimal space and the true lumen, wherein the tissue remains external to the port subsequent to forming the incision.

19. A method for establishing a pathway through a chronic total occlusion of a blood vessel, the pathway connecting a first region of a true lumen of the blood vessel which is proximal to the occlusion to a second region of the true lumen distal to the occlusion via an extra-luminal pathway within the vessel, comprising:
- forming a track longitudinally from the first region of the true lumen through the occlusion and into a sub-intimal space distal to the occlusion;
- positioning a catheter system within the sub-intimal space using the track, the catheter system including at least one lumen in communication with at least one port in a distal region of the catheter system;
- determining a radial position of the true lumen with respect to the port using an imaging device of the catheter system;
- applying a vacuum through the catheter lumen and the port, evacuating fluid from the sub-intimal space and bringing the sub-intimal tissue into intimate contact with the port; and
- advancing a working element through the port and through the tissue separating the sub-intimal space and the second region of the true lumen and generating a pathway from the sub-intimal space to the second region of the true lumen.

* * * * *